US007799901B2

(12) United States Patent
Wallach et al.

(10) Patent No.: US 7,799,901 B2
(45) Date of Patent: Sep. 21, 2010

(54) MODULATORS OF THE FUNCTION OF FAS RECEPTORS AND OTHER PROTEINS

(75) Inventors: David Wallach, Rehovot (IL); Mark Boldin, Rehovot (IL); Tanya Goncharov, Rehovot (IL); Yury V. Golstev, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 11/522,472

(22) Filed: Sep. 18, 2006

(65) Prior Publication Data

US 2007/0154905 A1 Jul. 5, 2007

Related U.S. Application Data

(62) Division of application No. 10/368,438, filed on Feb. 20, 2003, now abandoned, which is a division of application No. 09/516,747, filed on Mar. 1, 2000, now Pat. No. 6,586,571, which is a division of application No. 08/983,502, filed as application No. PCT/US96/10521 on Jun. 14, 1996, now Pat. No. 6,399,327.

(30) Foreign Application Priority Data

| Jul. 16, 1995 | (IL) | ..................................... 114615 |
| Aug. 17, 1995 | (IL) | ..................................... 114986 |
| Sep. 14, 1995 | (IL) | ..................................... 115319 |
| Dec. 27, 1995 | (IL) | ..................................... 116588 |
| Apr. 16, 1996 | (IL) | ..................................... 117932 |

(51) Int. Cl.
*C12P 21/08* (2006.01)
*C07K 14/00* (2006.01)

(52) U.S. Cl. ................. 530/387.9; 530/387.1; 530/380; 530/350; 530/388.1

(58) Field of Classification Search .............. 530/388.1, 530/387.9, 387.1, 380, 350
See application file for complete search history.

(56) References Cited

U.S. PATENT DOCUMENTS

| 5,194,596 A | 3/1993 | Tischer et al. |
| 5,350,836 A | 9/1994 | Kopchick et al. |
| 5,786,173 A | 7/1998 | Alnemri et al. |
| 5,837,837 A | 11/1998 | Hunter et al. |
| 6,008,042 A | 12/1999 | Dixit et al. |
| 6,172,190 B1 | 1/2001 | Hunter et al. |

FOREIGN PATENT DOCUMENTS

| WO | WO 95/31544 A1 | 11/1995 |
| WO | WO 96/13603 A1 | 5/1996 |
| WO | WO 96/18641 A1 | 6/1996 |
| WO | WO 96/25941 A1 | 8/1996 |
| WO | WO 96/31603 A2 | 10/1996 |
| WO | WO 97/35006 A1 | 9/1997 |
| WO | WO 97/46662 A1 | 12/1997 |
| WO | WO 98/44104 A2 | 10/1998 |

OTHER PUBLICATIONS

Agrawal et al.,"Antisense therapeutics: is it as simple as complementary base recognition?," *Mol Med Today* 6(2):72-81 (2000).
Anderson WF,"Human Gene Therapy", *Nature* 392(Sup):25-30 (1998).
Baker et al, "Transducers of life and death: TNF receptor superfamily and associated proteins", *Oncogene* 12:1-9 (1996).
Benjamin et al, "A plasticity window for blood vessel remodelling is defined by pericyte coverage of the preformed endothelial network and is regulated by PDGF-B and VEGF", *Development* 125(9):1591-1598 (1998).
Boldin et al, "Involvement of the MORT1/FADD-interacting protease, L21 mach, in FAS/APO1-mediated apoptosis", *Eur Cytokine Netw* 7:(2):199 (1996).
Boldin et al, "A novel protein that interacts with the death domain of FAS/APO1 contains a sequence motif related to the death domain", *J Biol Chem* 259(11):7795-7798 (1996).
Boldin et al,"A novel protein that interacts with the death domain of Fas/APO1 contains a sequence motif related to the death domain", *J Biol Chem* 270(14):7795-7798 (1995).
Bork P, "Powers and pitfalls in sequence analysis: the 70% hurdle", *Genome Res* 10(4):398-400 (2000).
Bork P, "Go hunting in sequence databases but watch out for the traps", *Trends Genet* 12(10):425-427 (1996).
Branch A, "A good antisense molecule is hard to find," *Trends Biochem Sci* 23(2):45-50 (1998).
Brenner S, "Errors in genome annotation", *Trends Genet* 15(4):132-133 (1999).
Chinnaiyan et al, "FADD/MORT1 is a common mediator of CD95 (FAS/APO-1) and tumor necrosis factor receptor-induced apoptosis", *J Biol Chem* 271(9):4961-4965 (1996).
Chinnaiyan et al, "FADD, a novel death domain-containing protein, interacts with the death domain of fas and initiates apoptosis", *Cell* 81:505-512 (1995).
Chirila et al,"The use of synthetic polymers for delivery of therapeutic antisense oligodeoxynucleotides," *Biomaterials* 23(2):321-342 (2002).
Crooke S (Ed.), *Antisense Research and Application*, Chapter 1, pp. 1-50 (Springer-Verlag, 1998).
Derossi et al,"The third helix of the Antennapedia homeodomain translocates through biological membranes," *J Biol Chem* 269(14):10444-10450 (1994).
Doerks et al,"Protein annotation: detective work for function prediction", *Trends Genet* 14(6):248-250 (1998).
Elliott et al,"Intercellular trafficking and protein delivery by a herpesvirus structural protein," *Cell* 1997 88(2):223-233 (1997).
Enari et al, "Involvement of an ice-like protease in FAS-mediated apoptosis", *Nature* 375:78-81 (1995).

(Continued)

*Primary Examiner*—T. D. Wessendorf
(74) *Attorney, Agent, or Firm*—Browdy and Neimark, PLLC

(57) ABSTRACT

The present invention provides proteins capable of modulating or mediating the FAS receptor ligand or TNF effect on cells carrying FAS receptor or p55 receptor by binding or interacting with MORT-1 protein, which in turn binds to the intracellular domain of the FAS receptor or to another protein TRADD which binds to the p55 receptor. In addition, peptide inhibitors that interfere with the proteolytic activity of MORT-1-binding proteins having proteolytic activity are provided, as well as a method of designing them.

3 Claims, 22 Drawing Sheets

OTHER PUBLICATIONS

Fernandes-Alnemri et al, "MCH3, a novel human apoptotic cysteine protease highly related to CPP32", *Cancer Res* 55:6045-6052 (1995).

Hillier et al, "Soares melanocyte 2NbHM Homo Sapiens cDNA clone image: 270980", Database EMBL, accession No. N42544 (1996).

Hillier et al, "Soares fetal liver spleen 1NFLS Homo Sapiens cDNA clone Image: 111668"; Database EMBL, Accession No. T84692 (1995).

Hsu et al, "The TNF receptor 1-associated protein TRADD signals cell death and NF-kappaβ activation", *Cell* 81:495-504 (1996).

Loetscher et al, "Molecular cloning and expression of the human 55 kd tumor necrosis factor receptor", *Cell* 61(2):351-359 (1990).

Ngo et al, "Computational Complexity, Protein Structure Prediction and the Leventhal Paradox", in *The Protein Folding Problem and Tertiary Structure Prediction*, Chapter 14, Metz and Grand, eds., Birkhauser, Boston, pp. 491-495 (1994).

Pai et al, "Purification and cDNA cloning of a second apoptosis-related cysteine protease that cleaves and activates sterol regulatory element binding proteins", *Proc Natl Acad Sci USA* 93(11):5437-5442 (1996).

Peracchi et al, "Prospects for antiviral ribozymes and deoxyribozymes, " *Rev Med Virol* 14(1):47-64 (2004).

Pilbeam et al, "Comparison of the effects of various lengths of synthetic human parathyroid hormone-related peptide (hPTHrP) of malignancy on", bone resorption and formation in organ culture, *Bone* 14(5):717-720 (1993).

Pooga et al,"Cell penetration by transportan," *FASEB J* 12(1):67-77 (1998).

Schlegel et al, "Isolation and partial characterization of a protease involved in FAS-induced apoptosis", *FEBS Lett* 364:139-142 (1995).

Skolnick et al, "From genes to protein structure and function: novel applications of computational approaches in the genomic era" *Trends Biotechnol* 18(1):34-39 (2000).

Smith et al, "The challenges of genome sequence annotation or 'the devil is in the details'", *Nat Biotechnol* 15(12):1222-1223 (1997).

Stanger et al, "RIP: a novel protein containing a death domain that interacts with FAS/APO-1 (CD95) in yeast and causes cell death", *Cell* 81:513-523 (1995).

Stull et al, "Antigene, ribozyme and aptamer nucleic acid drugs: progress and prospects", *Pharmaceutical Research* 12(4):465-483 (1995).

Varfolomeev et al, "A potential mechanism of "cross-talk" between the p55 tumor necrosis factor receptor and fas/apo1: protein binding to the death domain of the two receptors also bind to each other", *J Exp Med* 183:1271-1275(1996).

Vukicevic et al, "Induction of nephrogenic mesenchyme by osteogenic protein 1 (bone morphogenetic protein 7)", *Proc Natl Acad Sci USA* 93(17):9021-9026 (1996).

Wells J, "Additivity of mutational effects in proteins", *Biochemistry* 29(37):8509-8017 (1990).

| DNA-BINDING-DOMAIN HYBRID | ACTIVATION-DOMAIN HYBRID | | | | | |
|---|---|---|---|---|---|---|
| | MORT1 | | | human Fas-IC | SNF4 | PGAD-GH |
| | Full | 1-117 | 130-245 | | | |
| Human Fas-IC | | | | | | |
| Full ('Death Domain') | ++ | − | + | ++ | − | − |
| 200-319 | ++ | | | ++ | − | − |
| 233-319 | − | | | − | − | − |
| 175-304 | ++ | − | + | ++ | − | − |
| Mouse Fas-IC | | | | | | |
| Full | ++ | − | ++ | ++ | − | − |
| 197-306 | ++ | − | + | ++ | − | − |
| I225N | − | − | − | ++ | − | − |
| I225A | − | | | ++ | − | − |
| MORT1 | | | | | | |
| Full ('Death Domain motif') | ++ | ++ | − | ++ | − | − |
| 1-117 | + | − | − | − | − | − |
| 130-245 | − | | − | ++ | − | − |
| SPECIFICITY TESTS | | | | | | |
| human p55-IC | − | | | − | − | − |
| human p75-IC | − | | | − | − | − |
| human CD40-IC | − | | | − | − | − |
| Cyclin D | − | | | − | − | − |
| Lamin | − | | | − | − | − |
| SNF1 | − | | | − | + | − |
| pGBT9 | − | | | − | − | − |

FIG. 1

```
1/1                                        31/11
GTG AAT CAG GCA CCG GAG TGC AGG TTC GGG    GGT GGA ATC CTT GGG CCG CTG GGC AAG CGG
 V   N   Q   A   P   E   C   R   F   G     G   G   I   L   G   P   L   G   K   R
61/21                                      91/31
CGA GAC CTG GCC AGG GCC AGC GAG CCG AGG    ACA GAG GGC GCG CGG AGG GCC GGG CCG CAG
 R   D   L   A   R   A   S   E   P   R     T   E   G   R   R   R   A   G   P   Q
121/41                                     151/51
CCC CGG CCG CTT GCA GAC CCC GCC ATG GAC    CCG TTC CTG GTG CTG CTG CAC TCG GTG TCG
 P   R   P   L   A   D   P   A   M   D     P   F   L   V   L   L   H   S   V   S
181/61                                     211/71
TCC AGC CTG TCG AGC AGC GAG CTG ACC GAG    CTC AAG TTC CTA TGC CTC GGG CGC GTG GTC
 S   S   L   S   S   S   E   L   T   E     L   K   F   L   C   L   G   R   V   V
241/81                                     271/91
AAG CGC AAG CTG GAG CGC GTG CAG AGC GGC    CTA GAC CTC TTC TCC ATG CTG CTG GAG CAG
 K   R   K   L   E   R   V   Q   S   G     L   D   L   F   S   M   L   L   E   Q
301/101                                    331/111
AAC GAC CTG GAG CCC GGG CAC ACC GAG CTC    CTG CGC GAG CTG CTC GCC TCC CTG CGG CGC
 N   D   L   E   P   G   H   T   E   L     L   R   E   L   L   A   S   L   R   R
361/121                                    391/131
CAC GAC CTG CTG CGG CGC GTC GAC GAC TTC    GAG GCG GGG GCG GCG GCC GGG GCC GCG CCT
 H   D   L   L   R   R   V   D   D   F     E   A   G   A   A   A   G   A   A   P
421/141                                    451/151
GGG GAA GAA GAC CTG TGT GCA GCA TTT AAC    GTC ATA TGT GAT AAT GTG GGG AAA GAT TGG
 G   E   E   D   L   C   A   A   F   N     V   I   C   D   N   V   G   K   D   W
481/161                                    511/171
AGA AGG CTG GCT CGT CAG CTC AAA GTC TCA    GAC ACC AAG ATC GAC AGC ATC GAG GAC AGA
 R   R   L   A   R   Q   L   K   V   S     D   T   K   I   D   S   I   E   D   R
541/181                                    571/191
TAC CCC CGC AAC CTG ACA GAG CGT GTG CGG    GAG TCA CTG AGA ATC TGG AAG AAC ACA GAG
 Y   P   R   N   L   T   E   R   V   R     E   S   L   R   I   W   K   N   T   E
601/201                                    631/211
AAG GAG AAC GCA ACA GTG GCC CAC CTG GTG    GGG GCT CTC AGG TCC TGC CAG ATG AAC CTG
 K   E   N   A   T   V   A   H   L   V     G   A   L   R   S   C   Q   M   N   L
661/221                                    691/231
GTG GCT GAC CTG GTA CAA GAG GTT CAG CAG    GCC CGT GAC CTC CAG AAC AGG AGT GGG GCC
 V   A   D   L   V   Q   E   V   Q   Q     A   R   D   L   Q   N   R   S   G   A
721/241                                    751/251
ATG TCC CCG ATG TCA TGG AAC TCA GAC GCA    TCT ACC TCC GAA GCG TCC TGA TGG GCC GCT
 M   S   P   M   S   W   N   S   D   A     S   T   S   E   A   S   *
781/261                                    811/271
GCT TTG CGC TGG TGG ACC ACA GGC ATC TAC    ACA GCC TGG ACT TTG GTT CTC TCC AGG AAG
841/281                                    871/291
GTA GCC CAG CAC TGT GAA GAC CCA GCA GGA    AGC CAG GCT GAG TGA GCC ACA GAC CAC CTG
901/301                                    931/311
CTT CTG AAC TCA AGC TGC GTT TAT TAA TGC    CTC TCC CGC ACC AGG CCG GGC TTG GGC CCT
961/321                                    991/331
GCA CAG ATA TTT CCA TTT CTT CCT CAC TAT    GAC ACT GAG CAA GAT CTT GTC TCC ACT AAA
1021/341                                   1051/351
TGA GCT CCT GCG GGA GTA GTT GGA AAG TTG    GAA CCG TGT CCA GCA CAG AAG GAA TCT GTG
1081/361                                   1111/371
CAG ATG AGC AGT CAC ACT GTT ACT CCA CAG    CGG AGG AGA CCA GCT CAG AGG CCC AGG AAT
1141/381                                   1171/391
CGG AGC GAA GCA GAG AGG TGG AGA ACT GGG    ATT GAA CCC CGC ATC CTT CAC CAG AGC
1201/401                                   1231/411
CCA TGC TCA ACC ACT GTG GCG TTC TGC TGC    CCC TGC AGT TGG CAG AAA GGA TGT TTT TGT
1261/421                                   1291/431
CCC ATT TCC TTG GAG GCC ACC GGG ACA GAC    CTG GAC ACT AGG GTC AGG CGG GGT GCT GTG
1321/441                                   1351/451
GTG GGG AGA GGC ATG GCT GGG GTG GGG GTG    AGA CCT GGT TGG CCG TGG TCC AGC TCT
1381/461                                   1411/471
TGG CCC CTG TGT GAG TTG AGT CTC CTC TCT    GAG ACT GCT AAG TAG GGG CAG TGA TGG TTG
1441/481                                   1471/491
CCA GGA CGA ATT GAG ATA ATA TCT GTG AGG    TGC TGA TGA GTG ATT GAC ACA CAG CAC TCT
1501/501                                   1531/511
CTA AAT CTT CCT TGT GAG GAT TAT GGG TCC    TGC AAT TCT ACA GTT TCT TAC TGT TTT GTA
1561/521                                   1591/531
TCA AAA TCA CTA TCT TTC TGA TAA CAG AAT    TGC CAA GGC AGC GGG ATC TCG TAT CTT TAA
1621/541                                   1651/551
AAA GCA GTC CTC TTA TTC CTA AGG TAA TCC    TAT TAA AAC ACA GCT TTA CAA CTT CCA TAT
1681/561
TAC AAA AAA AAA AAA AAA AAA
```

FIG. 2 ccgccgccgccgccgccacctgcccagactttctgttccagggtcagcctgtagtgaatcggcc gctgagcctgaaggaccaacagacgttcgcgcgctctgtgggtctcaaatggcgcaaggtg gggcgctcactgcagcgaggctgccgggcgctgcgggacccggcgctggactcgctggccta cgagtacgagcg....

FIG.3

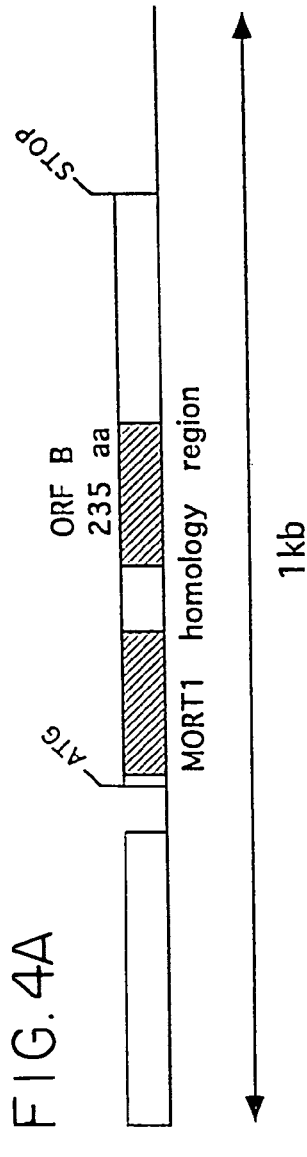

```
        10         20         30         40         50         60         70         80
  1 MDFSRNLYDI GEQLDSEDLA SLKFLSLDYI PQRKQEPIKD ALMLFQRLQE KRMLEESNLS FLKELLFRIN RLDLLITYLN  80
 81 TRKEEMEREL QTPGRAQISA YRVMLYQISE EVSRSELRSF KFLLQEEISK CKLDDDMNLL DIFIEMEKRV ILGEGKLDIL 160
161 KRVCAQINKS LLKIINDYEE FSKERSSSLE GSPDEFSNDF GQSLPNEKQT SGILSDHQQS QFCKSTGESA QTSQH      235
```

FIG. 4C

```
         10         20         30         40         50         60         70         80
  1 CGAGGCCACG AAGGCCGGCT GCCTGAGGAA TACCAGTGGG CAAGAGAATT AGCATTTCTG GAGCATCTGC TGTCTGAGCA   80
 81 GCCCCTGGGT GCGTCCACTT AGATTATATT CTCCTGCCTT TGAGGTTGGG CCTTGGCCGC CTGAGCCCTT GAGTTGGTCA CTTGAACCTT  160
161 GGGAATATTG ATCTGGCCTC CCTCAAGTTC CTGAGCCTGG ACTACATTCC AGAAATCTTT GCAAAGGAAG ATGATATTGG GGAACAACTG  240
241 GACAGTGAAG ATCTGGCCTC TCTCAAGTTC CTGAGCCTGG ACTACATTCC AGAAATCTTT GCAAAGGAAG ATGATATTGG GGAACAACTG  320
321 CTTGATGTTA TCCAGAGAC TCCAGGAAAA GAGAATGTTG GAGGAAAGCA ATCTGTCCTT CCTGAAGGAG CTGCTCTTCC  400
401 GAATTAATAG ACTGGATTTG CTGATTACCT ACCTAAACAC TAGAAAGGAG GAGATGGAAA GGGAACTTCA GACACCAGGC  480
481 AGGGCTCAAA TTTCTGCCTA CAGGGTCATG CTCTATCAGA TTTCAGAAGA AGTGAGCAGA GAGGAATTGA GGTCTTTTAA  560
561 GTTTCTTTTG CAAGAGGAAA TCTCCAAATG CAAACTGGAT GATGACATGA ACCTGCTGGA TATTTTCATA GAGATGGAGA  640
641 AGAGGGTCAT CCTGGGAGAA GGAAAGTTGG ACATCCTGAA AAGAGTCTGT GCCCAAATCA ACAAGAGCCT GCTGAAGATA  720
721 ATCAACGACT ATGAAGAATT CAGCAAAGAG AGAAGCAGCA AGCCTTGAAG AAGTCCTGAT GAATTTTGCA ATGACTTTGG  800
801 ACAAAGTTTA CCAAATGAAA AGCAAACCTC TCTGATCATC AACAATCACA ATTTTGCAAA AGCACGGGAG  880
881 AAAGTGCCCA AACTTCACAG CATTAGGGAC TGCAGGGTTT TGCAGGGTTT TGAGAATGTTT TTAGCTGGTG  960
961 GCAATAAATA TTAGAAGCCT GCAGAATCCA CACACTTGA TAGAGGGTTT CCTTCTTGGG CCTTCGTGGC CTCGAG     1036
```

MDFSRNLYDIGEQLDSEDLASLKFLSLDYIPQRKQEPIKDALMLFQRLQE 50
KRMLEESNLSFLKELLFRINRLDLLITYLNTRKEEMERELQTPGRAQISA 100
YRVMLYQISEEVSRSELRSFKFLLQEEISKCKLDDDMNLLDIFIEMEKRV 150
ILGEGKLDILKRVCAQINKSLLKIINDYEEFSKERSSSLEGSPDEFSNDF 200
GQSLPNEKQTSGILSDHQQSQFCKSTGESAQTSQH 235

FIG.7A

```
MORT1    4    FLVLLHSVSSSISSSELTELKFLCLGRVGKRKLERVQSG       42
MACH     3    FSRNLYDIGEQLDSEDLASLKFLSLDYIPQRKQEPIKDA'      41
MACH   101    YRVMLYQISEEVSRSELRSFKFLLQEEISKCKLDDDMNL      139
PEA-15   4    YGTLFQDLTNNITLEDLEQLKSACKEDPSEKSEEITTG        42

MORT1   43    LDLFSMLLEQNDLEPGHTELLKEESNLSFLKELLRRHDLLRRVDD    81
MACH    42    LMLFQRLQEKRMLEESNLSFLKELLFRINRLDLLITYLN          80
MACH   140    LDIFIEMEKRVILGEGKLDILKRVCAQINK-SLLKIIND         177
PEA-15  43    SAWFSFLESHNKLDKDNLSITEHIFEISRRPDLLTMVVD          81
```

1st MORT module

```
MACH α1        MDFSRNLYDIGEQLDSEDLASLKFLSLDYIPQRKQEPIKDALMLFQRLQEKRMLEESNLSFLK   63
MACH β1        MDFSRNLYDIGEQLDSEDLASLKFLSLDYIPQRKQEPIKDALMLFQRLQEKRMLEESNLSFLK   63
MACH β3        MDFSRNLYDIGEQLDSEDLASLKFLSLDYIPQRKQEPIKDALMLFQRLQEKRMLEESNLSFLK   63

CED-3          ------------------IKVDEILEVLIAKQVLNSD-----GDMINSCGTVREKREIVKAVQRR----GDVAFDAFYDAL    76
Ich-11/Nedd2   MMFSSH------MPHHQETLKKNRVVLAKQ-ILLSELFE----HLFEKDIITLEMELIQAKVGSFSQNVELLNLLPKR-GPQAFDAFCEAL   89
ICErelIII      VKKDNHKKRTVKMLEY----LGKDVLHGVFNYLAKHDVITLKEEEKKYYDAKIEDKALILVDSLR-KNRVAHQM----   112
Tx/Ich2/ICErelII MAEGNHRKKPLKVLES----LGKDFLHGVIDNLVEQNVLNWKEEEKKYYDAKIEDKVRVMADSMQEKQRMAGQM----   71
ICE            MADKVLKEKRKLFIRS----MGEGTINGLLDELIQTRVLNKEEMEKVKREMATVMDKTRALIDSVIPKGAQACQICITY   75

1st MORT module                    2nd MORT module
MACH α1        ELLFRINRLDLLITYLNTRKEEMERELQTPGRAQISAYRVMLYQISEEVSRSELRSFKFLLQEEISKCKLDDDMNLLDIF   143
MACH β1        ELLFRINRLDLLITYLNTRKEEMERELQTPGRAQISAYRVMLYQISEEVSRSELRSFKFLLQEEISKCKLDDDMNLLDIF   143
MACH β3        ELLFRINRLDLLITYLNTRKEEMERELQTPGRAQISAYRVMLYQISEEVSRSELRSFKFLLQEEISKCKLDDDMNLLDIF   143

CED-3          RSTGHEGIAEVLEPLARSVDSNAVEFECPMSPASH-RRSRALSPAGYTSPTRVHRDSVSVSVSSFTSYQDIYSRARSRSRS   155
Ich-11/Nedd2   RETKQGHLEDMLTTLSGLQHVLPPLSCDYDLSLPFPVCESCPLYKKLRLSTDTV-------------LLQIEA------   144
ICErelIII      ----FTQTL---------LNMDQKITSVKP-----------------------------------------------   135
Tx/Ich2/ICErelII ----LLQIE---------FNIDQISPNKKA-----------------------------------HPNMEA------   94
ICE            ICEEDSYLAGTLGLSA-------------DQTSGNYLNMQDSQGVLSSFPAPQAVQDNP-----------------   121
                                                                              → P20

2nd MORT module              1st           2nd          3rd
                                                         ┌─block─┐    ┌─block─┐    ┌─block──
MACH α1        IEMEKRVILGEGKLDILKRVCAQINKSLLKIINDYEEFSKERSSSLEGSPDEFSNGEELCGVMTISDSPREQDSESQTLD   223
MACH β1        IEMEKRVILGEGKLDILKRVCAQINKSLLKIINDYEEFSKERSSSLEGSPDEFSNGEELCGVMTISDSPREQDSESQTLD   223
MACH β3        IEMEKRVILGEGKLDILKRVCAQINKSLLKIINDYEEFSKERSSSLEGSPDEFSNGEELCGVMTISDSPREQDSESQTLD   223

→ P17
CPP-32                              MENTENSVDSKSIKNLEPKIIHGSESMDS-GISLD    34
CED-3          RALHSSDRHNYSSPPVNAFPSQPSSANSSFTGCSSLGYSSSRNRSFSKASGPTQ-YIFHEEDMNFVDAPTIS--RVFDEK  232
Mcn2                                MSSASGLR-RGHPAGGEENMTETDAFYKREMFDPA    34
Ich-11/Nedd2   ----------------------------------EHSLDNKDGPVQLQVKPCTPEFYQTHF----------------Q  172
ICErelIII      ----------------------------GPPESAESTNILKIQPREEFLRLQKKNHDEI------------------  166
Tx/Ich2/ICErelII ----------------------------GPPESGESTDALKLCPHEEFLRLQKERAEEI------------------  125
ICE            ----------------------------AMPTSSGSEGNVKLCSLEEAQRIWKQKSAEI------------------  152
```

FIG. 11B

Vector

MACHα2

MACHα3

MACHα1(1-415)

Chimera (p55-Fas) + vector

Chimera (p55-Fas) + MACHα1(C360S)

P55-TNFR + vector p55-TNFR + MACHα1(C360S)

SEQUENCE LISTING (1) GENERAL INFORMATION:

(iii) NUMBER OF SEQUENCES: 34

(2) INFORMATION FOR SEQ ID NO: 1:

(i) SEQUENCE CHARACTERISTICS:
      (A) LENGTH: 1701 base pairs
      (B) TYPE: nucleic acid
      (C) STRANDEDNESS: single
      (D) TOPOLOGY: linear (ii) MOLECULE TYPE: cDNA -continued (ix) FEATURE:
    (A) NAME/KEY: CDS
    (B) LOCATION:1..768

(xi) SEQUENCE DESCRIPTION: SEQ ID NO: 1:

```
GTG AAT CAG GCA CCG GAG TGC AGG TTC GGG GGT GGA ATC CTT GGG CCG         48
Val Asn Gln Ala Pro Glu Cys Arg Phe Gly Gly Gly Ile Leu Gly Pro
 1               5                  10                  15

CTG GGC AAG CGG CGA GAC CTG GCC AGG GCC AGC GAG CCG AGG ACA GAG         96
Leu Gly Lys Arg Arg Asp Leu Ala Arg Ala Ser Glu Pro Arg Thr Glu
             20                  25                  30

GGC GCG CGG AGG GCC GGG CCG CAG CCC CGG CCG CTT GCA GAC CCC GCC        144
Gly Ala Arg Arg Ala Gly Pro Gln Pro Arg Pro Leu Ala Asp Pro Ala
         35                  40                  45

ATG GAC CCG TTC CTG GTG CTG CTG CAC TCG GTG TCG TCC AGC CTG TCG        192
Met Asp Pro Phe Leu Val Leu Leu His Ser Val Ser Ser Ser Leu Ser
     50                  55                  60

AGC AGC GAG CTG ACC GAG CTC AAG TTC CTA TGC CTC GGG CGC GTG GTC        240
Ser Ser Glu Leu Thr Glu Leu Lys Phe Leu Cys Leu Gly Arg Val Val
 65                  70                  75                  80

AAG CGC AAG CTG GAG CGC GTG CAG AGC GGC CTA GAC CTC TTC TCC ATG        288
Lys Arg Lys Leu Glu Arg Val Gln Ser Gly Leu Asp Leu Phe Ser Met
                 85                  90                  95

CTG CTG GAG CAG AAC GAC CTG GAG CCC GGG CAC ACC GAG CTC CTG CGC        336
Leu Leu Glu Gln Asn Asp Leu Glu Pro Gly His Thr Glu Leu Leu Arg
            100                 105                 110

GAG CTG CTC GCC TCC CTG CGG CGC CAC GAC CTG CTG CGG CGC GTC GAC        384
Glu Leu Leu Ala Ser Leu Arg Arg His Asp Leu Leu Arg Arg Val Asp
        115                 120                 125

GAC TTC GAG GCG GGG GCG GCG GCC GGG GCC GCG CCT GGG GAA GAA GAC        432
Asp Phe Glu Ala Gly Ala Ala Ala Gly Ala Ala Pro Gly Glu Glu Asp
    130                 135                 140

CTG TGT GCA GCA TTT AAC GTC ATA TGT GAT AAT GTG GGG AAA GAT TGG        480
Leu Cys Ala Ala Phe Asn Val Ile Cys Asp Asn Val Gly Lys Asp Trp
145                 150                 155                 160

AGA AGG CTG GCT CGT CAG CTC AAA GTC TCA GAC ACC AAG ATC GAC AGC        528
Arg Arg Leu Ala Arg Gln Leu Lys Val Ser Asp Thr Lys Ile Asp Ser
                165                 170                 175

ATC GAG GAC AGA TAC CCC CGC AAC CTG ACA GAG CGT GTG CGG GAG TCA        576
Ile Glu Asp Arg Tyr Pro Arg Asn Leu Thr Glu Arg Val Arg Glu Ser
            180                 185                 190

CTG AGA ATC TGG AAG AAC ACA GAG AAG GAG AAC GCA ACA GTG GCC CAC        624
Leu Arg Ile Trp Lys Asn Thr Glu Lys Glu Asn Ala Thr Val Ala His
        195                 200                 205

CTG GTG GGG GCT CTC AGG TCC TGC CAG ATG AAC CTG GTG GCT GAC CTG        672
Leu Val Gly Ala Leu Arg Ser Cys Gln Met Asn Leu Val Ala Asp Leu
    210                 215                 220

GTA CAA GAG GTT CAG CAG GCC CGT GAC CTC CAG AAC AGG AGT GGG GCC        720
Val Gln Glu Val Gln Gln Ala Arg Asp Leu Gln Asn Arg Ser Gly Ala
225                 230                 235                 240

ATG TCC CCG ATG TCA TGG AAC TCA GAC GCA TCT ACC TCC GAA GCG TCC        768
Met Ser Pro Met Ser Trp Asn Ser Asp Ala Ser Thr Ser Glu Ala Ser
                245                 250                 255

TGATGGGCCG CTGCTTTGCG CTGGTGGACC ACAGGCATCT ACACAGCCTG GACTTTGGTT       828

CTCTCCAGGA AGGTAGCCCA GCACTGTGAA GACCCAGCAG GAAGCCAGGC TGAGTGAGCC       888

ACAGACCACC TGCTTCTGAA CTCAAGCTGC GTTTATTAAT GCCTCTCCCG CACCAGGCCG       948

GGCTTGGGCC CTGCACAGAT ATTTCCATTT CTTCCTCACT ATGACACTGA GCAAGATCTT      1008

GTCTCCACTA AATGAGCTCC TGCGGGAGTA GTTGGAAAGT TGGAACCGTG TCCAGCACAG      1068
```

```
AAGGAATCTG TGCAGATGAG CAGTCACACT GTTACTCCAC AGCGGAGGAG ACCAGCTCAG    1128

AGGCCCAGGA ATCGGAGCGA AGCAGAGAGG TGGAGAACTG GGATTTGAAC CCCCGCCATC    1188

CTTCACCAGA GCCCATGCTC AACCACTGTG GCGTTCTGCT GCCCCTGCAG TTGGCAGAAA    1248

GGATGTTTTT GTCCCATTTC CTTGGAGGCC ACCGGACAG  ACCTGGACAC TAGGGTCAGG    1308

CGGGGTGCTG TGGTGGGGAG AGGCATGGCT GGGGTGGGGG TGGGGAGACC TGGTTGGCCG    1368

TGGTCCAGCT CTTGGCCCCT GTGTGAGTTG AGTCTCCTCT CTGAGACTGC TAAGTAGGGG    1428

CAGTGATGGT TGCCAGGACG AATTGAGATA ATATCTGTGA GGTGCTGATG AGTGATTGAC    1488

ACACAGCACT CTCTAAATCT TCCTTGTGAG GATTATGGGT CCTGCAATTC TACAGTTTCT    1548

TACTGTTTTG TATCAAAATC ACTATCTTTC TGATAACAGA ATTGCCAAGG CAGCGGGATC    1608

TCGTATCTTT AAAAAGCAGT CCTCTTATTC CTAAGGTAAT CCTATTAAAA CACAGCTTTA    1668

CAACTTCCAT ATTACAAAAA AAAAAAAAAA AAA                                 1701
```

(2) INFORMATION FOR SEQ ID NO: 2:

(i) SEQUENCE CHARACTERISTICS:
        (A) LENGTH: 256 amino acids
        (B) TYPE: amino acid
        (D) TOPOLOGY: linear (ii) MOLECULE TYPE: protein (xi) SEQUENCE DESCRIPTION: SEQ ID NO: 2:

```
Val Asn Gln Ala Pro Glu Cys Arg Phe Gly Gly Gly Ile Leu Gly Pro
 1               5                  10                  15

Leu Gly Lys Arg Arg Asp Leu Ala Arg Ala Ser Glu Pro Arg Thr Glu
            20                  25                  30

Gly Ala Arg Ala Gly Pro Gln Pro Arg Pro Leu Ala Asp Pro Ala
        35                  40                  45

Met Asp Pro Phe Leu Val Leu Leu His Ser Val Ser Ser Leu Ser
 50                  55                  60

Ser Ser Glu Leu Thr Glu Leu Lys Phe Leu Cys Leu Gly Arg Val Val
65                  70                  75                  80

Lys Arg Lys Leu Glu Arg Val Gln Ser Gly Leu Asp Leu Phe Ser Met
                85                  90                  95

Leu Leu Glu Gln Asn Asp Leu Glu Pro Gly His Thr Glu Leu Leu Arg
            100                 105                 110

Glu Leu Leu Ala Ser Leu Arg Arg His Asp Leu Arg Arg Val Asp
        115                 120                 125

Asp Phe Glu Ala Gly Ala Ala Gly Ala Ala Pro Gly Glu Glu Asp
130                 135                 140

Leu Cys Ala Ala Phe Asn Val Ile Cys Asp Asn Val Gly Lys Asp Trp
145                 150                 155                 160

Arg Arg Leu Ala Arg Gln Leu Lys Val Ser Asp Thr Lys Ile Asp Ser
                165                 170                 175

Ile Glu Asp Arg Tyr Pro Arg Asn Leu Thr Glu Arg Val Arg Glu Ser
            180                 185                 190

Leu Arg Ile Trp Lys Asn Thr Glu Lys Glu Asn Ala Thr Val Ala His
        195                 200                 205

Leu Val Gly Ala Leu Arg Ser Cys Gln Met Asn Leu Val Ala Asp Leu
    210                 215                 220

Val Gln Glu Val Gln Gln Ala Arg Asp Leu Gln Asn Arg Ser Gly Ala
225                 230                 235                 240
```

```
Met Ser Pro Met Ser Trp Asn Ser Asp Ala Ser Thr Ser Glu Ala Ser
            245                 250                 255
```

(2) INFORMATION FOR SEQ ID NO: 3:

(i) SEQUENCE CHARACTERISTICS:
        (A) LENGTH: 200 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 3:

```
CCGCCGCCGC CGCCGCCACC TGCCCAGACT TTTCTGTTCC AGGGTCAGCC TGTAGTGAAT      60
CGGCCGCTGA GCCTGAAGGA CCAACAGACG TTCGCGCGCT CTGTGGGTCT CAAATGGCGC     120
AAGGTGGGGC GCTCACTGCA GCGAGGCTGC CGGGCGCTGC GGGACCCGGC GCTGGACTCG     180
CTGGCCTACG AGTACGAGCG                                                 200
```

(2) INFORMATION FOR SEQ ID NO: 4:

(i) SEQUENCE CHARACTERISTICS:
        (A) LENGTH: 1036 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 4:

```
CGAGGCCACG AAGGCCGGCT GCCTGAGGAA TACCAGTGGG CAAGAGAATT AGCATTTCTG      60
GAGCATCTGC TGTCTGAGCA GCCCCTGGGT GCGTCCACTT TCTGGGCACG TGAGGTTGGG     120
CCTTGGCCGC CTGAGCCCTT GAGTTGGTCA CTTGAACCTT GGGAATATTG AGATTATATT     180
CTCCTGCCTT TTAAAAAGAT GGACTTCAGC AGAAATCTTT ATGATATTGG GGAACAACTG     240
GACAGTGAAG ATCTGGCCTC CCTCAAGTTC CTGAGCCTGG ACTACATTCC GCAAAGGAAG     300
CAAGAACCCA TCAAGGATGC CTTGATGTTA TTCCAGAGAC TCCAGGAAAA GAGAATGTTG     360
GAGGAAAGCA ATCTGTCCTT CCTGAAGGAG CTGCTCTTCC GAATTAATAG ACTGGATTTG     420
CTGATTACCT ACCTAAACAC TAGAAAGGAG GAGATGGAAA GGGAACTTCA GACACCAGGC     480
AGGGCTCAAA TTTCTGCCTA CAGGGTCATG CTCTATCAGA TTTCAGAAGA AGTGAGCAGA     540
TCAGAATTGA GGTCTTTTAA GTTTCTTTTG CAAGAGGAAA TCTCCAAATG CAAACTGGAT     600
GATGACATGA ACCTGCTGGA TATTTTCATA GAGATGGAGA AGAGGGTCAT CCTGGGAGAA     660
GGAAAGTTGG ACATCCTGAA AAGAGTCTGT GCCCAAATCA ACAAGAGCCT GCTGAAGATA     720
ATCAACGACT ATGAAGAATT CAGCAAAGAG AGAAGCAGCA GCCTTGAAGG AAGTCCTGAT     780
GAATTTTCAA ATGACTTTGG ACAAAGTTTA CCAAATGAAA AGCAAACCTC GGGGATACTG     840
TCTGATCATC AACAATCACA ATTTTGCAAA AGCACGGGAG AAAGTGCCCA AACTTCACAG     900
CATTAGGGAC AGGAATGGAA CACACTTGGA TGCAGGGTTT GAGAATGTTT TTAGCTGGTG     960
GCAATAAATA TTAGAAGCCT GCAGAATCCA GCTACGAATA TAGAGGGTTT TGCTCTTGGG    1020
CCTTCGTGGC CTCGAG                                                   1036
```

(2) INFORMATION FOR SEQ ID NO: 5:

(i) SEQUENCE CHARACTERISTICS:
        (A) LENGTH: 235 amino acids (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 5:

Met Asp Phe Ser Arg Asn Leu Tyr Asp Ile Gly Glu Gln Leu Asp Ser
1               5                  10                  15

Glu Asp Leu Ala Ser Leu Lys Phe Leu Ser Leu Asp Tyr Ile Pro Gln
            20                  25                  30

Arg Lys Gln Glu Pro Ile Lys Asp Ala Leu Met Leu Phe Gln Arg Leu
        35                  40                  45

Gln Glu Lys Arg Met Leu Glu Glu Ser Asn Leu Ser Phe Leu Lys Glu
50                  55                  60

Leu Leu Phe Arg Ile Asn Arg Leu Asp Leu Leu Ile Thr Tyr Leu Asn
65                  70                  75                  80

Thr Arg Lys Glu Glu Met Glu Arg Glu Leu Gln Thr Pro Gly Arg Ala
            85                  90                  95

Gln Ile Ser Ala Tyr Arg Val Met Leu Tyr Gln Ile Ser Glu Glu Val
        100                 105                 110

Ser Arg Ser Glu Leu Arg Ser Phe Lys Phe Leu Leu Gln Glu Glu Ile
    115                 120                 125

Ser Lys Cys Lys Leu Asp Asp Asp Met Asn Leu Leu Asp Ile Phe Ile
130                 135                 140

Glu Met Glu Lys Arg Val Ile Leu Gly Glu Gly Lys Leu Asp Ile Leu
145                 150                 155                 160

Lys Arg Val Cys Ala Gln Ile Asn Lys Ser Leu Leu Lys Ile Ile Asn
            165                 170                 175

Asp Tyr Glu Glu Phe Ser Lys Glu Arg Ser Ser Ser Leu Glu Gly Ser
        180                 185                 190

Pro Asp Glu Phe Ser Asn Asp Phe Gly Gln Ser Leu Pro Asn Glu Lys
    195                 200                 205

Gln Thr Ser Gly Ile Leu Ser Asp His Gln Gly Ser Gln Phe Cys Lys
210                 215                 220

Ser Thr Gly Glu Ser Ala Gln Thr Ser Gln His
225                 230                 235

(2) INFORMATION FOR SEQ ID NO: 6:

(i) SEQUENCE CHARACTERISTICS:
            (A) LENGTH: 78 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 6:

Tyr Gly Thr Leu Phe Gln Asp Leu Thr Asn Asn Ile Thr Leu Glu Asp
1               5                  10                  15

Leu Glu Gln Leu Lys Ser Ala Cys Lys Glu Asp Ile Pro Ser Glu Lys
            20                  25                  30

Ser Glu Glu Ile Thr Thr Gly Ser Ala Trp Phe Ser Phe Leu Glu Ser
        35                  40                  45

His Asn Lys Leu Asp Lys Asp Asn Leu Ser Ile Ile Glu His Ile Phe
    50                  55                  60

Glu Ile Ser Arg Arg Pro Asp Leu Leu Thr Met Val Val Asp (2) INFORMATION FOR SEQ ID NO: 7:

(i) SEQUENCE CHARACTERISTICS:
        (A) LENGTH: 479 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 7:

```
Met Asp Phe Ser Arg Asn Leu Tyr Asp Ile Gly Glu Gln Leu Asp Ser
 1               5                  10                  15

Glu Asp Leu Ala Ser Leu Lys Phe Leu Ser Leu Asp Tyr Ile Pro Gln
            20                  25                  30

Arg Lys Gln Glu Pro Ile Lys Asp Ala Leu Met Leu Phe Gln Arg Leu
        35                  40                  45

Gln Glu Lys Arg Met Leu Glu Glu Ser Asn Leu Ser Phe Leu Lys Glu
    50                  55                  60

Leu Leu Phe Arg Ile Asn Arg Leu Asp Leu Leu Ile Thr Tyr Leu Asn
65                  70                  75                  80

Thr Arg Lys Glu Glu Met Glu Arg Glu Leu Gln Thr Pro Gly Arg Ala
                85                  90                  95

Gln Ile Ser Ala Tyr Arg Val Met Leu Tyr Gln Ile Ser Glu Glu Val
            100                 105                 110

Ser Arg Ser Glu Leu Arg Ser Phe Lys Phe Leu Leu Gln Glu Glu Ile
        115                 120                 125

Ser Lys Cys Lys Leu Asp Asp Asp Met Asn Leu Leu Asp Ile Phe Ile
    130                 135                 140

Glu Met Glu Lys Arg Val Ile Leu Gly Glu Gly Lys Leu Asp Ile Leu
145                 150                 155                 160

Lys Arg Val Cys Ala Gln Ile Asn Lys Ser Leu Leu Lys Ile Ile Asn
                165                 170                 175

Asp Tyr Glu Glu Phe Ser Lys Glu Arg Ser Ser Leu Glu Gly Ser
            180                 185                 190

Pro Asp Glu Phe Ser Asn Gly Glu Glu Leu Cys Gly Val Met Thr Ile
        195                 200                 205

Ser Asp Ser Pro Arg Glu Gln Asp Ser Glu Ser Gln Thr Leu Asp Lys
    210                 215                 220

Val Tyr Gln Met Lys Ser Lys Pro Arg Gly Tyr Cys Leu Ile Ile Asn
225                 230                 235                 240

Asn His Asn Phe Ala Lys Ala Arg Glu Lys Val Pro Lys Leu His Ser
                245                 250                 255

Ile Arg Asp Arg Asn Gly Thr His Leu Asp Ala Gly Ala Leu Thr Thr
            260                 265                 270

Thr Phe Glu Glu Leu His Phe Glu Ile Lys Pro His Asp Asp Cys Thr
        275                 280                 285

Val Glu Gln Ile Tyr Glu Ile Leu Lys Ile Tyr Gln Leu Met Asp His
    290                 295                 300

Ser Asn Met Asp Cys Phe Ile Cys Cys Ile Leu Ser His Gly Asp Lys
305                 310                 315                 320

Gly Ile Ile Tyr Gly Thr Asp Gly Gln Glu Ala Pro Ile Tyr Glu Leu
                325                 330                 335

Thr Ser Gln Phe Thr Gly Leu Lys Cys Pro Ser Leu Ala Gly Lys Pro
```

```
                  340                 345                 350
Lys Val Phe Phe Ile Gln Ala Cys Gln Gly Asp Asn Tyr Gln Lys Gly
                355                 360                 365
Ile Pro Val Glu Thr Asp Ser Glu Glu Gln Pro Tyr Leu Glu Met Asp
        370                 375                 380
Leu Ser Ser Pro Gln Thr Arg Tyr Ile Pro Asp Glu Ala Asp Phe Leu
385                 390                 395                 400
Leu Gly Met Ala Thr Val Asn Asn Cys Val Ser Tyr Arg Asn Pro Ala
                405                 410                 415
Glu Gly Thr Trp Tyr Ile Gln Ser Leu Cys Gln Ser Leu Arg Glu Arg
                420                 425                 430
Cys Pro Arg Gly Asp Asp Ile Leu Thr Ile Leu Thr Glu Val Asn Tyr
                435                 440                 445
Glu Val Ser Asn Lys Asp Asp Lys Lys Asn Met Gly Lys Gln Met Pro
                450                 455                 460
Gln Pro Thr Phe Thr Leu Arg Lys Lys Leu Val Phe Pro Ser Asp
465                 470                 475

(2) INFORMATION FOR SEQ ID NO: 8:

(i) SEQUENCE CHARACTERISTICS:
        (A) LENGTH: 277 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 8:

Met Asp Phe Ser Arg Asn Leu Tyr Asp Ile Gly Glu Gln Leu Asp Ser
1               5                   10                  15
Glu Asp Leu Ala Ser Leu Lys Phe Leu Ser Leu Asp Tyr Ile Pro Gln
                20                  25                  30
Arg Lys Gln Glu Pro Ile Lys Asp Ala Leu Met Leu Phe Gln Arg Leu
                35                  40                  45
Gln Glu Lys Arg Met Leu Glu Glu Ser Asn Leu Ser Phe Leu Lys Glu
        50                  55                  60
Leu Leu Phe Arg Ile Asn Arg Leu Asp Leu Leu Ile Thr Tyr Leu Asn
65                  70                  75                  80
Thr Arg Lys Glu Glu Met Glu Arg Glu Leu Gln Thr Pro Gly Arg Ala
                85                  90                  95
Gln Ile Ser Ala Tyr Arg Val Met Leu Tyr Gln Ile Ser Glu Glu Val
                100                 105                 110
Ser Arg Ser Glu Leu Arg Ser Phe Lys Phe Leu Leu Gln Glu Glu Ile
                115                 120                 125
Ser Lys Cys Lys Leu Asp Asp Asp Met Asn Leu Leu Asp Ile Phe Ile
        130                 135                 140
Glu Met Glu Lys Arg Val Ile Leu Gly Glu Gly Lys Leu Asp Ile Leu
145                 150                 155                 160
Lys Arg Val Cys Ala Gln Ile Asn Lys Ser Leu Leu Lys Ile Ile Asn
                165                 170                 175
Asp Tyr Glu Glu Phe Ser Lys Glu Arg Ser Ser Ser Leu Glu Gly Ser
                180                 185                 190
Pro Asp Glu Phe Ser Asn Gly Glu Glu Leu Cys Gly Val Met Thr Ile
                195                 200                 205
Ser Asp Ser Pro Arg Glu Gln Asp Ser Glu Ser Gln Thr Leu Asp Lys
```

```
                  210                 215                 220
Val Tyr Gln Met Lys Ser Lys Pro Arg Gly Tyr Cys Leu Ile Ile Asn
225                 230                 235                 240

Asn His Asn Phe Ala Lys Ala Arg Glu Lys Val Pro Lys Leu His Ser
                245                 250                 255

Ile Arg Asp Arg Asn Gly Thr His Leu Asp Ala Gly Phe Gly Asn Val
                260                 265                 270

Phe Ser Trp Trp Gln
            275

(2) INFORMATION FOR SEQ ID NO: 9:

(i) SEQUENCE CHARACTERISTICS:
        (A) LENGTH: 489 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 9:

Met Met Phe Ser Ser His Leu Lys Val Asp Glu Ile Leu Glu Val Leu
1               5                   10                  15

Ile Ala Lys Gln Val Leu Asn Ser Asp Asn Gly Asp Met Ile Asn Ser
                20                  25                  30

Cys Gly Thr Val Arg Glu Lys Arg Glu Ile Val Lys Ala Val Gln
                35                  40                  45

Arg Arg Gly Asp Val Ala Phe Asp Ala Phe Tyr Asp Ala Leu Arg Ser
50                  55                  60

Thr Gly His Glu Gly Leu Ala Glu Val Leu Glu Pro Leu Ala Arg Ser
65                  70                  75                  80

Val Asp Ser Asn Ala Val Glu Phe Glu Cys Pro Met Ser Pro Ala Ser
                85                  90                  95

His Arg Arg Ser Arg Ala Leu Ser Pro Ala Gly Tyr Thr Ser Pro Thr
                100                 105                 110

Arg Val His Arg Asp Ser Val Ser Ser Val Ser Ser Phe Thr Ser Tyr
                115                 120                 125

Gln Asp Ile Tyr Ser Arg Ala Arg Ser Arg Ser Arg Ser Arg Ala Leu
                130                 135                 140

His Ser Ser Asp Arg His Asn Tyr Ser Ser Pro Val Asn Ala Phe
145                 150                 155                 160

Pro Ser Gln Pro Ser Ser Ala Asn Ser Ser Phe Thr Gly Cys Ser Ser
                165                 170                 175

Leu Gly Tyr Ser Ser Arg Asn Arg Ser Phe Ser Lys Ala Ser Gly
                180                 185                 190

Pro Thr Gln Tyr Ile Phe His Glu Glu Asp Met Asn Phe Val Asp Ala
                195                 200                 205

Pro Thr Ile Ser Arg Val Phe Asp Glu Lys Thr Met Tyr Arg Asn Phe
                210                 215                 220

Ser Ser Pro Arg Gly Met Cys Leu Ile Ile Asn Asn Glu His Phe Glu
225                 230                 235                 240

Gln Met Pro Thr Arg Asn Gly Thr Lys Ala Asp Lys Asp Asn Leu Thr
                245                 250                 255

Asn Leu Phe Arg Cys Met Gly Tyr Thr Val Ile Cys Lys Asp Asn Leu
                260                 265                 270

Thr Gly Arg Gly Met Leu Leu Thr Ile Arg Asp Phe Ala Lys His Glu
```

-continued

```
                275                 280                 285
Ser His Gly Asp Ser Ala Ile Leu Val Ile Leu Ser His Gly Glu Glu
    290                 295                 300
Asn Val Ile Ile Gly Val Asp Asp Ile Pro Ile Ser Thr His Glu Ile
305                 310                 315                 320
Tyr Asp Leu Leu Asn Ala Ala Asn Ala Pro Arg Leu Ala Asn Lys Pro
                325                 330                 335
Lys Ile Val Phe Val Gln Ala Cys Arg Gly Glu Arg Arg Asp Asn Gly
                340                 345                 350
Phe Pro Val Leu Asp Ser Val Asp Gly Val Pro Ala Phe Leu Arg Arg
                355                 360                 365
Gly Trp Asp Asn Arg Asp Gly Pro Leu Phe Asn Phe Leu Gly Cys Val
    370                 375                 380
Arg Pro Gln Val Gln Gln Val Trp Arg Lys Lys Pro Ser Gln Ala Asp
385                 390                 395                 400
Ile Leu Ile Arg Tyr Ala Thr Thr Ala Gln Tyr Val Ser Trp Arg Asn
                405                 410                 415
Ser Ala Arg Gly Ser Trp Phe Ile Gln Ala Val Cys Glu Val Phe Ser
                420                 425                 430
Thr His Ala Lys Asp Met Asp Val Val Glu Leu Leu Thr Glu Val Asn
                435                 440                 445
Lys Lys Val Ala Cys Gly Phe Gln Thr Ser Gln Gly Ser Asn Ile Leu
                450                 455                 460
Lys Gln Met Pro Glu Met Thr Ser Arg Leu Leu Lys Lys Phe Tyr Phe
465                 470                 475                 480
Trp Pro Glu Ala Arg Asn Ser Ala Val
                485

(2) INFORMATION FOR SEQ ID NO: 10:

(i) SEQUENCE CHARACTERISTICS:
        (A) LENGTH: 421 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 10:

Met His Pro His His Gln Glu Thr Leu Lys Lys Asn Arg Val Val Leu
1               5                   10                  15
Ala Lys Gln Leu Leu Leu Ser Glu Leu Glu His Leu Leu Glu Lys
                20                  25                  30
Asp Ile Ile Thr Leu Glu Met Arg Glu Leu Ile Gln Ala Lys Val Gly
                35                  40                  45
Ser Phe Ser Gln Asn Val Glu Leu Leu Asn Leu Leu Pro Lys Arg Gly
                50                  55                  60
Pro Gln Ala Phe Asp Ala Phe Cys Glu Ala Leu Arg Glu Thr Lys Gln
65              70                  75                  80
Gly His Leu Glu Asp Met Leu Leu Thr Thr Leu Ser Gly Leu Gln His
                85                  90                  95
Val Leu Pro Pro Leu Ser Cys Asp Tyr Asp Leu Ser Leu Pro Phe Pro
                100                 105                 110
Val Cys Glu Ser Cys Pro Leu Tyr Lys Lys Leu Arg Leu Ser Thr Asp
                115                 120                 125
Thr Val Glu His Ser Leu Asp Asn Lys Asp Gly Pro Val Cys Leu Gln
```

```
            130                 135                 140
Val Lys Pro Cys Thr Pro Glu Phe Tyr Gln Thr His Phe Gln Leu Ala
145                 150                 155                 160

Tyr Arg Leu Gln Ser Arg Pro Arg Gly Leu Ala Leu Val Leu Ser Asn
                165                 170                 175

Val His Phe Thr Gly Glu Lys Glu Leu Glu Phe Arg Ser Gly Gly Asp
                180                 185                 190

Val Asp His Ser Thr Leu Val Thr Leu Phe Lys Leu Leu Gly Tyr Asp
                195                 200                 205

Val His Val Leu Cys Asp Gln Thr Ala Gln Glu Met Gln Glu Lys Leu
            210                 215                 220

Gln Asn Phe Ala Gln Leu Pro Ala His Arg Val Thr Asp Ser Cys Ile
225                 230                 235                 240

Val Ala Leu Leu Ser His Gly Val Glu Gly Ala Ile Tyr Gly Val Asp
                245                 250                 255

Gly Lys Leu Leu Gln Leu Gln Glu Val Phe Gln Leu Phe Asp Asn Ala
                260                 265                 270

Asn Cys Pro Ser Leu Gln Asn Lys Pro Lys Met Phe Phe Ile Gln Ala
            275                 280                 285

Cys Arg Gly Asp Glu Thr Asp Arg Gly Val Asp Gln Gln Asp Gly Lys
                290                 295                 300

Asn His Ala Gly Ser Pro Gly Cys Glu Glu Ser Asp Ala Gly Lys Glu
305                 310                 315                 320

Lys Leu Pro Lys Met Arg Leu Pro Thr Arg Ser Asp Met Ile Cys Gly
                325                 330                 335

Tyr Ala Cys Leu Lys Gly Thr Ala Ala Met Arg Asn Thr Lys Arg Gly
                340                 345                 350

Ser Trp Tyr Ile Glu Ala Leu Ala Gln Val Phe Ser Glu Arg Ala Cys
            355                 360                 365

Asp Met His Val Ala Asp Met Leu Val Lys Val Asn Ala Leu Ile Lys
            370                 375                 380

Asp Arg Glu Gly Tyr Ala Pro Gly Thr Glu Phe His Arg Cys Lys Glu
385                 390                 395                 400

Met Ser Glu Tyr Cys Ser Thr Leu Cys Arg His Leu Tyr Leu Phe Pro
                405                 410                 415

Gly His Pro Pro Thr
            420

(2) INFORMATION FOR SEQ ID NO: 11:

(i) SEQUENCE CHARACTERISTICS:
        (A) LENGTH: 376 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 11:

Val Lys Lys Asp Asn His Lys Lys Thr Val Lys Met Leu Glu Tyr
1               5                   10                  15

Leu Gly Lys Asp Val Leu His Gly Val Phe Asn Tyr Leu Ala Lys His
                20                  25                  30

Asp Val Leu Thr Leu Lys Glu Glu Lys Lys Tyr Tyr Asp Ala
            35                  40                  45

Lys Ile Glu Asp Lys Ala Leu Ile Leu Val Asp Ser Leu Arg Lys Asn
```

```
                50                  55                  60
Arg Val Ala His Gln Met Phe Thr Gln Thr Leu Leu Asn Met Asp Gln
 65                  70                  75                  80

Lys Ile Thr Ser Val Lys Pro Leu Leu Gln Ile Glu Ala Gly Pro Pro
                 85                  90                  95

Glu Ser Ala Glu Ser Thr Asn Ile Leu Lys Leu Cys Pro Arg Glu Glu
            100                 105                 110

Phe Leu Arg Leu Cys Lys Lys Asn His Asp Glu Ile Tyr Pro Ile Lys
            115                 120                 125

Lys Arg Glu Asp Arg Arg Leu Ala Leu Ile Ile Cys Asn Thr Lys
130                 135                 140

Phe Asp His Leu Pro Ala Arg Asn Gly Ala His Tyr Asp Ile Val Gly
145                 150                 155                 160

Met Lys Arg Leu Leu Gln Gly Leu Gly Tyr Thr Val Val Asp Glu Lys
                165                 170                 175

Asn Leu Thr Ala Arg Asp Met Glu Ser Val Leu Arg Ala Phe Ala Ala
            180                 185                 190

Arg Pro Glu His Lys Ser Ser Asp Ser Thr Phe Leu Val Leu Met Ser
            195                 200                 205

His Gly Ile Leu Glu Gly Ile Cys Gly Thr Ala His Lys Lys Lys Lys
210                 215                 220

Pro Asp Val Leu Leu Tyr Asp Thr Ile Phe Gln Ile Phe Asn Asn Arg
225                 230                 235                 240

Asn Cys Leu Ser Leu Lys Asp Lys Pro Lys Val Ile Ile Val Gln Ala
                245                 250                 255

Cys Arg Gly Glu Lys His Gly Glu Leu Trp Val Arg Asp Ser Pro Ala
            260                 265                 270

Ser Leu Ala Val Ile Ser Ser Gln Ser Ser Glu Asn Leu Glu Ala Asp
            275                 280                 285

Ser Val Cys Lys Ile His Glu Glu Lys Asp Phe Ile Ala Phe Cys Ser
            290                 295                 300

Ser Thr Pro His Asn Val Ser Trp Arg Asp Arg Thr Arg Gly Ser Ile
305                 310                 315                 320

Phe Ile Thr Glu Leu Ile Thr Cys Phe Gln Lys Tyr Ser Cys Cys Cys
                325                 330                 335

His Leu Met Glu Ile Phe Arg Lys Val Gln Lys Ser Phe Glu Val Pro
            340                 345                 350

Gln Ala Lys Ala Gln Met Pro Thr Ile Glu Arg Ala Thr Leu Thr Arg
            355                 360                 365

Asp Phe Tyr Leu Phe Pro Gly Asn
370                 375

(2) INFORMATION FOR SEQ ID NO: 12:

(i) SEQUENCE CHARACTERISTICS:
        (A) LENGTH: 377 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 12:

Met Ala Glu Gly Asn His Arg Lys Lys Pro Leu Lys Val Leu Glu Ser
  1               5                  10                  15

Leu Gly Lys Asp Phe Leu Thr Gly Val Leu Asp Asn Leu Val Glu Gln
```

```
                20                  25                  30
Asn Val Leu Asn Trp Lys Glu Glu Lys Lys Tyr Tyr Asp Ala
            35                  40                  45
Lys Thr Glu Asp Lys Val Arg Val Met Ala Asp Ser Met Gln Glu Lys
50                  55                  60
Gln Arg Met Ala Gly Gln Met Leu Leu Gln Thr Phe Phe Asn Ile Asp
65                  70                  75                  80
Gln Ile Ser Pro Asn Lys Lys Ala His Pro Asn Met Glu Ala Gly Pro
                85                  90                  95
Pro Glu Ser Gly Glu Ser Thr Asp Ala Leu Lys Leu Cys Pro His Glu
            100                 105                 110
Glu Phe Leu Arg Leu Cys Lys Glu Arg Ala Glu Glu Ile Tyr Pro Ile
            115                 120                 125
Lys Glu Arg Asn Asn Arg Thr Arg Leu Ala Leu Ile Ile Cys Asn Thr
            130                 135                 140
Glu Phe Asp His Leu Pro Pro Arg Asn Gly Ala Asp Phe Asp Ile Thr
145                 150                 155                 160
Gly Met Lys Glu Leu Leu Glu Gly Leu Asp Tyr Ser Val Asp Val Glu
                165                 170                 175
Glu Asn Leu Thr Ala Arg Asp Met Glu Ser Ala Leu Arg Ala Phe Ala
            180                 185                 190
Thr Arg Pro Glu His Lys Ser Ser Asp Ser Thr Phe Leu Val Leu Met
            195                 200                 205
Ser His Gly Ile Leu Glu Gly Ile Cys Gly Thr Val His Asp Glu Lys
            210                 215                 220
Lys Pro Asp Val Leu Leu Tyr Asp Thr Ile Phe Gln Ile Phe Asn Asn
225                 230                 235                 240
Arg Asn Cys Leu Ser Leu Lys Asp Lys Pro Lys Val Ile Ile Val Gln
                245                 250                 255
Ala Cys Arg Gly Ala Asn Arg Gly Glu Leu Trp Val Arg Asp Ser Pro
                260                 265                 270
Ala Ser Leu Glu Val Ala Ser Ser Gln Ser Ser Glu Asn Leu Glu Glu
            275                 280                 285
Asp Ala Val Tyr Lys Thr His Val Glu Lys Asp Phe Ile Ala Phe Cys
            290                 295                 300
Ser Ser Thr Pro His Asn Val Ser Trp Arg Asp Ser Thr Met Gly Ser
305                 310                 315                 320
Ile Phe Ile Thr Gln Leu Ile Thr Cys Phe Gln Lys Tyr Ser Trp Cys
                325                 330                 335
Cys His Leu Glu Glu Val Phe Arg Lys Val Gln Gln Ser Phe Glu Thr
            340                 345                 350
Pro Arg Ala Lys Ala Gln Met Pro Thr Ile Glu Arg Leu Ser Met Thr
            355                 360                 365
Arg Tyr Phe Tyr Leu Phe Pro Gly Asn
            370                 375
```

(2) INFORMATION FOR SEQ ID NO: 13:

(i) SEQUENCE CHARACTERISTICS:
        (A) LENGTH: 404 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 13:

```
Met Ala Asp Lys Val Leu Lys Glu Lys Arg Lys Leu Phe Ile Arg Ser
1               5                   10                  15

Met Gly Glu Gly Thr Ile Asn Gly Leu Leu Asp Glu Leu Leu Gln Thr
            20                  25                  30

Arg Val Leu Asn Lys Glu Glu Met Glu Lys Val Lys Arg Glu Asn Ala
                35                  40                  45

Thr Val Met Asp Lys Thr Arg Ala Leu Ile Asp Ser Val Ile Pro Lys
50                  55                  60

Gly Ala Gln Ala Cys Gln Ile Cys Ile Thr Tyr Ile Cys Glu Glu Asp
65                  70                  75                  80

Ser Tyr Leu Ala Gly Thr Leu Gly Leu Ser Ala Asp Gln Thr Ser Gly
                85                  90                  95

Asn Tyr Leu Asn Met Gln Asp Ser Gln Gly Val Leu Ser Ser Phe Pro
            100                 105                 110

Ala Pro Gln Ala Val Gln Asp Asn Pro Ala Met Pro Thr Ser Ser Gly
        115                 120                 125

Ser Glu Gly Asn Val Lys Leu Cys Ser Leu Glu Glu Ala Gln Arg Ile
    130                 135                 140

Trp Lys Gln Lys Ser Ala Glu Ile Tyr Pro Ile Met Asp Lys Ser Ser
145                 150                 155                 160

Arg Thr Arg Leu Ala Leu Ile Ile Cys Asn Glu Glu Phe Asp Ser Ile
                165                 170                 175

Pro Arg Arg Thr Gly Ala Glu Val Asp Ile Thr Gly Met Thr Met Leu
            180                 185                 190

Leu Gln Asn Leu Gly Tyr Ser Val Asp Val Lys Lys Asn Leu Thr Ala
        195                 200                 205

Ser Asp Met Thr Thr Glu Leu Glu Ala Phe Ala His Arg Pro Glu His
    210                 215                 220

Lys Thr Ser Asp Ser Thr Phe Leu Val Phe Met Ser His Gly Ile Arg
225                 230                 235                 240

Glu Gly Ile Cys Gly Lys Lys His Ser Glu Gln Val Pro Asp Ile Leu
                245                 250                 255

Gln Leu Asn Ala Ile Phe Asn Met Leu Asn Thr Lys Asn Cys Pro Ser
            260                 265                 270

Leu Lys Asp Lys Pro Lys Val Ile Ile Ile Gln Ala Cys Arg Gly Asp
        275                 280                 285

Ser Pro Gly Val Val Trp Phe Lys Asp Ser Val Gly Val Ser Gly Asn
    290                 295                 300

Leu Ser Leu Pro Thr Thr Glu Glu Phe Glu Asp Asp Ala Ile Lys Lys
305                 310                 315                 320

Ala His Ile Glu Lys Asp Phe Ile Ala Phe Cys Ser Ser Thr Pro Asp
                325                 330                 335

Asn Val Ser Trp Arg His Pro Thr Met Gly Ser Val Phe Ile Gly Arg
            340                 345                 350

Leu Ile Glu His Met Gln Glu Tyr Ala Cys Ser Cys Asp Val Glu Glu
        355                 360                 365

Ile Phe Arg Lys Val Arg Phe Ser Phe Glu Gln Pro Asp Gly Arg Ala
    370                 375                 380

Gln Met Pro Thr Thr Glu Arg Val Thr Leu Thr Arg Cys Phe Tyr Leu
385                 390                 395                 400

Phe Pro Gly His
```

(2) INFORMATION FOR SEQ ID NO: 14:

(i) SEQUENCE CHARACTERISTICS:
        (A) LENGTH: 2887 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 14:

```
GATTCTGCCT TTCTGCTGGA GGGAAGTGTT TTCACAGGTT CTCCTCCTTT TATCTTTTGT    60

GTTTTTTTTC AAGCCCTGCT GAATTTGCTA GTCAACTCAA CAGGAAGTGA GGCCATGGAG   120

GGAGGCAGAA GAGCCAGGGT GGTTATTGAA AGTAGAAGAA ACTTCTTCCT GGGAGCCTTT   180

CCCACCCCCT TCCCTGCTGA GCACGTGGAG TTAGGCAGGT TAGGGGACTC GGAGACTGCG   240

ATGGTGCCAG GAAAGGGTGG AGCGGATTAT ATTCTCCTGC CTTTTAAAAA GATGGACTTC   300

AGCAGAAATC TTTATGATAT TGGGGAACAA CTGGACAGTG AAGATCTGGC CTCCCTCAAG   360

TTCCTGAGCC TGGACTACAT TCCGCAAAGG AAGCAAGAAC CCATCAAGGA TGCCTTGATG   420

TTATTCCAGA GACTCCAGGA AAAGAGAATG TTGGAGGAAA GCAATCTGTC CTTCCTGAAG   480

GAGCTGCTCT TCCGAATTAA TAGACTGGAT TTGCTGATTA CCTACCTAAA CACTAGAAAG   540

GAGGAGATGG AAAGGGAACT TCAGACACCA GGCAGGGCTC AAATTTCTGC CTACAGGGTC   600

ATGCTCTATC AGATTTCAGA AGAAGTGAGC AGATCAGAAT TGAGGTCTTT TAAGTTTCTT   660

TTGCAAGAGG AAATCTCCAA ATGCAAACTG GATGATGACA TGAACCTGCT GGATATTTTC   720

ATAGAGATGG AGAAGAGGGT CATCCTGGGA GAAGGAAAGT TGGACATCCT GAAAAGAGTC   780

TGTGCCCAAA TCAACAAGAG CCTGCTGAAG ATAATCAACG ACTATGAAGA ATTCAGCAAA   840

GAGAGAAGCA GCAGCCTTGA AGGAAGTCCT GATGAATTTT CAAATGGGGA GGAGTTGTGT   900

GGGGTAATGA CAATCTCGGA CTCTCCAAGA GAACAGGATA GTGAATCACA GACTTTGGAC   960

AAAGTTTACC AAATGAAAAG CAAACCTCGG GGATACTGTC TGATCATCAA CAATCACAAT  1020

TTTGCAAAAG CACGGGAGAA AGTGCCCAAA CTTCACAGCA TTAGGGACAG GAATGGAACA  1080

CACTTGGATG CAGGGGCTTT GACCACGACC TTTGAAGAGC TTCATTTTGA GATCAAGCCC  1140

CACGATGACT GCACAGTAGA GCAAATCTAT GAGATTTTGA AAATCTACCA ACTCATGGAC  1200

CACAGTAACA TGGACTGCTT CATCTGCTGT ATCCTCTCCC ATGGAGACAA AGGCATCATC  1260

TATGGCACTG ATGGACAGGA GGCCCCCATC TATGAGCTGA CATCTCAGTT CACTGGTTTG  1320

AAGTGCCCTT CCCTTGCTGG AAAACCCAAA GTGTTTTTTA TTCAGGCTTG TCAGGGGGAT  1380

AACTACCAGA AAGGTATACC TGTTGAGACT GATTCAGAGG AGCAACCCTA TTTAGAAATG  1440

GATTTATCAT CACCTCAAAC GAGATATATC CCGGATGAGG CTGACTTTCT GCTGGGGATG  1500

GCCACTGTGA ATAACTGTGT TCCTACCGA AACCCTGCAG AGGGAACCTG GTACATCCAG   1560

TCACTTTGCC AGAGCCTGAG AGAGCGATGT CCTCGAGGCG ATGATATTCT CACCATCCTG  1620

ACTGAAGTGA ACTATGAAGT AAGCAACAAG GATGACAAGA AAAACATGGG GAAACAGATG  1680

CCTCAGCCTA CTTTCACACT AAGAAAAAAA CTTGTCTTCC CTTCTGATTG ATGGTGCTAT  1740

TTTGTTTGTT TTGTTTTGTT TTGTTTTTTT GAGACAGAAT CTCGCTCTGT CGCCCAGGCT  1800

GGAGTGCAGT GGCGTGATCT CGGCTCACCG CAAGCTCCGC CTCCCGGGTT CACGCCATTC  1860

TCCTGCCTCA GCCTCCCGAG TAGCTGGGAC TACAGGGGCC CGCCACCACA CCTGGCTAAT  1920

TTTTTAAAAA TATTTTTAGT AGAGACAGGG TTTCACTGTG TTAGCCAGGG TGGTCTTGAT  1980
```

```
CTCCTGACCT CGTGATCCAC CCACCTCGGC CTCCCAAAGT GCTGGGATTA CAGGCGTGAG    2040

CCACCGCGCC TGGCCGATGG TACTATTTAG ATATAACACT ATGTTTATTT ACTAATTTTC    2100

TAGATTTTCT ACTTTATTAA TTGTTTTGCA CTTTTTTATA AGAGCTAAAG TTAAATAGGA    2160

TATTAACAAC AATAACACTG TCTCCTTTCT CTTACGCTTA AGGCTTTGGG AATGTTTTTA    2220

GCTGGTGGCA ATAAATACCA GACACGTACA AATCCAGCT  ATGAATATAG AGGGCTTATG    2280

ATTCAGATTG TTATCTATCA ACTATAAGCC CACTGTTAAT ATTCTATTAA CTTTAATTCT    2340

CTTTCAAAGC TAAATTCCAC ACTACCACAT TAAAAAAATT AGAAAGTAGC CACGTATGGT    2400

GGCTCATGTC TATAATCCCA GCACTTTGGG AGGTTGAGGT GGGAGGATTT GCTTGAACCC    2460

AAGAGGTCCA AGGCTGCAGT GAGCCATGTT CACACCGCTG CACTCAAGCT TGGGTGACAG    2520

AGCAAGACCC CGTCCCCAAA AAATTTTTT  TTTTAATAAA CCCAAATTTG TTTGAAAACT    2580

TTTAAAAATT CAAATGATTT TTACAAGTTT TAAATAAGCT CTCCCCAAAC TTGCTTTATG    2640

CCTTCTTATT GCTTTATGA  TATATATATG CTTGGCTAAC TATATTTGCT TTTTGCTAAC    2700

AATGCTCTGG GGTCTTTTTA TGCATTTGCA TTTGCTCTTT CATCTCTGCT TGGATTATTT    2760

TAAATCATTA GGAATTAAGT TATCTTTAAA ATTTAAGTAT CTTTTTTCCA AAACATTTTT    2820

TAATAGAATA AAATATAATT TGATCTTAAA AAAAAAAAAA AAAAAAAAAA AAAAAAAAAA    2880

AAAAAAA                                                              2887

(2) INFORMATION FOR SEQ ID NO: 15:

(i) SEQUENCE CHARACTERISTICS:
         (A) LENGTH: 1323 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO: 15:

AAATGCAAAC TGGATGATGA CATGAACCTG CTGGATATTT TCATAGAGAT CGAGAAGAGG      60

GTCATCCTGG GAGAAGGAAA GTTGGACATC CTGAAAAGAG TCTGTGCCCA AATCAACAAG     120

AGCCTGCTGA AGATAATCAA CGACTATGAA GAATTCAGCA AAGGGGAGGA GTTGTGTGGG     180

GTAATGACAA TCTCGGACTC TCCAAGAGAA CAGGATAGTG AATCACAGAC TTTGGACAAA     240

GTTTACCAAA TGAAAGCAA  ACCTCGGGGA TACTGTCTGA TCATCAACAA TCACAATTTT     300

GCAAAGCAC  GGGAGAAAGT GCCCAAACTT CACAGCATTA GGGACAGGAA TGGAACACAC     360

TTGGATGCAG GGGCTTTGAC CACGACCTTT GAAGAGCTTC ATTTTGAGAT CAAGCCCCAC     420

GATGACTGCA CAGTAGAGCA AATCTATGAG ATTTTGAAAA TCTACCAACT CATGGACCAC     480

AGTAACATGG ACTGCTTCAT CTGCTGTATC CTCTCCCATG GAGACAAAGG CATCATCTAT     540

GGCACTGATG GACAGGAGGC CCCCATCTAT GAGCTGACAT CTCAGTTCAC TGGTTTGAAG     600

TGCCCTTCCC TTGCTGGAAA ACCCAAAGTG TTTTTTATTC TTATCATCAC CTCAAACGAG     660

ATATATCCCG GATGAGGCTG ACTTTCTGCT GGGGATGGCC ACTGTGAATA ACTGTGTTTC     720

CTACCGAAAC CCTGCAGAGG GAACCTGGTA CATCCAGTCA CTTTGCCAGA GCCTGAGAGA     780

GCGATGTCCT CGAGGCGATG ATATTCTCAC CATCCTGACT GAAGTGAACT ATGAAGTAAG     840

CAACAAGGAT GACAAGAAAA ACATGGGGAA ACAGATGCCT CAGCCTACTT TCACACTAAG     900

AAAAAAACTT GTCTTCCCTT CTGATTGATG GTGCTATTTT GTTTGTTTTG TTTTGTTTTG     960

TTTTTTTGAG ACAGAATCTC GCTCTGTCGC CCAGGCTGGA GTGCAGTGGC GTGATCTCGG    1020
```

-continued

```
CTCACCGCAA GCTCCGCCTC CCGGGTTCAC GCCATTCTCC TGCCTCAGCC TCCCGAGTAG    1080

CTGGGACTAC AGGGGCCCGC CACCACACCT GGCTAATTTT TTAAAAATAT TTTTAGTAGA    1140

GACAGGGTTT CACTGTGTTA GCCAGGGTGG TCTTGATCTC CTGACCTCGT GATCCACCCA    1200

CCTCGGCCTC CCAAAGTGCT GGGATTACAG GCGTGAGCCA CCGCGCCTGG CCGATGGTAC    1260

TATTTAGATA TAACACTATG TTTATTTACT AATTTTCTAG ATTTTCTACT TTATTAATTG    1320

TTT                                                                  1323
```

(2) INFORMATION FOR SEQ ID NO: 16:

(i) SEQUENCE CHARACTERISTICS:
        (A) LENGTH: 335 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 16:

```
Lys Cys Lys Leu Asp Asp Asp Met Asn Leu Leu Asp Ile Phe Ile Glu
1               5                   10                  15

Met Glu Lys Arg Val Ile Leu Gly Glu Gly Lys Leu Asp Ile Leu Lys
                20                  25                  30

Arg Val Cys Ala Gln Ile Asn Lys Ser Leu Leu Lys Ile Ile Asn Asp
            35                  40                  45

Tyr Glu Glu Phe Ser Lys Gly Glu Gly Leu Cys Gly Val Met Thr Ile
    50                  55                  60

Ser Asp Ser Pro Arg Glu Gln Asp Ser Glu Ser Gln Thr Leu Asp Lys
65                  70                  75                  80

Val Tyr Gln Met Lys Ser Lys Pro Arg Gly Tyr Cys Leu Ile Ile Asn
                85                  90                  95

Asn His Asn Phe Ala Lys Ala Arg Glu Lys Val Pro Lys Leu His Ser
            100                 105                 110

Ile Arg Asp Arg Asn Gly Thr His Leu Asp Ala Gly Ala Leu Thr Thr
        115                 120                 125

Thr Phe Glu Glu Leu His Phe Glu Ile Lys Pro His Asp Asp Cys Thr
130                 135                 140

Val Glu Gln Ile Tyr Glu Ile Trp Lys Ile Tyr Gln Leu Met Asp His
145                 150                 155                 160

Ser Asn Met Asp Cys Phe Ile Cys Cys Ile Leu Ser His Gly Asp Lys
                165                 170                 175

Gly Ile Ile Tyr Gly Thr Asp Gly Gln Glu Gly Pro Ile Tyr Glu Leu
            180                 185                 190

Thr Ser Gln Phe Thr Gly Leu Lys Cys Pro Ser Leu Ala Gly Lys Pro
        195                 200                 205

Lys Val Phe Phe Ile Gln Ala Cys Gln Gly Asp Asn Tyr Gln Lys Gly
    210                 215                 220

Ile Pro Val Glu Thr Asp Ser Glu Glu Gln Pro Tyr Leu Glu Met Asp
225                 230                 235                 240

Leu Ser Ser Pro Gln Thr Arg Tyr Ile Pro Asp Glu Ala Asp Phe Leu
                245                 250                 255

Leu Gly Met Ala Thr Val Asn Asn Cys Val Ser Tyr Arg Asn Pro Ala
            260                 265                 270

Glu Gly Thr Trp Tyr Ile Gln Ser Leu Cys Gln Ser Leu Arg Glu Arg
        275                 280                 285
```

```
Cys Pro Arg Gly Asp Asp Ile Leu Thr Ile Leu Thr Glu Val Asn Tyr
        290                 295                 300

Glu Val Ser Asn Lys Asp Asp Lys Lys Asn Met Gly Lys Gln Met Pro
305                 310                 315                 320

Gln Pro Thr Phe Thr Leu Arg Lys Lys Leu Val Phe Pro Ser Asp
                325                 330                 335
```

(2) INFORMATION FOR SEQ ID NO: 17:

(i) SEQUENCE CHARACTERISTICS:
        (A) LENGTH: 2619 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 17:

```
GTAGTGGATA GGCCTGTGAC GAAGGTGCTA CCATCGTGAG AGTAAGATTA TATTCTCCTG     60

CCTTTTAAAA AGATGGACTT CAGCAGAAAT CTTTATGATA TTGGGGAACA ACTGGACAGT    120

GAAGATCTGG CCTCCCTCAA GTTCCTGAGC CTGGACTACA TTCCGCAAAG GAAGCAAGAA    180

CCCATCAAGG ATGCCTTGAT GTTATTCCAG AGACTCCAGG AAAAGAGAAT GTTGGAGGAA    240

AGCAATCTGT CCTTCCTGAA GGAGCTGCTC TTCCGAATTA ATAGACTGGA TTTGCTGATT    300

ACCTACCTAA ACACTAGAAA GGAGGAGATG GAAAGGGAAC TTCAGACACC AGGCAGGGCT    360

CAAATTTCTG CCTACAGGGT CATGCTCTAT CAGATTTCAG AAGAAGTGAG CAGATCAGAA    420

TTGAGGTCTT TTAAGTTTCT TTTGCAAGAG GAAATCTCCA AATGCAAACT GGATGATGAC    480

ATGAACCTGC TGGATATTTT CATAGAGATG GAGAAGAGGG TCATCCTGGG AGAAGGAAAG    540

TTGGACATCC TGAAAAGAGT CTGTGCCCAA ATCAACAAGA GCCTGCTGAA GATAATCAAC    600

GACTATGAAG AATTCAGCAA AGGGGAGGAG TTGTGTGGGG TAATGACAAT CTCGGACTCT    660

CCAAGAGAAC AGGATAGTGA ATCACAGACT TTGGACAAAG TTTACCAAAT GAAAAGCAAA    720

CCTCGGGGAT ACTGTCTGAT CATCAACAAT CACAATTTTG CAAAAGCACG GGAGAAAGTG    780

CCCAAACTTC ACAGCATTAG GGACAGGAAT GGAACACACT TGGATGCAGG GGCTTTGACC    840

ACGACCTTTG AAGAGCTTCA TTTTGAGATC AAGCCCCACG ATGACTGCAC AGTAGAGCAA    900

ATCTATGAGA TTTTGAAAAT CTACCAACTC ATGGACCACA GTAACATGGA CTGCTTCATC    960

TGCTGTATCC TCTCCCATGG AGACAAAGGC ATCATCTATG GCACTGATGG ACAGGAGGCC   1020

CCCATCTATG AGCTGACATC TCAGTTCACT GGTTTGAAGT GCCCTTCCCT TGCTGGAAAA   1080

CCCAAAGTGT TTTTTATTCA GGCTTGTCAG GGGGATAACT ACCAGAAAGG TATACCTGTT   1140

GAGACTGATT CAGAGGAGCA ACCCTATTTA GAAATGGATT TATCATCACC TCAAACGAGA   1200

TATATCCCGG ATGAGGCTGA CTTTCTGCTG GGGATGGCCA CTGTGAATAA CTGTGTTTCC   1260

TACCGAAACC CTGCAGAGGG AACCTGGTAC ATCCAGTCAC TTTGCCAGAG CCTGAGAGAG   1320

CGATGTCCTC GAGGCGATGA TATTCTCACC ATCCTGACTG AAGTGAACTA TGAAGTAAGC   1380

AACAAGGATG ACAAGAAAAA CATGGGGAAA CAGATGCCTC AGCCTACTTT CACACTAAGA   1440

AAAAAACTTG TCTTCCCTTC TGATTGATGG TGCTATTTTG TTTGTTTTGT TTGTTTTGT    1500

TTTTTTGAGA CAGAATCTCG CTCTGTCGCC CAGGCTGGAG TGCAGTGGCG TGATCTCGGC   1560

TCACCGCAAG CTCCGCCTCC CGGGTTCACG CCATTCTCCT GCCTCAGCCT CCCGAGTAGC   1620

TGGGACTACA GGGCCCGCC ACCACACCTG GCTAATTTTT TAAAAATATT TTTAGTAGAG   1680

ACAGGGTTTC ACTGTGTTAG CCAGGGTGGT CTTGATCTCC TGACCTCGTG ATCCACCCAC   1740
```

```
CTCGGCCTCC CAAAGTGCTG GGATTACAGG CGTGAGCCAC CGCGCCTGGC CGATGGTACT    1800

ATTTAGATAT AACACTATGT TTATTTACTA ATTTTCTAGA TTTTCTACTT TATTAATTGT    1860

TTTGCACTTT TTTATAAGAG CTAAAGTTAA ATAGGATATT AACAACAATA ACACTGTCTC    1920

CTTTCTCTTA TGCTTAAGGC TTTGGGAATG TTTTTAGCTG GTGGCAATAA ATACCAGACA    1980

CGTACAAAAT CCAGCTATGA ATATAGAGGG CTTATGATTC AGATTGTTAT CTATCAACTA    2040

TAAGCCCACT GTTAATATTC TATTAACTTT AATTCTCTTT CAAAGCTAAA TTCCACACTA    2100

CCACATTAAA AAAATTAGAA AGTAGCCACG TATGGTGGCT CATGTCTATA ATCCCAGCAC    2160

TTTGGGAGGT TGAGGTGGGA GGATTTGCTT GAACCCAAGA GGTCCAAGGC TGCAGTGAGC    2220

CATGTTCACA CCGCTGCACT CAAGCTTGGG TGACAGAGCA AGACCCCGTC CCCAAAAAAA    2280

TTTTTTTTTT AATAAACCCA AATTTGTTTG AAAACTTTTA AAAATTCAAA TGATTTTTAC    2340

AAGTTTTAAA TAAGCTCTCC CCAAACTTGC TTTATGCCTT CTTATTGCTT TTATGATATA    2400

TATATGCTTG GCTAACTATA TTTGCTTTTT GCTAACAATG CTCTGGGGTC TTTTTATGCA    2460

TTTGCATTTG CTCTTTCATC TCTGCTTGGA TTATTTTAAA TCATTAGGAA TTAAGTTATC    2520

TTTAAAATTT AAGTATCTTT TTTCCAAAAC ATTTTTTAAT AGAATAAAAT ATAATTTGAT    2580

CTTAAAAAAA AAAAAAAAAA AAAAAAAAAA AAAAAAAA                            2619

(2) INFORMATION FOR SEQ ID NO: 18:

(i) SEQUENCE CHARACTERISTICS:
         (A) LENGTH: 464 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 18:

Met Asp Phe Ser Arg Asn Leu Tyr Asp Ile Gly Glu Gln Leu Asp Ser
1               5                   10                  15

Glu Asp Leu Ala Ser Leu Lys Phe Leu Ser Leu Asp Tyr Ile Pro Gln
            20                  25                  30

Arg Lys Gln Glu Pro Ile Lys Asp Ala Leu Met Leu Phe Gln Arg Leu
        35                  40                  45

Gln Glu Lys Arg Met Leu Glu Glu Ser Asn Leu Ser Phe Leu Lys Glu
    50                  55                  60

Leu Leu Phe Arg Ile Asn Arg Leu Asp Leu Leu Ile Thr Tyr Leu Asn
65                  70                  75                  80

Thr Arg Lys Glu Glu Met Glu Arg Glu Leu Gln Thr Pro Gly Arg Ala
                85                  90                  95

Gln Ile Ser Ala Tyr Arg Val Met Leu Tyr Gln Ile Ser Glu Glu Val
            100                 105                 110

Ser Arg Ser Glu Leu Arg Ser Phe Lys Phe Leu Leu Gln Glu Glu Ile
        115                 120                 125

Ser Lys Cys Lys Leu Asp Asp Asp Met Asn Leu Leu Asp Ile Phe Ile
    130                 135                 140

Glu Met Glu Lys Arg Val Ile Leu Gly Glu Gly Lys Leu Asp Ile Leu
145                 150                 155                 160

Lys Arg Val Cys Ala Gln Ile Asn Lys Ser Leu Leu Lys Ile Ile Asn
                165                 170                 175

Asp Tyr Glu Glu Phe Ser Lys Gly Glu Glu Leu Cys Gly Val Met Thr
            180                 185                 190
```

Ile Ser Asp Ser Pro Arg Glu Gln Asp Ser Glu Ser Gln Thr Leu Asp
    195                 200                 205

Lys Val Tyr Gln Met Lys Ser Lys Pro Arg Gly Tyr Cys Leu Ile Ile
    210                 215                 220

Asn Asn His Asn Phe Ala Lys Ala Arg Glu Lys Val Pro Lys Leu His
225                 230                 235                 240

Ser Ile Arg Asp Arg Asn Gly Thr His Leu Asp Ala Gly Ala Leu Thr
            245                 250                 255

Thr Thr Phe Glu Glu Leu His Phe Glu Ile Lys Pro His Asp Asp Cys
        260                 265                 270

Thr Val Glu Gln Ile Tyr Glu Ile Leu Lys Ile Tyr Gln Leu Met Asp
    275                 280                 285

His Ser Asn Met Asp Cys Phe Ile Cys Cys Ile Leu Ser His Gly Asp
    290                 295                 300

Lys Gly Ile Ile Tyr Gly Thr Asp Gly Gln Glu Ala Pro Ile Tyr Glu
305                 310                 315                 320

Leu Thr Ser Gln Phe Thr Gly Leu Lys Cys Pro Ser Leu Ala Gly Lys
            325                 330                 335

Pro Lys Val Phe Phe Ile Gln Ala Cys Gln Gly Asp Asn Tyr Gln Lys
        340                 345                 350

Gly Ile Pro Val Glu Thr Asp Ser Glu Glu Gln Pro Tyr Leu Glu Met
    355                 360                 365

Asp Leu Ser Ser Pro Gln Thr Arg Tyr Ile Pro Asp Glu Ala Asp Phe
    370                 375                 380

Leu Leu Gly Met Ala Thr Val Asn Asn Cys Val Ser Tyr Arg Asn Pro
385                 390                 395                 400

Ala Glu Gly Thr Trp Tyr Ile Gln Ser Leu Cys Gln Ser Leu Arg Glu
            405                 410                 415

Arg Cys Pro Arg Gly Asp Asp Ile Leu Thr Ile Leu Thr Glu Val Asn
        420                 425                 430

Tyr Glu Val Ser Asn Lys Asp Asp Lys Lys Asn Met Gly Lys Gln Met
    435                 440                 445

Pro Gln Pro Thr Phe Thr Leu Arg Lys Lys Leu Val Phe Pro Ser Asp
450                 455                 460

(2) INFORMATION FOR SEQ ID NO: 19:

(i) SEQUENCE CHARACTERISTICS:
        (A) LENGTH: 1301 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 19:

```
CCAAATGCAA ACTGGATGAT GACATGAACC TGCTGGATAT TTTCATAGAG ATGGAGAAGA      60

GGGTCATCCT GGGAGAAGGA AAGTTGGACA TCCTGAAAAG AGTCTGTGCC CAAATCAACA     120

AGAGCCTGCT GAAGATAATC AACGACTATG AAGAATTCAG CAAAGGGGCT TGACCACGA      180

CCTTTGAAGA GCTTCATTTT GAGATCAAGC CCCACGATGA CTGCACAGTA GAGCAAATCT     240

ATGAGATTTT GAAAATCTAC CAACTCATGG ACCACAGTAA CATGGACTGC TTCATCTGCT     300

GTATCCTCTC CCATGGAGAC AAAGGCATCA TCTATGGCAC TGATGGACAG GAGGCCCCCA     360

TCTATGAGCT GACATCTCAG TTCACTGGTT TGAAGTGCCC TTCCCTTGCT GGAAAACCCA     420
```

```
AAGTGTTTTT TATTCAGGCT TGTCAGGGGG ATAACTACCA GAAAGGTATA CCTGTTGAGA        480

CTGATTCAGA GGAGCAACCC TATTTAGAAA TGGATTTATC ATCACCTCAA ACGAGATATA        540

TCCCGGATGA GGCTGACTTT CTGCTGGGGA TGGCCACTGT GAATAACTGT GTTTCCTACC        600

GAAACCCTGC AGAGGGAACC TGGTACATCC AGTCACTTTG CCAGAGCCTG AGAGAGCGAT        660

GTCCTCGAGG CGATGATATT CTCACCATCC TGACTGAAGT GAACTATGAA GTAAGCAACA        720

AGGATGACAA GAAAACATG GGGAAACAGA TGCCTCAGCC TACTTTCACA CTAAGAAAAA         780

AACTTGTCTT CCCTTCTGAT TGATGGTGCT ATTTTGTTTG TTTTGTTTTG TTTTGTTTTT        840

TTGAGACAGA ATCTCGCTCT GTCGCCCAGG CTGGAGTGCA GTGGCGTGAT CTCGGCTCAC        900

CGCGAGCTCC GCCTCCCGGG TTCACGCCAT TCTCCTGCCT CAGCCTCCCG AGTAGCTGGG        960

ACTACAGGGG CCCGCCATCA CACCTGGCTA ATTTTTTAAA ATATTTTTA GTAGAGACAG        1020

GGTTTCACTG TGTTAGCCAG GGTGGTCTTG ATCTCCTGAC CTCGTGATCC ACCCACCTCG       1080

GCCTCCCAAA GTGCTGGGAT TACAGGCGTG AGCCACCGCG CCTGGCCGAT GGTACTATTT       1140

AGATATAACA CTATGTTTAT TTACTAATTT TCTAGATTTT CTACTTTATT AATTGTTTTG       1200

CACTTTTTTA TAAGAGCTAA AGTTAAATAG GATATTAACA ACAATAACAC TGTCTCCTTT       1260

CTCTTACGCT TAAGGCTTTG GGAATGTTTT TAGCTGGTGG C                          1301

(2) INFORMATION FOR SEQ ID NO: 20:

(i) SEQUENCE CHARACTERISTICS:
        (A) LENGTH: 266 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 20:

Lys Cys Lys Leu Asp Asp Asp Met Asn Leu Leu Asp Ile Phe Ile Glu
1               5                   10                  15

Met Glu Lys Arg Val Ile Leu Gly Glu Gly Lys Leu Asp Ile Leu Lys
            20                  25                  30

Arg Val Cys Ala Gln Ile Asn Lys Ser Leu Leu Lys Ile Ile Asn Asp
        35                  40                  45

Tyr Glu Glu Phe Ser Lys Gly Ala Leu Thr Thr Thr Phe Glu Glu Leu
    50                  55                  60

His Phe Glu Ile Lys Pro His Asp Asp Cys Thr Val Glu Gln Ile Tyr
65                  70                  75                  80

Glu Ile Leu Lys Ile Tyr Gln Leu Met Asp His Ser Asn Met Asp Cys
                85                  90                  95

Phe Ile Cys Cys Ile Leu Ser His Gly Asp Lys Gly Ile Ile Tyr Gly
            100                 105                 110

Thr Asp Gly Gln Glu Ala Pro Ile Tyr Glu Leu Thr Ser Gln Phe Thr
        115                 120                 125

Gly Leu Lys Cys Pro Ser Leu Ala Gly Lys Pro Lys Val Phe Phe Ile
    130                 135                 140

Gln Ala Cys Gln Gly Asp Asn Tyr Gln Lys Gly Ile Pro Val Glu Thr
145                 150                 155                 160

Asp Ser Glu Glu Gln Pro Tyr Leu Glu Met Asp Leu Ser Ser Pro Gln
                165                 170                 175

Thr Arg Tyr Ile Pro Asp Glu Ala Asp Phe Leu Leu Gly Met Ala Thr
            180                 185                 190
```

```
Val Asn Asn Cys Val Ser Tyr Arg Asn Pro Ala Glu Gly Thr Trp Tyr
        195                 200                 205

Ile Gln Ser Leu Cys Gln Ser Leu Arg Glu Arg Cys Pro Arg Gly Asp
        210                 215                 220

Asp Ile Leu Thr Ile Leu Thr Glu Val Asn Tyr Glu Val Ser Asn Lys
225                 230                 235                 240

Asp Asp Lys Lys Asn Met Gly Lys Gln Met Pro Gln Pro Thr Phe Thr
            245                 250                 255

Leu Arg Lys Lys Leu Val Phe Pro Ser Asp
        260                 265
```

(2) INFORMATION FOR SEQ ID NO: 21:

(i) SEQUENCE CHARACTERISTICS:
        (A) LENGTH: 334 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 21:

```
CCAAATGCAA ACTGGATGAT GACATGAACC TGCTGGATAT TTTCATAGAG ATGGAGAAGA     60
GGGTCATCCT GGGAGAAGGA AAGTTGGACA TCCTGAAAAG AGTCTGTGCC CAAATCAACA    120
AGAGCCTGCT GAAGATAATC AACGACTATG AAGAATTCAG CAAAGACTTT GGACAAAGTT    180
TACCAAATGA AAAGCAAACC TCGGGGATAC TGTCTGATCA TCAACAATCA CAATTTTGCA    240
AAAGCACGGG AGAAAGTGCC CAAACTTCAC AGCATTAGGG ACAGGAATGG AACACACTTG    300
GATGCAGGGT TTGAGAATGT TTTTAGCTGG TGGC                                334
```

(2) INFORMATION FOR SEQ ID NO: 22:

(i) SEQUENCE CHARACTERISTICS:
        (A) LENGTH: 91 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 22:

```
Lys Cys Lys Leu Asp Asp Asp Met Asn Leu Leu Asp Ile Phe Ile Glu
1               5                   10                  15

Met Glu Lys Arg Val Ile Leu Gly Glu Gly Lys Leu Asp Ile Leu Lys
            20                  25                  30

Arg Val Cys Ala Gln Ile Asn Lys Ser Leu Leu Lys Ile Ile Asn Asp
        35                  40                  45

Tyr Glu Glu Phe Ser Lys Asp Phe Gly Gln Ser Leu Pro Asn Glu Lys
    50                  55                  60

Gln Thr Ser Gly Ile Leu Ser Asp His Gln Gln Ser Gln Phe Cys Lys
65                  70                  75                  80

Ser Thr Gly Glu Ser Ala Gln Thr Ser Gln His
            85                  90
```

(2) INFORMATION FOR SEQ ID NO: 23:

(i) SEQUENCE CHARACTERISTICS:
        (A) LENGTH: 829 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 23:

| | |
|---|---|
| ATGGACTTCA GCAGAAATCT TTATGATATT GGGGAACAAC TGGACAGTGA AGATCTGGCC | 60 |
| TCCCTCAAGT TCCTGAGCCT GGACTACATT CCGCAAAGGA AGCAAGAACC CATCAAGGAT | 120 |
| GCCTTGATGT TATTCCAGAG ACTCCAGGAA AAGAGAATGT TGGAGGAAAG CAATCTGTCC | 180 |
| TTCCTGAAGG AGCTGCTCTT CCGAATTAAT AGACTGGATT TGCTGATTAC CTACCTAAAC | 240 |
| ACTAGAAAGG AGGAGATGGA AAGGGAACTT CAGACACCAG GCAGGGCTCA AATTTCTGCC | 300 |
| TACAGGGTCA TGCTCTATCA GATTTCAGAA GAAGTGAGCA GATCAGAATT GAGGTCTTTT | 360 |
| AAGTTTCTTT TGCAAGAGGA AATCTCCAAA TGCAAACTGG ATGATGACAT GAACCTGCTG | 420 |
| GATATTTTCA TAGAGATGGA AAGAGGGTC ATCCTGGGAG AAGGAAAGTT GGACATCCTG | 480 |
| AAAAGAGTCT GTGCCCAAAT CAACAAGAGC CTGCTGAAGA TAATCAACGA CTATGAAGAA | 540 |
| TTCAGCAAAG AGAGAAGCAG CAGCCTTGAA GGAAGTCCTG ATGAATTTTC AAATGGGGAG | 600 |
| GAGTTGTGTG GGGTAATGAC AATCTCGGAC TCTCCAAGAG AACAGGATAG TGAATCACAG | 660 |
| ACTTTGGACA AAGTTTACCA AATGAAAAGC AAACCTCGGG GATACTGTCT GATCATCAAC | 720 |
| AATCACAATT TGCAAAAGC ACGGGAGAAA GTGCCCAAAC TTCACAGCAT TAGGGACAGG | 780 |
| AATGGAACAC ACTTGGATGC AGGGTTTGGG AATGTTTTTA GCTGGTGGC | 829 |

(2) INFORMATION FOR SEQ ID NO: 24:

(i) SEQUENCE CHARACTERISTICS:
        (A) LENGTH: 784 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 24:

| | |
|---|---|
| ATGGACTTCA GCAGAAATCT TTATGATATT GGGGAACAAC TGGACAGTGA AGATCTGGCC | 60 |
| TCCCTCAAGT TCCTGAGCCT GGACTACATT CCGCAAAGGA AGCAAGAACC CATCAAGGAT | 120 |
| GCCTTGATGT TATTCCAGAG ACTCCAGGAA AAGAGAATGT TGGAGGAAAG CAATCTGTCC | 180 |
| TTCCTGAAGG AGCTGCTCTT CCGAATTAAT AGACTGGATT TGCTGATTAC CTACCTAAAC | 240 |
| ACTAGAAAGG AGGAGATGGA AAGGGAACTT CAGACACCAG GCAGGGCTCA AATTTCTGCC | 300 |
| TACAGGGTCA TGCTCTATCA GATTTCAGAA GAAGTGAGCA GATCAGAATT GAGGTCTTTT | 360 |
| AAGTTTCTTT TGCAAGAGGA AATCTCCAAA TGCAAACTGG ATGATGACAT GAACCTGCTG | 420 |
| GATATTTTCA TAGAGATGGA AAGAGGGTC ATCCTGGGAG AAGGAAAGTT GGACATCCTG | 480 |
| AAAAGAGTCT GTGCCCAAAT CAACAAGAGC CTGCTGAAGA TAATCAACGA CTATGAAGAA | 540 |
| TTCAGCAAAG GGAGGAGTT GTGTGGGGTA ATGCAATCT CGGACTCTCC AAGAGAACAG | 600 |
| GATAGTGAAT CACAGACTTT GGACAAAGTT TACCAAATGA AAGCAAACC TCGGGGATAC | 660 |
| TGTCTGATCA TCAACAATCA CAATTTTGCA AAAGCACGGG AGAAAGTGCC CAAACTTCAC | 720 |
| AGCATTAGGG ACAGGAATGG AACACACTTG GATGCAGGGT TTGGGAATGT TTTTAGCTGG | 780 |
| TGGC | 784 |

(2) INFORMATION FOR SEQ ID NO: 25:

(i) SEQUENCE CHARACTERISTICS:
        (A) LENGTH: 261 amino acids

```
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 25:

Met Asp Phe Ser Arg Asn Leu Tyr Asp Ile Gly Glu Gln Leu Asp Ser
1               5                   10                  15

Glu Asp Leu Ala Ser Leu Lys Phe Leu Ser Leu Asp Tyr Ile Pro Gln
                20                  25                  30

Arg Lys Gln Glu Pro Ile Lys Asp Ala Leu Met Leu Phe Gln Arg Leu
            35                  40                  45

Gln Glu Lys Arg Met Leu Glu Glu Ser Asn Leu Ser Phe Leu Lys Glu
50                  55                  60

Leu Leu Phe Arg Ile Asn Arg Leu Asp Leu Leu Ile Thr Tyr Leu Asn
65                  70                  75                  80

Thr Arg Lys Glu Glu Met Glu Arg Glu Leu Gln Thr Pro Gly Arg Ala
                85                  90                  95

Gln Ile Ser Ala Tyr Arg Val Met Leu Tyr Gln Ile Ser Glu Glu Val
            100                 105                 110

Ser Arg Ser Glu Leu Arg Ser Phe Lys Phe Leu Leu Gln Glu Glu Ile
        115                 120                 125

Ser Lys Cys Lys Leu Asp Asp Asp Met Asn Leu Leu Asp Ile Phe Ile
130                 135                 140

Glu Met Glu Lys Arg Val Ile Leu Gly Glu Gly Lys Leu Asp Ile Leu
145                 150                 155                 160

Lys Arg Val Cys Ala Gln Ile Asn Lys Ser Leu Leu Lys Ile Ile Asn
                165                 170                 175

Asp Tyr Glu Glu Phe Ser Lys Gly Glu Glu Leu Cys Gly Val Met Thr
            180                 185                 190

Ile Ser Asp Ser Pro Arg Glu Gln Asp Ser Glu Ser Gln Thr Leu Asp
        195                 200                 205

Lys Val Tyr Gln Met Lys Ser Lys Pro Arg Gly Tyr Cys Leu Ile Ile
210                 215                 220

Asn Asn His Asn Phe Ala Lys Ala Arg Glu Lys Val Pro Lys Leu His
225                 230                 235                 240

Ser Ile Arg Asp Arg Asn Gly Thr His Leu Asp Ala Gly Phe Gly Asn
                245                 250                 255

Val Phe Ser Trp Trp
            260

(2) INFORMATION FOR SEQ ID NO: 26:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 26:

GACTCGAGTC TAGAGTCGAC TTTTTTTTTT TTTTTTT                              37

(2) INFORMATION FOR SEQ ID NO: 27:

(i) SEQUENCE CHARACTERISTICS:
        (A) LENGTH: 20 base pairs
```

```
      (B) TYPE: nucleic acid
      (C) STRANDEDNESS: single
      (D) TOPOLOGY: linear (ii) MOLECULE TYPE: oligonucleotide (xi) SEQUENCE DESCRIPTION: SEQ ID NO: 27:

GACTCGAGTC TAGAGTCGAC                                                      20

(2) INFORMATION FOR SEQ ID NO: 28:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 28:

GAGGATCCCC AAATGCAAAC TGGATGATGA C                                         31

(2) INFORMATION FOR SEQ ID NO: 29:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 29:

TTGGATCCAG ATGGACTTCA GCAGAAATCT T                                         31

(2) INFORMATION FOR SEQ ID NO: 30:

(i) SEQUENCE CHARACTERISTICS:
        (A) LENGTH: 277 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 30:
```

Met Glu Asn Thr Glu Asn Ser Val Asp Ser Lys Ser Ile Lys Asn Leu
1               5                  10                  15

Glu Pro Lys Ile Ile His Gly Ser Glu Ser Met Asp Ser Gly Ile Ser
            20                  25                  30

Leu Asp Asn Ser Tyr Lys Met Asp Tyr Pro Glu Met Gly Leu Cys Ile
        35                  40                  45

Ile Ile Asn Asn Lys Asn Phe His Lys Ser Thr Gly Met Thr Ser Arg
    50                  55                  60

Ser Gly Thr Asp Val Asp Ala Ala Asn Leu Arg Glu Thr Phe Arg Asn
65                  70                  75                  80

Leu Lys Tyr Glu Val Arg Asn Lys Asn Asp Leu Thr Arg Glu Glu Ile
                85                  90                  95

Val Glu Leu Met Arg Asp Val Ser Lys Glu Asp His Ser Lys Arg Ser
            100                 105                 110

Ser Phe Val Cys Val Leu Leu Ser His Gly Glu Glu Gly Ile Ile Phe
        115                 120                 125

Gly Thr Asn Gly Pro Val Asp Leu Lys Lys Ile Thr Asn Phe Phe Arg
    130                 135                 140

```
Gly Asp Arg Cys Arg Ser Leu Thr Gly Lys Pro Lys Leu Phe Ile Ile
145                 150                 155                 160

Gln Ala Cys Arg Gly Thr Glu Leu Asp Cys Gly Ile Glu Thr Asp Ser
                165                 170                 175

Gly Val Asp Asp Asp Met Ala Cys His Lys Ile Pro Val Asp Ala Asp
            180                 185                 190

Phe Leu Tyr Ala Tyr Ser Thr Ala Pro Gly Tyr Tyr Ser Trp Arg Asn
        195                 200                 205

Ser Lys Asp Gly Ser Trp Phe Ile Gln Ser Leu Cys Ala Met Leu Lys
    210                 215                 220

Gln Tyr Ala Asp Lys Leu Glu Phe Met His Ile Leu Thr Arg Val Asn
225                 230                 235                 240

Arg Lys Val Ala Thr Glu Phe Glu Ser Phe Ser Phe Asp Ala Thr Phe
                245                 250                 255

His Ala Lys Lys Gln Ile Pro Cys Ile Val Ser Met Leu Thr Lys Glu
            260                 265                 270

Leu Tyr Phe Tyr His
        275

(2) INFORMATION FOR SEQ ID NO: 31:

(i) SEQUENCE CHARACTERISTICS:
        (A) LENGTH: 293 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 31:

Met Ser Ser Ala Ser Gly Leu Arg Arg Gly His Pro Ala Gly Gly Glu
1               5                   10                  15

Glu Asn Met Thr Glu Thr Asp Ala Phe Tyr Lys Arg Glu Met Phe Asp
                20                  25                  30

Pro Ala Glu Lys Tyr Lys Met Asp His Arg Arg Gly Ile Ala Leu
            35                  40                  45

Ile Phe Asn His Glu Arg Phe Phe Trp His Leu Thr Leu Pro Glu Arg
50                  55                  60

Arg Arg Thr Cys Ala Asp Arg Asp Asn Leu Thr Arg Arg Phe Ser Asp
65                  70                  75                  80

Leu Gly Phe Glu Val Lys Cys Phe Asn Asp Leu Lys Ala Glu Glu Leu
                85                  90                  95

Leu Leu Lys Ile His Glu Val Ser Thr Val Ser His Ala Asp Ala Asp
                100                 105                 110

Cys Phe Val Cys Val Phe Leu Ser His Gly Glu Gly Asn His Ile Tyr
                115                 120                 125

Ala Tyr Asp Ala Lys Ile Glu Ile Gln Thr Leu Thr Gly Leu Phe Lys
        130                 135                 140

Gly Asp Lys Cys His Ser Leu Val Gly Lys Pro Lys Ile Phe Ile Ile
145                 150                 155                 160

Gln Ala Cys Arg Gly Asn Gln His Asp Val Pro Val Ile Pro Leu Asp
                165                 170                 175

Val Val Asp Asn Gln Thr Glu Lys Leu Asp Thr Asn Ile Thr Glu Val
            180                 185                 190

Asp Ala Ala Ser Val Tyr Thr Leu Pro Ala Gly Ala Asp Phe Leu Met
        195                 200                 205
```

```
Cys Tyr Ser Val Ala Glu Gly Tyr Tyr Ser His Arg Glu Thr Val Asn
    210                 215                 220

Gly Ser Trp Tyr Ile Gln Asp Leu Cys Glu Met Leu Gly Lys Tyr Gly
225                 230                 235                 240

Ser Ser Leu Glu Phe Thr Glu Leu Leu Thr Leu Val Asn Arg Lys Val
                245                 250                 255

Ser Gln Arg Arg Val Asp Phe Cys Lys Asp Pro Ser Ala Ile Gly Lys
            260                 265                 270

Lys Gln Val Pro Cys Phe Ala Ser Met Leu Thr Lys Lys Leu His Phe
        275                 280                 285

Phe Pro Lys Ser Asn
    290

(2) INFORMATION FOR SEQ ID NO: 32:

(i) SEQUENCE CHARACTERISTICS:
        (A) LENGTH: 398 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 32:

AAATGCAAAC TGGATGATGA CATGAACCTG CTGGATATTT TCATAGAGAT GGAGAAGAGG      60

GTCATCCTGG GAGAAGGAAA GTTGGACATC CTGAAAAGAG TCTGTGCCCA ATCAACAAG     120

AGCCTGCTGA AGATAATCAA CGACTATGAA GAATTCAGCA AGGGGAGGA GTTGTGTGGG     180

GTAATGACAA TCTCGGACTC TCCAAGAGAA CAGGATAGTG AATCACAGAC TTTTGGACAAA    240

GTTTACCAAA TGAAAAGCAA ACCTCGGGGA TACTGTCTGA TCATCAACAA TCACAATTTT    300

GCAAAAGCAC GGGAGAAAGT GCCCAAACTT CACAGCATTA GGGACAGGAA TGGAACACAC    360

TTGGATGCAG GGTTTGAGAA TGTTTTTAGC TGGTGGCA                            398

(2) INFORMATION FOR SEQ ID NO: 33:

(i) SEQUENCE CHARACTERISTICS:
        (A) LENGTH: 1443 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 33:

CCAAATGCAA ACTGGATGAT GACATGAACC TGCTGGATAT TTTCATAGAG ATGGAGAAGA      60

GGGTCATCCT GGGAGAAGGA AAGTTGGACA TCCTGAAAAG AGTCTGTGCC CAAATCAACA    120

AGAGCCTGCT GAAGATAATC AACGACTATG AAGAATTCAG CAAAGACTTT GGACAAAGTT    180

TACCAAATGA AAAGCAAACC TCGGGGATAC TGTCTGATCA TCAACAATCA CAATTTTGCA    240

AAAGCACGGG AGAAAGTGCC CAAACTTCAC AGCATTAGGG ACAGGAATGG AACACACTTG    300

GATGCAGGGG CTTTGACCAC GACCTTTGAA GAGCTTCATT TGAGATCAA GCCCCACGAT    360

GACTGCACAG TAGAGCAAAT CTATGAGATT TGGAAAATCT ACCAACTCAT GGACCACAGT    420

AACATGGACT GCTTCATCTG CTGTATCCTC TCCCATGGAG ACAAAGGCAT CATCTATGGC    480

ACTGATGGAC AGGAGGGCCC CATCTATGAG CTGACATCTC AGTTCACTGG TTTGAAGTGC    540

CCTTCCCTTG CTGGAAAACC CAAAGTGTTT TTTATTCAGG CTTGTCAGGG GGATAACTAC    600
```

```
                                                    -continued
CAGAAAGGTA TACCTGTTGA GACTGATTCA GAGGAGCAAC CCTATTTAGA AATGGATTTA    660

TCATCACCTC AAACGAGATA TATCCCGGAT GAGGCTGACT TTCTGCTGGG GATGGCCACT    720

GTGAATAACT GTGTTTCCTA CCGAAACCCT GCAGAGGGAA CCTGGTACAT CCAGTCACTT    780

TGCCAGAGCC TGAGAGAGCG ATGTCCTCGA GGCGATGATA TTCTCACCAT CCTGACTGAA    840

GTGAACTATG AAGTAAGCAA CAAGGATGAC AAGAAAAACA TGGGGAAACA GATGCCTCAG    900

CCTACTTTCA CACTAAGAAA AAAACTTGTC TTCCCTTCTG ATTGATGGTG CTATTTTGTT    960

TGTTTTGTTT TGTTTTGTTT TTTTGAGACA GAATCTCGCT CTGTCGCCCA GGCTGGAGTG   1020

CAGTGGCGTG ATCTCGGCTC ACCGCGAGCT CCGCCTCCCG GGTTCACGCC ATTCTCCTGC   1080

CTCAGCCTCC CGAGTAGCTG GGACTACAGG GGCCCGCCAT CACACCTGGC TAATTTTTTA   1140

AAAATATTTT TAGTAGAGAC AGGGTTTCAC TGTGTTAGCC AGGGTGGTCT TGATCTCCTG   1200

ACCTCGTGAT CCACCCACCT CGGCCTCCCA AAGTGCTGGG ATTACAGGCG TGAGCCACCG   1260

CGCCTGGCCG ATGGTACTAT TTAGATATAA CACTATGTTT ATTTACTAAT TTTCTAGATT   1320

TTCTACTTTA TTAATTGTTT TGCACTTTTT TATAAGAGCT AAAGTTAAAT AGGATATTAA   1380

CAACAATAAC ACTGTCTCCT TTCTCTTACG CTTAAGGCTT TGGGAATGTT TTTAGCTGGT   1440

GGC                                                                1443

(2) INFORMATION FOR SEQ ID NO: 34:

(i) SEQUENCE CHARACTERISTICS:
        (A) LENGTH: 91 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 34:

Lys Cys Lys Leu Asp Asp Asp Met Asn Leu Leu Asp Ile Phe Ile Glu
 1               5                  10                  15

Met Glu Lys Arg Val Ile Leu Gly Glu Gly Lys Leu Asp Ile Leu Lys
                20                  25                  30

Arg Val Cys Ala Gln Ile Asn Lys Ser Leu Leu Lys Ile Ile Asn Asp
            35                  40                  45

Tyr Glu Glu Phe Ser Lys Asp Phe Gly Gln Ser Leu Pro Asn Glu Lys
        50                  55                  60

Gln Thr Ser Gly Ile Leu Ser Asp His Gln Gln Ser Gln Phe Cys Lys
65                  70                  75                  80

Ser Thr Gly Glu Ser Ala Gln Thr Ser Gln His
                85                  90
```

MODULATORS OF THE FUNCTION OF FAS RECEPTORS AND OTHER PROTEINS

FIELD OF THE INVENTION

The present invention is generally in the field of receptors belonging to the TNF/NGF superfamily of receptors and the control of their biological functions. The TNF/NGF superfamily of receptors includes receptors such as the p55 and p75 tumor necrosis factor receptors (TNF-Rs, hereinafter called p55-R and p75-R) and the FAS ligand receptor (also called FAS/APO1 or FAS-R and hereinafter will be called FAS-R) and others. More specifically, the present invention concerns novel proteins which bind to the protein MORT-1 (or FADD), and more specifically, it relates to one such MORT-1 binding protein, herein designated MACH.

Accordingly, the present invention concerns, in general, new proteins which are capable of modulating or mediating the function of MORT-1 or of other proteins which bind to MORT-1 directly or indirectly. In particular, the present invention concerns MACH, its preparation and uses thereof, as well as the various novel isoforms of MACH, their preparation and uses.

BACKGROUND OF THE RELATED ART

Tumor Necrosis Factor (TNF-α) and Lymphotoxin (TNF-β) (hereinafter, TNF, refers to both TNF-α and TNF-β) are multifunctional pro-inflammatory cytokines formed mainly by mononuclear phagocytes, which have many effects on cells (Wallach, 1986; and Beutler and Cerami, (1987). Both TNF-α and TNF-β initiate their effects by binding to specific cell surface receptors. Some of the effects are likely to be beneficial to the organism: they may destroy, for example, tumor cells or virus infected cells and augment antibacterial activities of granulocytes. In this way, TNF contributes to the defense of the organism against tumors and infectious agents and contributes to the recovery from injury. Thus, TNF can be used as an anti-tumor agent in which application it binds to its receptors on the surface of tumor cells and thereby initiates the events leading to the death of the tumor cells. TNF can also be used as an anti-infectious agent.

However, both TNF-α and TNF-β also have deleterious effects. There is evidence that overproduction TNF-α can play a major pathogenic role in several diseases. For example, effects of TNF-α, primarily on the vasculature, are known to be a major cause for symptoms of septic shock (Tracey et al, 1986). In some diseases, TNF may cause excessive loss of weight (cachexia) by suppressing activities of adipocytes and by causing anorexia, and TNF-α was thus called cachetin. It was also described as a mediator of the damage to tissues in rheumatic diseases (Beutler and Cerami, 1987) and as a major mediator of the damage observed in graft-versus-host reactions (Piquet et al, 1987). In addition, TNF is known to be involved in the process of inflammation and in many other diseases.

Two distinct, independently expressed, receptors, the p55 and p75 TNF-Rs, which bind both TNF-α and TNF-β specifically, initiate and/or mediate the above noted biological effects of TNF. These two receptors have structurally dissimilar intracellular domains suggesting that they signal differently (See Hohmann et al, 1989; Engelmann et al, 1990; Brockhaus et al, 1990; Leotscher et al, 1990; Schall et al, 1990; Nophar et al, 1990; Smith et al, 1990; and Heller et al, 1990). However, the cellular mechanisms, for example, the various proteins and possibly other factors, which are involved in the intracellular signaling of the p55 an p75 TNF-Rs have yet to be elucidated. It is this intracellular signaling, which occurs usually after the binding of the ligand, i.e., TNF (α or β), to the receptor, that is responsible for the commencement of the cascade of reactions that ultimately result in the observed response of the cell to TNF.

As regards the above-mentioned cytocidal effect of TNF, in most cells studied so far, this effect is triggered mainly by the p55 TNF-R. Antibodies against the extracellular domain (ligand binding domain) of the p55 TNF-R can themselves trigger the cytocidal effect (see EP 412486) which correlates with the effectivity of receptor cross-linking by the antibodies, believed to be the first step in the generation of the intracellular signaling process. Further, mutational studies (Brakebusch et al, 1992; Tartaglia et al, 1993) have shown that the biological function of the p55 TNF-R depends on the integrity of its intracellular domain, and accordingly it has been suggested that the initiation of intracellular signaling leading to the cytocidal effect of TNF occurs as a consequence of the association of two or more intracellular domains of the p55 TNF-R. Moreover, TNF (α and β) occurs as a homotrimer, and as such, has been suggested to induce intracellular signaling via the p55 TNF-R by way of its ability to bind to and to cross-link the receptor molecules, i.e., cause receptor aggregation.

Another member of the TNF/NGF superfamily of receptors is the FAS receptor (FAS-R) which has also been called the FAS antigen, a cell-surface protein expressed in various tissues and sharing homology with a number of cell-surface receptors including TNF-R and NGF-R. The FAS-R mediates cell death in the form of apoptosis (Itoh et al, 1991), and appears to serve as a negative selector of autoreactive T cells, i.e., during maturation of T cells, FAS-R mediates the apoptopic death of T cells recognizing self-antigens. It has also been found that mutations in the FAS-R gene (lpr) cause a lymphoproliferation disorder in mice that resembles the human autoimmune disease systemic lupus erythematosus (SLE) (Watanabe-Fukunaga et al, 1992). The ligand for the FAS-R appears to be a cell-surface associated molecule carried by, amongst others, killer T cells (or cytotoxic T lymphocytes—CTLs), and hence when such CTLs contact cells carrying FAS-R, they are capable of inducing apoptopic cell death of the FAS-R-carrying cells. Further, a monoclonal antibody has been prepared that is specific for FAS-R, this monoclonal antibody being capable of inducing apoptopic cell death in cells carrying FAS-R, including mouse cells transformed by cDNA encoding human FAS-R (Itoh et al, 1991).

While some of the cytotoxic effects of lymphocytes are mediated by interaction of a lymphocyte-produced ligand with the widely occurring cell surface receptor FAS-R (CD95), which has the ability to trigger cell death, it has also been found that various other normal cells, besides T lymphocytes, express the FAS-R on their surface and can be killed by the triggering of this receptor. Uncontrolled induction of such a killing process is suspected to contribute to tissue damage in certain diseases, for example, the destruction of liver cells in acute hepatitis. Accordingly, finding ways to restrain the cytotoxic activity of FAS-R may have therapeutic potential.

Conversely, since it has also been found that certain malignant cells and HIV-infected cells carry the FAS-R on their surface, antibodies against FAS-R, or the FAS-R ligand, may be used to trigger the FAS-R mediated cytotoxic effects in these cells and thereby provide a means for combating such malignant cells or HIV-infected cells (see Itoh et al, 1991). Finding yet other ways for enhancing the cytotoxic activity of FAS-R may therefore also have therapeutic potential.

It has been a long felt need to provide a way for modulating the cellular response to TNF (α or β) and FAS-R ligand. For example, in the pathological situations mentioned above, where TNF or FAS-R ligand is overexpressed, it is desirable to inhibit the TNF- or FAS-R ligand-induced cytocidal effects, while in other situations, e.g., wound healing applications, it is desirable to enhance the TNF effect, or in the case of FAS-R, in tumor cells or HIV-infected cells, it is desirable to enhance the FAS-R mediated effect.

A number of approaches have been made by the laboratory of the applicants (see for example, European Application Nos. EP 186833, EP 308378, EP 398327 and EP 412486) to regulate the deleterious effects of TNF by inhibiting the binding of TNF to its receptors using anti-TNF antibodies or by using soluble TNF receptors (being essentially the soluble extracellular domains of the receptors) to compete with the binding of TNF to the cell surface-bound TNF-Rs. Further, on the basis that TNF-binding to its receptors is required for the TNF-induced cellular effects, approaches by the laboratory of the applicants (see for example EPO 568925) have been made to modulate the TNF effect by modulating the activity of the TNF-Rs.

Briefly, EPO 568925 relates to a method of modulating signal transduction and/or cleavage in TNF-Rs whereby peptides or other molecules may interact either with the receptor itself or with effector proteins interacting with the receptor, thus modulating the normal function of the TNF-Rs. In EPO 568925, there is described the construction and characterization of various mutant p55 TNF-Rs, having mutations in the extracellular, transmembrane, and intracellular domains of the p55 TNF-R. In this way, regions within the above domains of the p55 TNF-R were identified as being essential to the functioning of the receptor, i.e., the binding of the ligand (TNF) and the subsequent signal transduction and intracellular signaling which ultimately results in the observed TNF-effect on the cells. Further, there is also described a number of approaches to isolate and identify proteins, peptides or other factors which are capable of binding to the various regions in the above domains of the TNF-R, which proteins, peptides and other factors may be involved in regulating or modulating the activity of the TNF-R. A number of approaches for isolating and cloning the DNA sequences encoding such proteins and peptides; for constructing expression vectors for the production of these proteins and peptides; and for the preparation of antibodies or fragments thereof which interact with the TNF-R or with the above proteins and peptides that bind various regions of the TNF-R, are also set forth in EPO 568925. However, EPO 568925 does not specify the actual proteins and peptides which bind to the intracellular domains of the TNF-Rs (e.g., p55 TNF-R), nor does it describe the yeast two-hybrid approach to isolate and identify such proteins or peptides which bind to the intracellular domains of TNF-Rs. Similarly, heretofore there has been no disclosure of proteins or peptides capable of binding the intracellular domain of FAS-R.

Thus, when it is desired to inhibit the effect of TNF, or the FAS-R ligand, it would be desirable to decrease the amount or the activity of TNF-Rs or FAS-R at the cell surface, while an increase in the amount or the activity of TNF-RS or FAS-R would be desired when an enhanced TNF or FAS-R ligand effect is sought. To this end the promoters of both the p55 TNF-R and the p75 TNF-R have been sequenced, analyzed and a number of key sequence motifs have been found that are specific to various transcription regulating factors, and as such the expression of these TNF-Rs can be controlled at their promoter level, i.e., inhibition of transcription from the promoters for a decrease in the number of receptors, and an enhancement of transcription from the promoters for an increase in the number of receptors (EP 606869 and WO 95/31206). Corresponding studies concerning the control of FAS-R at the level of the promoter of the FAS-R gene have yet to be reported.

While it is known that the tumor necrosis factor (TNF) receptors, and the structurally-related receptor FAS-R, trigger in cells, upon stimulation by leukocyte-produced ligands, destructive activities that lead to their own demise, the mechanisms of this triggering are still little understood. Mutational studies indicate that in FAS-R and the p55 TNF receptor (p55-R) signaling for cytotoxicity involve distinct regions within their intracellular domains (Brakebusch et al, 1992; Tartaglia et al, 1993; Itoh and Nagata, 1993). These regions (the 'death domains') have sequence similarity. The 'death domains' of both FAS-R and p55-R tend to self-associate. Their self-association apparently promotes that receptor aggregation which is necessary for initiation of signaling (see Song et al, 1994; Wallach et al, 1994; Boldin et al, 1995), and at high levels of receptor expression can result in triggering of ligand-independent signaling (Bolding et al, 1995).

Thus, prior to WO 95/31544 and the present invention, there have not been provided proteins which may regulate the effect of ligands belonging to the TNF/NGF superfamily, such as the TNF or FAS-R ligand effect on cells, by mediation of the intracellular signaling process, which signaling is believed to be governed to a large extent by the intracellular domains (ICs) of the receptors belonging to the TNF/NGF superfamily of receptors, such as those of the TNF-Rs, i.e., the p55 and p75 TNF-R intracellular domains (p55IC and p75IC, respectively), as well as the FAS-IC.

Some of the cytotoxic effects of lymphocytes are mediated by interaction of a lymphocyte-produced ligand with FAS-R (CD-95), a widely occurring cell surface receptor which has the ability to trigger cell death (see Nagata and Golstein, 1995). Cell killing by mononuclear phagocytes involves a ligand-receptor couple, TNF and its receptor p55-R (CD120), that is structurally related to FAS-R and its ligand (see also Vandenabeele et al, 1995). Like other receptor-induced effects, cell death induction by the TNF receptors and FAS-R occurs via a series of protein-protein interactions, leading from ligand-receptor binding to the eventual activation of enzymatic effector functions, which in the case of these particular receptors results in cell death. Previous studies have elucidated non-enzymatic protein-protein interactions that initiate signaling for cell death: binding of trimeric TNF or the FAS-R ligand molecules to the receptors, the resulting interactions of their intracellular domains (Brakebusch et al, 1992; Tartaglia et al, 1993; Itoh and Nagata, 1993) augmented by a propensity of the death-domain motifs to self-associate, (Boldin et al, 1995a), and induced binding of two cytoplasmic proteins (which can also bind to each other) to the receptors' intracellular domains—MORT-1 (or FADD) to FAS-R (Boldin et al, 1995b; Chinnaiyan et al, 1995; Kischkel et al, 1995) and TRADD to p55-R (Hsu et al, 1995; Hsu et al, 1996).

Three proteins that bind to the intracellular domain of FAS-R and p55-R at the "death domain" region involved in cell-death induction by the receptors through hetero-association of homologous regions and that independently are also capable of triggering cell death were identified by the yeast two-hybrid screening procedure. One of these is the protein, MORT-1 (Boldin et al 1995b) also known as FADD (Chinnaiyan et al, 1995), that binds specifically to FAS-R. A second one, TRADD (see also Hsu et al, 1995, 1996), binds to p55-R, and the third, RIP (see also Stanger et al, 1995), binds to both FAS-R and p55-R. Besides their binding to FAS-R and p55-R, these proteins are also capable of binding to each other, which provides for a functional "cross-talk" between FAS-R and p55-R. These bindings occur through a conserved sequence motif, the "death domain module" common to the receptors and their associated proteins. Furthermore, although in the yeast two-hybrid test MORT-1 was shown to bind spontaneously to FAS-R, in mammalian cells this binding takes place only after stimulation of the receptor, suggesting that MORT-1 participates in the initiating events of FAS-R signaling. MORT-1 does not contain any sequence motif characteristic of enzymatic activity, and therefore, its ability to trigger cell death seems not to involve an intrinsic activity of MORT-1 itself, but rather, activation of some other protein(s) that bind MORT-1 and act further downstream in the signaling cascade. Cellular expression of MORT-1 mutants lacking the N-terminal part of the molecule has been shown to block cytotoxicity induction by FAS/APO1 (FAS-R) or p55-R (Hsu et al, 1996; Chinnaiyan et al, 1996), indicating that this N-terminal region transmits the signaling for the cytocidal effect of both receptors through protein-protein interactions.

Recent studies have implicated a group of cytoplasmic thiol proteases which are structurally related to the *Caenorhabditis elegans* protease CED3 and to the mammalian interleukin-1β converting enzyme (ICE) in the onset of various physiological cell death processes (reviewed in Kumar, 1995 and Henkart, 1996). There have also been some indications that protease(s) of this family may take part in the cell-cytotoxicity induced by FAS-R and TNF-Rs. Specific peptide inhibitors of the proteases and two virus-encoded proteins that block their function, the cowpox protein crmA and the Baculovirus p35 protein, were found to provide protection to cells against this cell-cytotoxicity (Enari et al, 1995; Los et al, 1995; Tewari et al, 1995; Xue et al, 1995; Beidler et al, 1995). Rapid cleavage of certain specific cellular proteins, apparently mediated by protease(s) of the CED3/ICE family, was observed in cells shortly after stimulation of FAS-R or TNF-Rs. Heretofore, no information has been presented as to the identity of the specific CED3/ICE-related protease(s) involved, nor of the mechanisms of activation of these protease(s) by the receptors.

SUMMARY OF THE INVENTION

It is an object of the invention to provide novel proteins, including all isoforms, analogs, fragments or derivatives thereof, which are capable of binding to MORT-1, which itself binds to the intracellular domain of the FAS-R, which novel proteins affect the intracellular signaling process initiated by the binding of FAS ligand to its receptor.

Another object of the invention is to provide antagonists (e.g., antibodies, peptides, organic compounds, or even some isoforms) to the above novel proteins, analogs, fragments and derivatives thereof, which may be used to inhibit the signaling process, or, more specifically, the cell-cytotoxicity, when desired.

A further object of the invention is to use the above novel proteins, analogs, fragments and derivatives thereof, to isolate and characterize additional proteins or factors, which may be involved in regulation of receptor activity, e.g., other proteases which cleave the novel proteins to render them biologically active, and/or to isolate and identify other receptors further upstream in the signaling process to which these novel proteins, analogs, fragments and derivatives thereof bind (e.g., other FAS-Rs or related receptors), and hence, in whose function they are also involved.

A still further object of the invention is to provide inhibitors which can be introduced into cells to bind or interact with the MACH proteases and inhibit their proteolytic activity.

Moreover, it is an object of the present invention to use the above-mentioned novel proteins, and analogs, fragments and derivatives thereof as antigens for the preparation of polyclonal and/or monoclonal antibodies thereto. The antibodies, in turn, may be used, for example, for the purification of the new proteins from different sources, such as cell extracts or transformed cell lines.

Furthermore, these antibodies may be used for diagnostic purposes, e.g., for identifying disorders related to abnormal functioning of cellular effects mediated by the FAS-R or other related receptors.

A further object of the invention is to provide pharmaceutical compositions comprising the above novel proteins, or analogs, fragments or derivatives thereof, as well as pharmaceutical compositions comprising the above noted antibodies or other antagonists.

In accordance with the present invention, a novel protein, MACH, which is capable of binding to, or interacting with, MORT-1, which itself binds to the intracellular domain of the FAS-R was discovered. MACH probably functions as an effector component of the cell-death pathway initiated by the binding of FAS ligand to FAS-R at the cell surface, and this by virtue of the fact that at least some of the isoforms of MACH appear to be active intracellular proteases. Proteases of the CED3/ICE family have been implicated in the apoptopic process triggered by FAS-R. MORT-1 (or FADD) binds to the intracellular domain of FAS-R upon activation of this receptor and the novel MACH proteins of the present invention bind to MORT-1. The MACH protein, cloned and characterized in accordance with the present invention, actually exists in multiple isoforms, some of which isoforms have a CED3/ICE homology region which has proteolytic activity (proteolytic domain), and causes the death of cells when expressed in the cells. Thus, activation of this novel CED3/ICE homolog (i.e., the various MACH isoforms having the proteolytic domain) by FAS-R (via MORT-1 interaction) appears to constitute an effector component of the FAS-R-mediated cell-death pathway.

Moreover, MACH also appears to function as an effector component of the cell-death pathway initiated by the binding of TNF to p55-R at the cell surface, this by way of indirect mechanism of MORT-1 binding to TRADD, a protein which binds to the intracellular domain of p55-R (Hsu et al, 1995), followed by or together with MACH binding to MORT-1, with the activation of MACH into an active protease involved in effecting cell death.

It should also be noted that while MACH, in particular, the MACHα1 isoform, displays all of the sequence features critical of the function of the CED3/ICE proteases, it does, however, have some distinctive sequence features of its own which may endow it with a unique and possibly tissue/cell specific mode of action.

MORT-1 (for 'Mediator of Receptor Toxicity', Boldin et al, 1995b), previously designated HF1, is capable of binding to the intracellular domain of the FAS-R. This FAS-IC-binding protein appear to act as a mediator or modulator of the FAS-R ligand effect on cells by way of mediating or modulating the intracellular signaling process which usually occurs following the binding of the FAS-R ligand at the cell surface. In addition to its FAS-IC-binding specificity, MORT-1 was shown to have other characteristics (see Example 1), for example, it has a region homologous to the "death domain" (DD) regions of the p55-TNF-R and FAS-R (p55-DD and FAS-DD), and thereby is also capable of self-association.

MORT-1 is also capable of activating cell cytotoxicity on its own, an activity possibly related to its self-association capability. It has now also been found that co-expression of the region in MORT-1 (HF1) that contains the "death domain" homology sequence (MORT-DD, present in the C-terminal part of MORT-1) strongly interferes with FAS-induced cell death, as would be expected from its ability to bind to the "death domain" of the FAS-IC. Further, in the same experimental conditions, it was found that co-expression of the part of MORT-1 that does not contain the MORT-DD region (the N-terminal part of MORT-1, amino acids 1-117, "MORT-1 head") resulted in no interference of the FAS-induced cell death and, if at all, a somewhat enhanced FAS-induced cell cytotoxicity.

Accordingly, it is likely that MORT-1 also binds to other proteins involved in the intracellular signaling process. These MORT-1-binding proteins may therefore also act as indirect mediators or modulators of the FAS-R ligand effect on cells by way of mediating or modulating the activity of MORT-1; or these MORT-1-binding proteins may act directly as mediators or modulators of the MORT-1-associated intracellular signaling process by way of mediating or modulating the activity of MORT-1, which, as noted above, has an apparently independent ability to activate cell cytotoxicity. These MORT-1-binding proteins may also be used in any of the standard screening procedures to isolate, identify and characterize additional proteins, peptides, factors, antibodies, etc., which may be involved in the MORT-1-associated or FAS-R-associated signaling process or may be elements of other intracellular signaling processes. Such MORT-1-binding proteins have been isolated and are described herein (see Example 2 and Example 3). One of these MORT-1-binding proteins, herein designated MACH, was initially cloned, sequenced, and partially characterized as having the following properties: The MACH cDNA encodes the ORF-B open-reading frame; MACH binds to MORT-1 in a very strong and specific manner; the MACH binding site in MORT-1 occurs upstream of the MORT-1 "death domain" motif; the ORF-B region of MACH is the MORT-1-interacting part thereof; and MACH is capable of self-association and of inducing cell-cytotoxicity on its own.

In accordance with the present invention, it has now been shown as mentioned above, that MACH actually exists in a number of isoforms. Moreover, the MACH ORF-B noted above is in fact one of the MACH isoforms designated herein as MACHβ1 (see below).

Accordingly, the present invention provides a DNA sequence encoding a protein, analogs or fragments thereof, capable of binding to or interacting with MORT-1, said protein, analogs or fragments thereof being capable of mediating the intracellular effect mediated by the FAS-R or p55-TNF-R.

In particular, the present invention provides a DNA sequence selected from the group consisting of:
(a) a cDNA sequence derived from the coding region of a native MORT-1 binding protein;
(b) DNA sequences capable of hybridization to a sequence of (a) under moderately stringent conditions and which encode a biologically active MORT-1 binding protein; and
(c) DNA sequences which are degenerate as a result of the genetic code to the DNA sequences defined in (a) and (b) and which encode a biologically active MORT-1 binding protein.

Another specific embodiment of the above DNA sequence of the invention is a DNA sequence comprising at least part of the sequence encoding at least one isoform of the MACH protein selected from the herein designated MACH isoforms MACHα1, MACHα2, MACHα3, MACHβ2, MACHβ1, MACHβ3, MACHβ4 and MACHβ5.

Other specific embodiments of the DNA sequence of the invention as noted above are DNA sequences encoding:
(a) a MACH isoform selected from MACHα1, MACHα1 and MACHβ3 having an amino acid sequence set forth in SEQ ID NOs: 7, 5 and 8 respectively, and analogs and fragments of any one thereof;
(b) MACHα1 having the amino acid sequence set forth in SEQ ID NO:7, and analogs and fragments thereof;
(c) MACHβ1 having the amino acid sequence set forth in SEQ ID NO:5, and analogs and fragments thereof;
(d) MACHβ3 having the amino acid sequence set forth in SEQ ID NO:8, and analogs and fragments thereof.

In the present invention provides MORT-1-binding proteins, and analogs, fragments or derivatives thereof encoded by any of the above sequences of the invention, said proteins, analogs, fragments and derivatives being capable of binding to or interacting with MORT-1 and mediating the intracellular effect mediated by the FAS-R or p55 TNF-R.

A specific embodiment of the invention is the MORT-1-binding protein, analogs fragments and derivatives thereof, which are selected from as least one isoform of MACH of the group comprising MACHα1, MACHα2, MACHα3, MACHβ1, MACHβ2, MACHβ3, MACHβ4 and MACHβ5 which have at least part of the amino acid sequences thereof.

Also provided by the present invention are vectors encoding the above MORT-1-binding protein, and analogs, fragments or derivatives of the invention, which contain the above DNA sequence of the invention; these vectors being capable of being expressed in suitable eukaryotic or prokaryotic host cells; transformed eukaryotic or prokaryotic host cells containing such vectors; and a method for producing the MORT-1-binding protein, or analogs, fragments or derivatives of the invention by growing such transformed host cells under conditions suitable for the expression of said protein, analogs, fragments or derivatives, effecting post-translational modifications of said protein as necessary for obtaining said protein and extracting said expressed protein, analogs, fragments or derivatives from the culture medium of said transformed cells or from cell extracts of said transformed cells. The above definitions are intended to include all isoforms of the MACH protein.

In another aspect, the present invention also provides antibodies or active derivatives or fragments thereof specific to the MORT-1-binding protein, and analogs, fragments and derivatives thereof, of the invention.

By yet another aspect of the invention, there are provided various uses of the above DNA sequences or the proteins which they encode, according to the invention, which uses include amongst others:
(i) A method for the modulation of the FAS-R ligand or TNF effect on cells carrying a FAS-R or p55-R; comprising treating said cells with one or more MORT-1-binding proteins, analogs, fragments or derivatives of the invention, capable of binding to MORT-1, which binds to the intracellular domain of FAS-R, or capable of binding to MORT-1 which binds to TRADD which binds to the intracellular domain of p55-R, and thereby being capable of modulating/mediating the activity of said FAS-R or p55 TNF-R, wherein said treating of said cells comprises introducing into said cells said one or more proteins, analogs, fragments or derivatives in a form suitable for intracellular introduction thereof, or introducing into said cells a DNA sequence encoding said one or more proteins, analogs, fragments or derivatives in the form of a suitable vector carrying said sequence, said vector being capable of effecting the insertion of said sequence into said cells in a way that said sequence is expressed in said cells.

(ii) A method for the modulation of the FAS-R ligand or TNF effect on cells according to (i) above, wherein said treating of cells comprises introducing into said cells said MORT-1-binding protein, or analogs, fragments or derivatives thereof, in a form suitable for intracellular introduction, or introducing into said cells a DNA sequence encoding said MORT-1-binding protein, or analogs, fragments or derivatives in the form of a suitable vector carrying said sequence, said vector being capable of effecting the insertion of said sequence into said cells in a way that said sequence is expressed in said cells.

(iii) A method as in (ii) above wherein said treating of said cells is by transfection of said cells with a recombinant animal virus vector comprising the steps of:
  (a) constructing a recombinant animal virus vector carrying a sequence encoding a viral surface protein (ligand) that is capable of binding to a specific cell surface receptor on the surface of a FAS-R- or p55-R-carrying cell and a second sequence encoding a protein selected from MORT-1-binding protein, and analogs, fragments and derivatives thereof, that when expressed in said cells is capable of modulating/mediating the activity of said FAS-R or p55-R; and
  (b) infecting said cells with said vector of (a).

(iv) A method for modulating the FAS-R ligand or TNF effect on cells carrying a FAS-R or a p55-R comprising treating said cells with antibodies or active fragments or derivatives thereof, according to the invention, said treating being by application of a suitable composition containing said antibodies, active fragments or derivatives thereof to said cells, wherein when the MORT-1-binding protein, or portions thereof of said cells are exposed on the extracellular surface, said composition is formulated for extracellular application, and when said MORT-1-binding proteins are intracellular, said composition is formulated for intracellular application.

(v) A method for modulating the FAS-R ligand or TNF effect on cells carrying a FAS-R or p55-R comprising treating said cells with an oligonucleotide sequence encoding an anti-sense sequence of at least part of the MORT-1-binding protein sequence of the invention, said oligonucleotide sequence being capable of blocking the expression of the MORT-1-binding protein.

(vi) A method as in (ii) above for treating tumor cells or HIV-infected cells or other diseased cells, comprising:
  (a) constructing a recombinant animal virus vector carrying a sequence encoding a viral surface protein capable of binding to a specific tumor cell surface receptor or HIV-infected cell surface receptor or receptor carried by other diseased cells and a sequence encoding a protein selected from MORT-1-binding protein, analogs, fragments and derivatives of the invention, that when expressed in said tumor, HIV-infected, or other diseased cell is capable of killing said cell; and
  (b) infecting said tumor or HIV-infected cells or other diseased cells with said vector of (a).

(vii) A method for modulating the FAS-R ligand or TNF effect on cells comprising applying the ribozyme procedure in which a vector encoding a ribozyme sequence capable of interacting with a cellular mRNA sequence encoding a MORT-1-binding protein according to the invention, is introduced into said cells in a form that permits expression of said ribozyme sequence in said cells, and wherein when said ribozyme sequence is expressed in said cells it interacts with said cellular mRNA sequence and cleaves said mRNA sequence resulting in the inhibition of expression of said MORT-1-binding protein in said cells.

(viii) A method selected from the method according to the invention, wherein said MORT-1-binding protein encoding sequence comprises at least one of the MACH isoforms, analogs, fragments and derivatives of any thereof according to the invention which are capable of binding specifically to MORT-1 which in turn binds specifically to FAS-IC, or which are capable of binding to MORT-1 which in turn binds to TRADD and which in turn binds to the p55-IC.

(ix) A method for isolating and identifying proteins, according to the invention; capable of binding to the MORT-1 protein, comprising applying the yeast two-hybrid procedure in which a sequence encoding said MORT-1 protein is carried by one hybrid vector and sequence from a cDNA or genomic DNA library is carried by the second hybrid vector, the vectors then being used to transform yeast host cells and the positive transformed cells being isolated, followed by extraction of the said second hybrid vector to obtain a sequence encoding a protein which binds to said MORT-1 protein, said protein being the MORT-1-binding proteins.

(x) A method according to any one of (i)-(ix) above wherein said MORT-1-binding protein is the MACH isoform herein designated MACHα1, analogs, fragments and derivatives thereof.

(xi) A method according to any one of (i)-(ix) above wherein said MORT-1-binding protein is the MACH isoform herein designated MACHβ1, analogs, fragments and derivatives thereof.

(xii) A method according to any one of (i)-(ix) above wherein said MORT-1-binding protein is the MACH isoform herein designated MACHβ3, analogs, fragments and derivatives thereof.

The present invention also provides a pharmaceutical composition for the modulation of the FAS-R ligand- or TNF-effect on cells comprising, as active ingredient any one of the following:
  (i) a MORT-1-binding protein according to the invention, and biologically active fragments, analogs, derivatives or mixtures thereof;
  (ii) a recombinant animal virus vector encoding a protein capable of binding a cell surface receptor and encoding a MORT-1-binding protein or biologically active fragments or analogs, according to the invention;
  (iii) an oligonucleotide sequence encoding an anti-sense sequence of the MORT-1-binding protein sequence according to the invention, wherein said oligonucleotide may be the second sequence of the recombinant animal virus vector of (ii) above.

The present invention also provides:

I. a method for the modulation of the MORT-1-induced effect or MORT-1-binding protein-induced effect on cells comprising treating said cells in accordance with a method of any one of (i)-(xi) above; with MORT-1-binding proteins, analogs, fragments or derivatives thereof or with sequences encoding MORT-1-binding proteins, analogs or fragments thereof, said treatment resulting in the enhancement or inhibition of said MORT-1-mediated effect, and thereby also of the FAS-R or p55-R-mediated effect.

II. a method as above wherein said MORT-1-binding protein, analog, fragment or derivative thereof is that part of the MORT-1-binding protein which is specifically involved in binding to MORT-1 or MORT-1-binding protein itself, or said MORT-1-binding protein sequence encodes that part of MORT-1-binding protein which is specifically involved in binding to MORT-1 or the MORT-1-binding protein itself.

III. A method as above wherein said MORT-1-binding protein is any one of the MACH isoforms selected from MACHα1, MACHβ1, and MACHβ3, said MACH isoforms capable of enhancing the MORT-1-associated effect on cells and thereby also of enhancing the FAS-R- or p55-R-associated effect on cells.

As arises from all the above-mentioned, as well as from the detailed description hereinbelow, MACH may be used in a MORT-1 independent fashion to treat cells or tissues. Isolation of the MORT-1-binding proteins, their identification and characterization may be carried out by any of the standard screening techniques used for isolating and identifying proteins, for example, the yeast two-hybrid method, affinity chromatography methods, and any of the other well-known standard procedures used for this purpose.

Other aspects and embodiments of the present invention are also provided as arising from the following detailed description of the invention.

It should be noted that, where used throughout, the following terms: "Modulation of the FAS-ligand or TNF effect on cells"; and "Modulation of the MORT-1 or MORT-1-binding protein effect on cells" are understood to encompass in vitro as well as in vivo treatment.

BRIEF DESCRIPTION OF THE DRAWINGS

FIG. 1 shows the interaction of MORT-1 with FAS-IC and the self-association of MORT-1 within transformed yeasts as assessed by a two-hybrid β-galactosidase expression test.

FIG. 2 depicts schematically the preliminary nucleotide (SEQ ID NO:1) and deduced amino acid sequence (SEQ ID NO:2) of MORT-1 (HF1) in which the death domain is underlined as is a possible translation start site, i.e., the underlined methionine residue at position 49 (bold, underlined M). The asterisk indicates the translation stop codon (nucleotides 769-771). At the beginning and in the middle of each line are provided two numerals depicting the relative positions of the nucleotides and amino acids of the sequence with respect to the start of the sequence (5' end), in which the first numeral denotes the nucleotide and the second numeral denoted the amino acid.

FIG. 3 is a preliminary partial nucleotide sequence (SEQ ID NO:3) encoding a MORT-1-binding protein as obtained from a cDNA clone.

FIGS. 4A-C depict schematically the MACH cDNA and its encoded protein, wherein in FIG. 4A there is shown the structure of the MACH cDNA which encodes two MACH open-reading frames (ORF-A and ORF-B), the hatched area of ORF-B indicating the region thereof having homology with the MORT-1 protein; in FIG. 4B, there is shown the deduced amino acid sequence (SEQ ID NO:5) for the MACH ORF-B region, the underlined amino acid residues being the region having homology with MORT-1 (corresponding to the hatched region of FIG. 4A); and in FIG. 4C, there is shown the nucleotide sequence (SEQ ID NO:4) of the entire MACH cDNA molecule (designated MACHβ1).

FIGS. 7A and 7B show the amino acid sequence (SEQ ID NO:5) of MACHβ1 (FIG. 7A). FIG. 7B shows the sequence homology of the MORT module in MACHβ1. MORT-1 and PEA-15 (SEQ ID NO:6).

FIG. 9A shows the assessment of the expression of the proteins and their molecular sizes by immunoprecipitation from cell lysates using anti-FLAG antibody. FIG. 9B shows affinity binding of the proteins to GST-MORT-1, adsorbed to glutathione-agarose beads (or, as a control, to GST or GST-fused to the intracellular domain of Fas-APO1). FIG. 9C shows the results of the immunoprecipitations of the various MORT-1 and MACH fusion constructs using the various specific antibodies.

FIG. 11 is a schematic colinear amino acid sequence alignment of the MACH isoforms, MACHα1 (SEQ ID NO:7), MACHβ1 (SEQ ID NO:5), and MACHβ3 (SEQ ID NO:8) and the various known members of the CED3/ICE protease family, CED-3 (SEQ ID NO:9), Ich-11/Nedd2 (SEQ ID NO:10), $ICE_{rel}III$ (SEQ ID NO:11), Tx/Ich2/$ICE_{rel}II$ (SEQ ID NO:12), ICE (SEQ ID NO:13), CPP-32 (SEQ ID NO:30), Mcn2α (SEQ ID NO:31). Amino acid residues are numbered both to the left and to the right of each sequence. Dotted lines; gaps in the sequence to allow optimal alignment. Amino acids that are identical in at least three of the members of the CED3/ICE protease family show are boxed. The MORT modules upstream to CED3/ICE homology region are boxed. Sites of C-terminal deletions employed in this study are denoted by broken lines. The four amino acid blocks downstream to the MORT module region, which vary among the various MACH isoforms (blocks 1-4) are denoted by overlinings. Within the CED3/ICE homology region, amino acids aligning with residues within ICE implicated in catalytic activity by X-ray crystal analysis are denoted as follow: The residues putatively involved in catalysis, corresponding to $His_{237}$, $Gly_{238}$ and $Cys_{285}$ in ICE are marked by closed circles below the alignment ●). The residues constituting the binding pocket for the carboxylate side chain of the P1 Asp, corresponding to $Arg_{179}$, corresponding to $Arg_{179}$, $Gln_{283}$, $Arg_{34}$, and $Ser_{347}$ in ICE, are marked by open circles below the alignment (○). The Ala residues upstream to the residues corresponding to $Cys_{285}$ in ICE, and the Arg and Gly residues downstream to this Cys, which are conserved in all previously described proteases of the CED3/ICE family. Residues proximal to $P_1$-$P_4$ residues of the substrate are marked by triangles below the alignment (Δ). Known and previously suspected Asp-X cleavage sites and potential sites of cleavage found at similar locations in MACH are boxed. Arrows indicate the N- and C-terminal ends of the p20 and p10 subunits of ICE and of the p17 and p12 subunits of CPP32. The C-termini of the proteins are denoted by asterisks (*).

(FIG. 12A), 30 min. (FIG. 12B), 60 min. (FIG. 12C), 90 min. (FIG. 12D), 180 min. (FIG. 12E). FIG. 12F shows the proteolytic activity over time at a specific concentration of substrate.

DETAILED DESCRIPTION OF THE INVENTION

Figure 5:
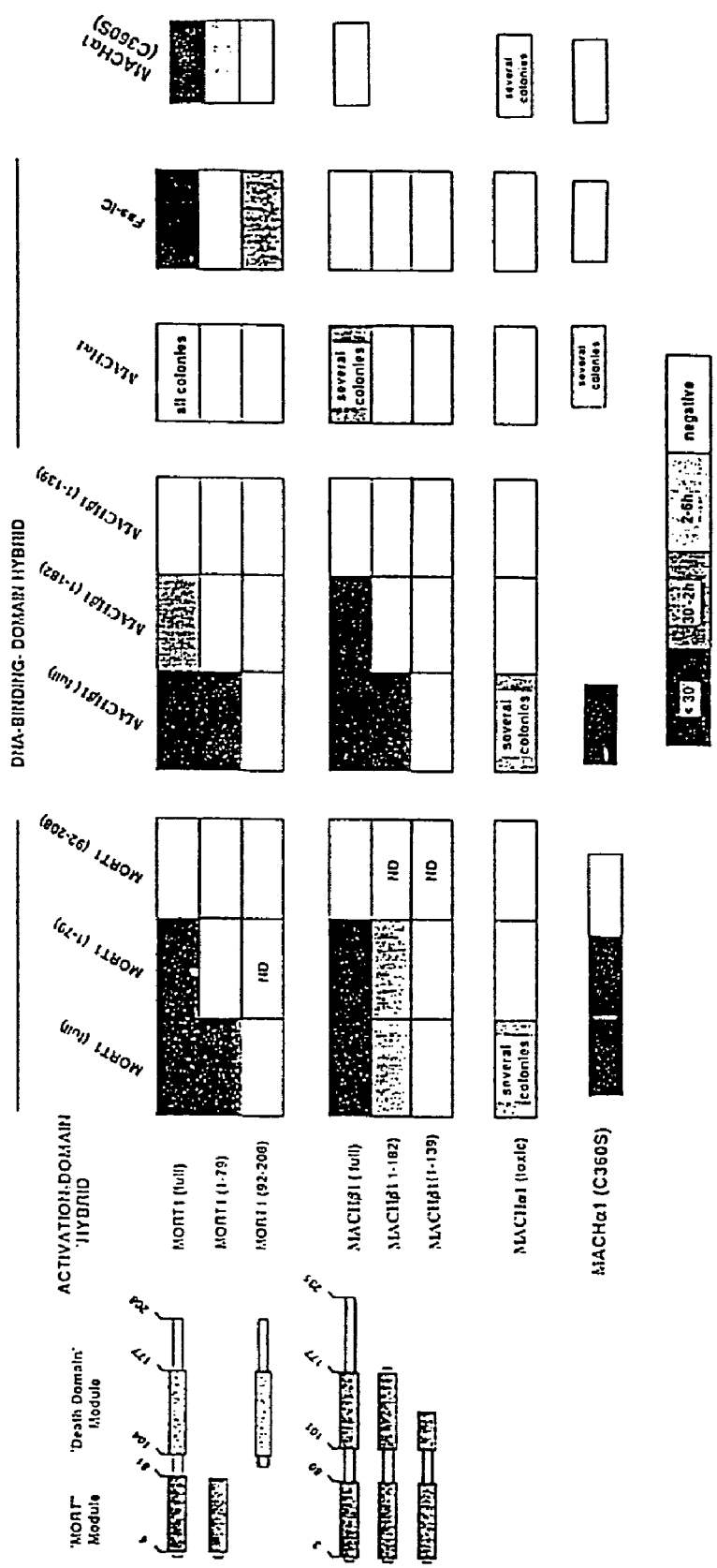
FIG. 5 depicts the results illustrating the interaction of MORT-1 and MACH within transfected yeast cells.

The present invention relates, in one aspect, to novel MORT-1-binding proteins which are capable of binding to or interacting with MORT-1 and thereby of binding to the intracellular domain of the FAS-R receptor, to which MORT-1 binds, or of binding to the intracellular domain of the p55 TNF-R, to which the protein TRADD (see Example 2 and as noted above) binds and to which TRADD protein MORT-1 binds. Hence, the MORT-1 binding proteins of the present invention are considered as mediators or modulators of FAS-R, having a role in, for example, the signaling process that is initiated by the binding of FAS ligand to FAS-R, and likewise also having a role in the signaling process that is initiated by the binding of TNF to p55-R. Of the MORT-1-binding proteins of the present invention are included the newly discovered MACH isoforms, the amino acid and DNA sequences of which are new sequences not appearing in the 'GENBANK' or 'PROTEIN BANK' data banks of DNA or amino acid sequences.

More particularly, in accordance with the present invention, several mammalian homologs of the nematode protease, CED3 have been disclosed. These have been designated as MACH isoforms (MACHα and MACHβ isoforms) which, although being closely related, do however display some differences of structure and of substrate specificity, and as such may serve somewhat different functions in mammalian cells. Indeed, two different activities of the proteases are known. The main role of ICE seems to be the processing of the IL-1β precursor, while CED3 has been clearly shown to serve as an effector of programmed cell death. This latter role also appears to be the role of at least some of the mammalian homologs (some MACH isoforms). The amino acid sequence of MACHα1 shows closest resemblance to CPP32, the closest known mammalian homolog of CED3. The substrate specificity of MACH is also similar to that of CPP32, except that MACHα1 seems to have a more restricted substrate specificity than that of CPP32. CPP32 cleaves preferentially the substrate peptide corresponding to a cleavage site in poly (ADP ribose) polymerase (PARP), yet also has some proteolytic activity against the peptide corresponding to the ICE cleavage site in the IL-1β precursor. MACHα1 seems, however, to be solely capable of cleaving the PARP-derived sequence. These relationships of MACHα1 to CPP32 and CED3, and its dissimilarities to ICE, are consistent with the idea that MACHα1 serves, similarly to CED3, as regulator of cell death. MACHα1 displays, though, some sequence features which distinguish it from CED3 and from CPP32, as well as from all other members of the CED3/ICE family. The C terminal part of MACHα1, upstream to its CED3/ICE homology region, shows no resemblance at all to the upstream region of any of the other homologs. There are also some unique sequence features to the CED3/ICE homology region of the protein. These differences suggest that MACHα1 belongs to a distinct evolutionary branch of the family and that its contribution to cell death somewhat differs from that of the previously described CED3/ICE homologs.

One important difference may concern the way in which the function of the protease is regulated. Being involved both in developmentally related cell death processes and in receptor-induced immune cytolysis, the cleavage of proteins by proteases of the CED3/ICE family should be amenable to regulation both by signals that are formed within the cell and by signals emanating from cell surface receptors. In developmental cell death processes, the activation of such proteases seems to involve mechanisms that affect gene expression, resulting in enhanced synthesis of the proteases, as well as in decreased synthesis of proteins like BCL-2, that antagonize their apoptopic effect. This is clearly not the case, however, for the cytotoxicity triggered by FAS-R or the TNF receptors. Cells can be killed by TNF or the FAS-R ligand even when their protein synthesis activity is fully blocked (they are in fact killed more effectively then) and remain stimulus-dependent under these conditions. Activation of proteases of the CED3/ICE family by the TNF receptors and FAS-R may thus occur by a mechanism which is protein-synthesis-independent. The unique sequence properties of MACHα1 may allow it to take part in such a mechanism.

To applicants' knowledge, no other protease has so far been found to associate, either directly or through an adapter protein, with the intracellular domain of a cell surface receptor. Yet by inference from the way of action of receptor-associated proteins that have other enzymatic activities, it seems plausible that the binding of MACHα1 to MORT1 allows stimulation of the MACHα1 protease-activity upon triggering of FAS-R. It may also allow activation of the protease by the p55-R, through the binding of MORT1 to TRADD, which binds to p55-R.

Other members of the CED3/ICE family were found to exhibit full activity only after proteolytic processing, which occurs either by their self-cleavage or by effects of other proteases of this family (reviewed in Kumar, 1995; Henkart, 1996). The cytotoxic effect resulting from co-expression of the two major potential self-cleavage products of MACHα1, as opposed to the lack of cytotoxicity in cells that express the possibility that also MACHα1 gains full activity only after its processing. The enzymatic activity observed in lysates of bacteria that express the full length region apparently reflect self processing of the protein produced under these conditions or processing by some bacterial proteases. In what way this processing occurs within the mammalian cell, and how it can be brought about by triggering of FAS-R and p55-R, is not known, nor is it clear yet what relative contribution the protease activity of MACHα1 makes to the FAS-R- and TNF-induced cytotoxicity. Evaluation of this contribution is complicated by the fact that also expression of MACHβ1, which lacks the CED3/ICE homology region, results in marked cytotoxicity. Presumably, this cytotoxicity reflects the ability of MACHβ1 to bind to MACHα1. Due to this ability, transfected MACH molecules may impose, upon aggregation, a conformational change in the MACHα1 molecules that are endogenous to the transfected cell. Such a mechanism may well account also for the cytotoxicity observed when molecules that act upstream to MACH, (MORT1, TRADD or the death domains of either the p55-R or FAS-R) are over-expressed in cells. At the moment, however, one cannot exclude that the cytotoxicity observed upon induced expression of MACH or of molecules that act upstream to it reflect, besides the proteolytic activity of the CED3/ICE homology region in MACH, also activation of some of the other mechanisms believed to take part in the FAS-R and p55-R cytotoxic effect (for example, activation of the neutral or acid sphingomyelinase). One also cannot exclude that the proteolytic activity of the CED3/ICE homology region serves other functions besides cytotoxicity induction. A clearer idea of the function of MACHα1 should be gained by identification of the endogenous substrate proteins that are cleaved upon activation of MACHα1. Finding ways to ablate the activity of MACHα1 at will, for example by expression of inhibitory molecules, will also contribute to understanding of the function of this protein, and serve as a way for regulating its activity when desired.

There may well exist within cells that express MACHα1 natural inhibitors of the protease encompassed in this protein. Existence of alternatively spliced isoforms for some of the other members of the CED3/ICE family has been shown to constitute a way of physiological restriction of the function of these proteases. Some of the isoforms of these other proteases were reported to act as natural inhibitors of the full-length isoforms, apparently by forming inactive heterodimers, with them. This may well be the case also for some isoforms of MACH, for example, MACHα3, in which the potential N-terminal cleavage site is missing and MACHα1 mutants whose CED3/ICE homology region is deficient. Expression of such inhibitory isoforms may constitute a mechanism of cellular self-protection against the FAS-R and TNF cytotoxicity. The wide heterogeneity of MACH isoforms, which greatly exceeds the heterogeneity observed for any of the other proteases of the CED3/ICE family, may allow a particularly refined tuning of the function of the active form of this protein. It seems also possible that some of the MACH isoforms serve other functions. The ability of MACHβ1 to bind both to MORT1 and to MACHα1 raises the possibility that some of these isoforms, and perhaps also other MACH isoforms, do not have an inhibitory but rather an enhancing effect on the function of the enzymatically active isoforms. It seems also possible that some isoforms do not serve a role related to cytotoxicity, but rather act as docking sites for molecules that are involved in other, non-cytotoxic, effects of FAS-R and TNF.

Due to the unique ability of FAS-R and the TNF receptors to cause cell death, as well as the ability of the TNF receptors to trigger various other tissue-damaging activities, aberration of the function of these receptors can be particularly deleterious to the organism. Indeed, both excessive and deficient function of these receptors have been shown to contribute to the pathological manifestations of various diseases. Identifying molecules that take part in the signaling activity of these receptors, and finding ways to modulate the function of these molecules, constitutes a potential clue for new therapeutical approaches to these diseases. In view of the suspected central role of MACHα1 in FAS-R and TNF toxicity, it seems particularly important to design drugs that can block the proteolytic function of this molecule, as has been done for some other members of the CED3/ICE family. The unique sequence features of the CED3/ICE homolog encompassed in the MACHα1 molecules may allow designing drugs that can affect its protection from excessive immune-mediated cytotoxicity without interfering with physiological cell death processes, in which other members of the CED3/ICE family are involved.

Thus, the present invention also concerns the DNA sequence encoding a MORT-1-binding protein and the MORT-1-binding proteins encoded by the DNA sequences.

Moreover, the present invention further concerns the DNA sequences encoding biologically active analogs, fragments and derivatives of the MORT-1-binding protein, and the analogs, fragments and derivatives encoded thereby. The preparation of such analogs, fragments and derivatives is by standard procedure (see for example, Sambrook et al, 1989) in which in the DNA sequences encoding the MORT-1-binding protein, one or more codons may be deleted, added or substituted by another, to yield analogs having at least one amino acid residue change with respect to the native protein.

A polypeptide or protein "substantially corresponding" to MORT-1-binding protein includes not only MORT-1-binding protein but also polypeptides or proteins that are analogs of MORT-1-binding.

Analogs that substantially correspond to MORT-1-binding protein are those polypeptides in which one or more amino acid of the MORT-1-binding protein's amino acid sequence has been replaced with another amino acid, deleted and/or inserted, provided that the resulting protein exhibits substantially the same or higher biological activity as the MORT-1-binding protein to which it corresponds.

In order to substantially correspond to MORT-1-binding protein, the changes in the sequence of MORT-1-binding proteins, such as MACH isoforms are generally relatively minor. Although the number of changes may be more than ten, preferably there are no more than ten changes; more preferably no more than five, and most preferably no more than three such changes. While any technique can be used to find potentially biologically active proteins which substantially correspond to MORT-1-binding proteins, one such technique is the use of conventional mutagenesis techniques on the DNA encoding the protein, resulting in a few modifications. The proteins expressed by such clones can then be screened for MORT-1 binding and/or FAS-R and p55-R mediating activity.

"Conservative" changes are those changes which would not be expected to change the activity of the protein and are usually the first to be screened as these would not be expected to substantially change the size, charge or configuration of the protein and thus would not be expected to change the biological properties thereof.

Conservative substitutions of MORT-1-binding proteins include an analog wherein at least one amino acid residue in the polypeptide has been conservatively replaced by a different amino acid. Such substitutions preferably are made in accordance with the following list as presented in Table IA, which substitutions may be determined by routine experimentation to provide modified structural and functional properties of a synthesized polypeptide molecule while maintaining the biological activity characteristic of MORT-1-binding protein.

TABLE IA

| Original Residue | Exemplary Substitution |
|---|---|
| Ala | Gly; Ser |
| Arg | Lys |
| Asn | Gln; His |
| Asp | Glu |
| Cys | Ser |
| Gln | Asn |
| Glu | Asp |
| Gly | Ala; Pro |
| His | Asn; Gln |
| Ile | Leu; Val |
| Leu | Ile; Val |
| Lys | Arg; Gln; Glu |
| Met | Leu; Tyr; Ile |
| Phe | Met; Leu; Tyr |
| Ser | Thr |
| Thr | Ser |
| Trp | Tyr |
| Tyr | Trp; Phe |
| Val | Ile; Leu |

Alternatively, another group of substitutions of MORT-1-binding protein are those in which at least one amino acid residue in the polypeptide has been removed and a different residue inserted in its place according to the following Table IB. The types of substitutions which may be made in the polypeptide may be based on analysis of the frequencies of amino acid changes between a homologous protein of different species, such as those presented in Table 1-2 of Schulz et al (1979), and FIGS. 3-9 of Creighton (1983). Based on such an analysis, alternative conservative substitutions are defined herein as exchanges within one of the following five groups:

TABLE IB

1. Small aliphatic, nonpolar or slightly polar residues: Ala, Ser, Thr (Pro, Gly);
2. Polar negatively charged residues and their amides: Asp, Asn, Glu, Gln;
3. Polar, positively charged residues: His, Arg, Lys;
4. Large aliphatic nonpolar residues: Met, Leu, Ile, Val (Cys); and
5. Large aromatic residues: Phe, Tyr, Trp.

The three amino acid residues in parentheses above have special roles in protein architecture. Gly is the only residue lacking any side chain and thus imparts flexibility to the chain. This however tends to promote the formation of secondary structure other than α-helical. Pro, because of its unusual geometry, tightly constrains the chain and generally tends to promote β-turn-like structures, although in some cases Cys can be capable of participating in disulfide bond formation which is important in protein folding. Note that Schulz et al, supra, would merge Groups 1 and 2, above. Note also that Tyr, because of its hydrogen bonding potential, has significant kinship with Ser, and Thr, etc.

Conservative amino acid substitutions according to the present invention, e.g., as presented above, are known in the art and would be expected to maintain biological and structural properties of the polypeptide after amino acid substitution. Most deletions and substitutions according to the present invention are those which do not produce radical changes in the characteristics of the protein or polypeptide molecule. "Characteristics" is defined in a non-inclusive manner to define both changes in secondary structure, e.g. α-helix or β-sheet, as well as changes in biological activity, e.g., binding of MORT-1 or mediation of FAS-R ligand or TNF effect on cells.

Examples of production of amino acid substitutions in proteins which can be used for obtaining analogs of MORT-1-binding proteins for use in the present invention include any known method steps, such as presented in U.S. Pat. No. RE 33,653, U.S. Pat. Nos. 4,959,314, 4,588,585 and 4,737,462, to Mark et al; 5,116,943 to Koths et al, 4,965,195 to Namen et al; 4,879,111 to Chong et al; and 5,017,691 to Lee et al; and lysine substituted proteins presented in U.S. Pat. No. 4,904,584 (Shaw et al).

Besides conservative substitutions discussed above which would not significantly change the activity of MORT-1-binding protein, either conservative substitutions or less conservative and more random changes, which lead to an increase in biological activity of the analogs of MORT-1-binding proteins, are intended to be within the scope of the invention.

When the exact effect of the substitution or deletion is to be confirmed, one skilled in the art will appreciate that the effect of the substitution(s), deletion(s), etc., will be evaluated by routine binding and cell death assays. Screening using such a standard test does not involve undue experimentation.

Acceptable analogs are those which retain at least the capability of binding to MORT-1, and thereby, as noted above mediate the activity (e.g., by the protease activity of at least some of the MACH isoforms) of the FAS-R and p55-R. In such a way, analogs can be produced which have a so-called dominant-negative effect, namely, an analog which is defective either in binding to MORT-1, or in subsequent signaling or protease activity following such binding. Such analogs can be used, for example, to inhibit the FAS-ligand-effect by competing with the natural MORT-1-binding proteins. For example, it appears likely that the MACH isoforms, MACHα2 and MACHα3 are "natural" analogs which serve to inhibit MACH activity by competing with the binding of the active (protease) MACH isoforms to MORT-1 which appears to be essential for the activation of these MACH isoforms. Once the active MACH isoforms cannot bind to MORT-1, the intracellular signaling pathways mediated by FAS-R and p55-R will thereby also be inhibited. Likewise, so-called dominant-positive analogs may be produced which would serve to enhance the FAS ligand or TNF effect. These would have the same or better MORT-1-binding properties and the same or better signaling properties of the natural MORT-1-binding proteins.

At the genetic level, these analogs are generally prepared by site-directed mutagenesis of nucleotides in the DNA encoding the MORT-1-binding protein, thereby producing DNA encoding the analog and thereafter synthesizing the DNA and expressing the polypeptide in recombinant cell culture. The analogs typically exhibit the same or increased qualitative biological activity as the naturally occurring protein, Ausubel et al (1987-1995); Sambrook et al (1989).

Preparation of a MORT-1-binding protein in accordance herewith, or an alternative nucleotide sequence encoding the same polypeptide but differing from the natural sequence due to changes permitted by the known degeneracy of the genetic code, can be achieved by site-specific mutagenesis of DNA that encodes an earlier prepared analog or a native version of a MORT-1-binding protein. Site-specific mutagenesis allows the production of analogs through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 complementing nucleotides on each side of the sequence being altered. In general, the technique of site-specific mutagenesis is well known in the art, as exemplified by publications such as Adelman et al (1983), the disclosure of which is incorporated herein by reference.

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al (1981), the disclosure of which is incorporated herein by reference. These phage are readily available commercially and their use is generally well known to those skilled in the art. Alternatively, plasmid vectors that contain a single-stranded phage origin of replication (Veira et al, 1987) may be employed to obtain single-stranded DNA.

In general, site-directed mutagenesis in accordance herewith is performed by first obtaining a single-stranded vector that includes within its sequence a DNA sequence that encodes the relevant polypeptide. An oligonucleotide primer bearing the desired mutated sequence is prepared synthetically by automated DNA/oligonucleotide synthesis. This primer is then annealed with the single-stranded protein-sequence-containing vector, and subjected to DNA-polymerizing enzymes such as E. coli polymerase I Klenow fragment, to complete the synthesis of the mutation-bearing strand. Thus, a mutated sequence and the second strand bear the desired mutation. This heteroduplex vector is then used to transform appropriate cells, such as E. Coli JM101 cells, and clones are selected that include recombinant vectors bearing the mutated sequence arrangement.

After such a clone is selected, the mutated MORT-1-binding protein may be removed and placed in an appropriate vector, generally a transfer or expression vector of the type that may be employed for transfection of an appropriate host.

Accordingly, gene or nucleic acid encoding for a MORT-1-binding protein can also be detected, obtained and/or modified, in vitro, in situ and/or in vivo, by the use of known DNA or RNA amplification techniques, such as PCR and chemical oligonucleotide synthesis. PCR allows for the amplification (increase in number) of specific DNA sequences by repeated DNA polymerase reactions. This reaction can be used as a replacement for cloning; all that is required is a knowledge of the nucleic acid sequence. In order to carry out PCR, primers are designed which are complementary to the sequence of interest. The primers are then generated by automated DNA synthesis. Because primers can be designed to hybridize to any part of the gene, conditions can be created such that mismatches in complementary base pairing can be tolerated. Amplification of these mismatched regions can lead to the synthesis of a mutagenized product resulting in the generation of a peptide with new properties (i.e., site directed mutagenesis). See also, e.g., Ausubel, supra, Ch. 16. Also, by coupling complementary DNA (cDNA) synthesis, using reverse transcriptase, with PCR, RNA can be used as the starting material for the synthesis of the extracellular domain of a prolactin receptor without cloning.

Furthermore, PCR primers can be designed to incorporate new restriction sites or other features such as termination codons at the ends of the gene segment to be amplified. This placement of restriction sites at the 5' and 3' ends of the amplified gene sequence allows for gene segments encoding MORT-1-binding protein or a fragment thereof to be custom designed for ligation other sequences and/or cloning sites in vectors.

PCR and other methods of amplification of RNA and/or DNA are well known in the art and can be used according to the present invention without undue experimentation, based on the teaching and guidance presented herein. Known methods of DNA or RNA amplification include, but are not limited to polymerase chain reaction (PCR) and related amplification processes (see, e.g., U.S. Pat. Nos. 4,683,195, 4,683,202, 4,800,159, 4,965,188, to Mullis et al; 4,795,699 and 4,921, 794 to Tabor et al; 5,142,033 to Innis; 5,122,464 to Wilson et al; 5,091,310 to Innis; 5,066,584 to Gyllensten et al; 4,889, 818 to Gelfand et al; 4,994,370 to Silver et al; 4,766,067 to Biswas; 4,656,134 to Ringold; and Innis et al, 1990) and RNA mediated amplification which uses anti-sense RNA to the target sequence as a template for double stranded DNA synthesis (U.S. Pat. No. 5,130,238 to Malek et al, with the tradename NASBA); and immuno-PCR which combines the use of DNA amplification with antibody labeling. (Ruzicka et al, 1993; Sano et al, 1992; Sano et al, 1991), the entire contents of which patents and reference are entirely incorporated herein by reference.

In an analogous fashion, biologically active fragments of MORT-1-binding proteins (e.g., those of any of the MACH isoforms) may be prepared as noted above with respect to the analogs of MORT-1-binding proteins. Suitable fragments of MORT-1-binding proteins are those which retain the MORT-1 binding capability and which can mediate the biological activity of FAS-R and p55-R as noted above. Accordingly, MORT-1-binding protein fragments can be prepared which have a dominant-negative or a dominant-positive effect as noted above with respect to the analogs. It should be noted that these fragments represent a special class of the analogs of the invention, namely, they are defined portions of MORT-1-binding proteins derived from the full MORT-1-binding protein sequence (e.g., from that of any one of the MACH isoforms), each such portion or fragment having any of the above-noted desired activities. Such fragment may be, e.g., a peptide.

Similarly, derivatives may be prepared by standard modifications of the side groups of one or more amino acid residues of the MORT-1-binding protein, its analogs or fragments, or by conjugation of the MORT-1-binding protein, its analogs or fragments, to another molecule, e.g., an antibody, enzyme, receptor, etc., as are well known in the art. Accordingly, "derivatives" as used herein covers derivatives which may be prepared from the functional groups which occur as side chains on the residues or the N- or C-terminal groups, by means known in the art, and are included in the invention. Derivatives may have chemical moieties such as carbohydrate or phosphate residues, provided such a fraction has the same or higher biological activity as MORT-1-binding proteins.

For example, derivatives may include aliphatic esters of the carboxyl groups, amides of the carboxyl groups by reaction with ammonia or with primary or secondary amines, N-acyl derivatives or free amino groups of the amino acid residues formed with acyl moieties (e.g., alkanoyl or carbocyclic aroyl groups) or O-acyl derivatives of free hydroxyl group (for example that of seryl or threonyl residues) formed with acyl moieties.

The term "derivatives" is intended to include only those derivatives that do not change one amino acid to another of the twenty commonly occurring natural amino acids.

Although MORT-1-binding protein is a protein or polypeptide, it is a sequence of amino acid residues. A polypeptide consisting of a larger sequence which includes the entire sequence of a MORT-1-binding protein, in accordance with the definitions herein, is intended to be included within the scope of such a polypeptide as long as the additions do not affect the basic and novel characteristics of the invention, i.e., if they either retain or increase the biological activity of MORT-1-binding protein or can be cleaved to leave a protein or polypeptide having the biological activity of MORT-1- binding protein. Thus, for example, the present invention is intended to include fusion proteins of MORT-1-binding protein with other amino acids or peptides.

The new MORT-1-binding protein, their analogs, fragments and derivatives thereof, have a number of uses, for example:

(i) MORT-1-binding protein, its analogs, fragments and derivatives thereof, may be used to mimic or enhance the function of MORT-1 and hence the FAS-R ligand or TNF, in situations where an enhanced FAS-R ligand or TNF effect is desired, such as in anti-tumor, anti-inflammatory, anti-HIV applications, etc., where the FAS-R ligand- or TNF-induced cytotoxicity is desired. In this case the MORT-1-binding protein, its analogs, fragments or derivatives thereof, which enhance the FAS-R ligand of TNF effect, i.e., cytotoxic effect, may be introduced to the cells by standard procedures known per se. For example, as the MORT-1-binding protein are intracellular and should be introduced only into the cells where the FAS-R ligand or TNF effect is desired, a system for specific introduction of this protein into the cells is necessary. One way of doing this is by creating a recombinant animal virus, e.g., one derived from Vaccinia, to the DNA of which the following two genes will be introduced: the gene encoding a ligand that binds to cell surface proteins specifically expressed by the cells, e.g., ones such as the AIDs (HIV) virus gp120 protein which binds specifically to some cells (CD4 lymphocytes and related leukemias) or any other ligand that binds specifically to cells carrying a FAS-R or p55-R, such that the recombinant virus vector will be capable of binding such FAS-R- or p55-R-carrying cells; and the gene encoding the MORT-1-binding protein. Thus, expression of the cell-surface-binding protein on the surface of the virus will target the virus specifically to the tumor cell or other FAS-R- or p55-R-carrying cell, following which the MORT-1-binding protein encoding sequence will be introduced into the cells via the virus, and once expressed in the cells, will result in enhancement of the FAS-R ligand or TNF effect leading to the death of the tumor cells or other FAS-R- or p55-R-carrying cells it is desired to kill. Construction of such recombinant animal virus is by standard procedures (see for example, Sambrook et al, 1989). Another possibility is to introduce the sequences of the MORT-1-binding protein (e.g., any one of the MACH isoforms) in the form of oligonucleotides which can be absorbed by the cells and expressed therein.

(ii) They may be used to inhibit the FAS-R ligand or TNF effect, e.g., in cases such as tissue damage in septic shock, graft-vs.-host rejection, or acute hepatitis, in which it is desired to block the FAS-R ligand or TNF induced FAS-R or p55-R intracellular signaling. In this situation, it is possible, for example, to introduce into the cells, by standard procedures, oligonucleotides having the anti-sense coding sequence for the MORT-1-binding protein, which would effectively block the translation of mRNAs encoding either the MORT-1 protein or the MORT-1-binding protein and thereby block its expression and lead to the inhibition of the FAS-R ligand- or TNF-effect. Such oligonucleotides may be introduced into the cells using the above recombinant virus approach, the second sequence carried by the virus being the oligonucleotide sequence.

Another possibility is to use antibodies specific for the MORT-1-binding protein to inhibit its intracellular signaling activity.

Yet another way of inhibiting the FAS-R ligand or TNF effect is by the recently developed ribozyme approach. Ribozymes are catalytic RNA molecules that specifically cleave RNAs. Ribozymes may be engineered to cleave target RNAs of choice, e.g., the mRNAs encoding the MORT-1-binding protein of the invention. Such ribozymes would have a sequence specific for the MORT-1-binding protein mRNA and would be capable of interacting therewith (complementary binding) followed by cleavage of the mRNA, resulting in a decrease (or complete loss) in the expression of the MORT-1-binding protein, the level of decreased expression being dependent upon the level of ribozyme expression in the target cell. To introduce ribozymes into the cells of choice (e.g., those carrying FAS-R or p55-R), any suitable vector may be used, e.g., plasmid, animal virus (retrovirus) vectors, that are usually used for this purpose (see also (i) above, where the virus has, as second sequence, a cDNA encoding the ribozyme sequence of choice). (For reviews, methods etc. concerning ribozymes see Chen et al, 1992; Zhao and Pick, 1993; Shore et al, 1993; Joseph and Burke, 1993; Shimayama et al, 1993; Cantor et al, 1993; Barinaga, 1993; Crisell et al, 1993 and Koizumi et al, 1993).

(iii) The MORT-1-binding protein, its analogs, fragments or derivatives may also be used to isolate, identify and clone other proteins of the same class, i.e., those binding to FAS-R intracellular domain or to functionally related receptors, or those binding to MORT-1 and thereby to functionally related receptors such as FAS-R and p55-R, and involved in the intracellular signaling process. In this application the above noted yeast two-hybrid system may be used, or there may be used a recently developed system employing non-stringent Southern hybridization followed by PCR cloning (Wilks et al, 1989). In the Wilks et al publication, there is described the identification and cloning of two putative protein-tyrosine kinases by application of non-stringent southern hybridization followed by cloning by PCR based on the known sequence of the kinase motif, a conceived kinase sequence. This approach may be used, in accordance with the present invention using the sequence of the MORT-1-binding Protein (e.g., any of the MACH isoforms) to identify and clone those of related MORT-1-binding proteins.

(iv) Yet another approach to utilizing the MORT-1-binding protein, or its analogs, fragments or derivatives thereof, of the invention is to use them in methods of affinity chromatography to isolate and identify other proteins or factors to which they are capable of binding, e.g., MORT-1, or other proteins or factors involved in the intracellular signaling process. In this application, the MORT-1-binding protein, its analogs, fragments or derivatives thereof, of the present invention, may be individually attached to affinity chromatography matrices and then brought into contact with cell extracts or isolated proteins or factors suspected of being involved in the intracellular signaling process. Following the affinity chromatography procedure, the other proteins or factors which bind to the MORT-1-binding protein, or its analogs, fragments or derivatives thereof of the invention, can be eluted, isolated and characterized.

(v) As noted above, the MORT-1-binding protein, or its analogs, fragments or derivatives thereof, of the invention may also be used as immunogens (antigens) to produce specific antibodies thereto. These antibodies may also be used for the purposes of purification of the MORT-1-binding protein (e.g., MACH isoforms) either from cell extracts or from transformed cell lines producing MORT-1-binding protein, or its analogs or fragments. Further, these antibodies may be used for diagnostic purposes for identifying disorders related to abnormal functioning of the FAS-R ligand or TNF system, e.g., overactive or underactive FAS-R ligand- or TNF-induced cellular effects. Thus, should such disorders be related to a malfunctioning intracellular signaling system involving the MORT-1 protein, or MORT-1-binding protein, such antibodies would serve as an important diagnostic tool.

It should also be noted that the isolation, identification and characterization of the MORT-1-binding protein (e.g., the MACH isoforms) of the invention may be performed using any of the well known standard screening procedures. For example, one of these screening procedures, the yeast two-hybrid procedure as is set forth herein (example 1), was used to identify the MORT-1 protein and subsequently the MORT-1-binding proteins (Examples 2-3) of the invention. Likewise as noted above and below, other procedures may be employed such as affinity chromatography, DNA hybridization procedures, etc. as are well known in the art, to isolate, identify and characterize MORT-1-binding protein of the invention or to isolate, identify and characterize additional proteins, factors, receptors, etc. which are capable of binding to the MORT-1 protein or to the MORT-1-binding proteins of the invention.

As set forth hereinabove, the MORT-1-binding protein may be used to generate antibodies specific to MORT-1-binding proteins, e.g., MACH isoforms. These antibodies or fragments thereof may be used as set forth hereinbelow in detail, it being understood that in these applications the antibodies or fragments thereof are those specific for MORT-1-binding proteins.

Based on the findings in accordance with the present invention that at least some of the MACH isoforms (see above and Example 3 below) are proteases related to the proteases of the CED3/ICE family of proteases, the following specific medical applications are envisioned for these MACH isoforms: it has been found that specific inhibitors of other CED3/ICE proteases, some of which are cell permeable, already exist, which can block effectively programmed cell death processes. Hence, it is possible in accordance with the present invention to design inhibitors that can prevent FAS-R ligand- or TNF-induced cell death, the pathways in which the MACH protease isoforms are involved. Further, in view of the unique sequence features of these new MACH proteases, it seems possible to design inhibitors that will be highly specific to the TNF- and FAS-R ligand-induced effects. The findings of the present invention also provide a way to study the mechanism in which the "killing protease" is activated in response to FAS-R ligand and TNF, this allowing subsequent development of drugs that can control the extent of this activation. There are many diseases in which such drugs can be of great help. Amongst others, acute hepatitis in which the acute damage to the liver seems to reflect FAS-R ligand-mediated death of the liver cells; autoimmune-induced cell death such as the death of the β Langerhans cells of the pancreas, that results in diabetes; the death of cells in graft rejection (e.g., kidney, heart and liver); the death of oligodendrocytes in the brain in multiple sclerosis; and AIDS-inhibited T cell suicide which causes proliferation of the AIDS virus and hence the AIDS disease.

As mentioned hereinabove and hereinbelow, it appears that two of the MACH isoforms, MACHα2 and MACHα3 may serve as "natural" inhibitors of the MACH protease isoforms, and these may thus be employed as the above noted specific inhibitors of these MACH proteases. Likewise, other substances such as peptides, organic compounds, antibodies, etc. may also be screened to obtain specific drugs which are capable of inhibiting the MACH proteases.

A non-limiting example of how peptide inhibitors of the MACH proteases would be designed and screened is based on previous studies on peptide inhibitors of ICE or ICE-like proteases, the substrate specificity of ICE and strategies for epitope analysis using peptide synthesis. The minimum requirement for efficient cleavage of peptide by ICE was found to involve four amino acids to the left of the cleavage site with a strong preference for aspartic acid in the $P_1$ position and with methylamine being sufficient to the right of the $P_1$ position (Sleath et al, 1990; Howard et al, 1991; Thornberry et al, 1992). Furthermore, the fluorogenic substrate peptide (a tetrapeptide), acetyl-Asp-Glu-Val-Asp-a-(4-methyl-coumaryl-7-amide) abbreviated Ac-DEVD-AMC, corresponds to a sequence in poly (ADP-ribose) polymerase (PARP) found to be cleaved in cells shortly after FAS-R stimulation, as well as other apoptopic processes (Kaufmann, 1989; Kaufmann et al, 1993; Lazebnik et al, 1994), and is cleaved effectively by CPP32 (a member of the CED3/ICE protease family) and MACH proteases.

As Asp in the $P_1$ position of the substrate appears to be important, tetrapeptides having Asp as the fourth amino acid residue and various combinations of amino acids in the first three residue positions can be rapidly screened for binding to the active site of MACH proteases using, for example, the method developed by Geysen (Geysen, 1985; Geysen et al, 1987) where a large number of peptides on solid supports were screened for specific interactions with antibodies. The binding of MACH proteases to specific peptides can be detected by a variety of well known detection methods within the skill of those in the art, such as radiolabeling of the MACH protease, etc. This method of Geysen's was shown to be capable of testing at least 4000 peptides each working day.

Since it may be advantageous to design peptide inhibitors that selectively inhibit MACH proteases without interfering with physiological cell death processes in which other members of the CED3/ICE family of proteases are involved, the pool of peptides binding to MACH proteases in an assay such as the one described above can be further synthesized as a fluorogenic substrate peptide to test for selective cleavage by MACH proteases without being cleaved by other CED3/ICE proteases. Peptides which are determined to be selectively cleaved by the MACH proteases, can then be modified to enhance cell permeability and inhibit the cell death activity of MACH either reversibly or irreversibly. Thornberry et al (1994) reported that a tetrapeptide (acyloxy) methyl ketone Ac-Tyr-Val-Ala-Asp-$CH_2OC(O)$-[2,6-$(CF_3)_2$]Ph was a potent inactivator of ICE. Similarly, Milligan et al (1995) reported that tetrapeptide inhibitors having a chloromethylketone (irreversibly) or aldehyde (reversibly) groups inhibited ICE. In addition, a benzyloxycarboxyl-Asp-$CH_2OC(O)$-2,6-dichlorobenzene (DCB) was shown to inhibit ICE (Mashima et al, 1995). Accordingly, tetrapeptides that selectively bind to MACH proteases can be modified with, for example, an aldehyde group, chloromethylketone, (acyloxy) methyl ketone or a $CH_2OC(O)$-DCB group to create a peptide inhibitor of MACH protease activity.

While some specific inhibitors of other CED3/ICE proteases are cell permeable, the cell permeability of peptide inhibitors may need to be enhanced. For instance, peptides can be chemically modified or derivatized to enhance their permeability across the cell membrane and facilitate the transport of such peptides through the membrane and into the cytoplasm. Muranishi et al (1991) reported derivatizing thyrotropin-releasing hormone with lauric acid to form a lipophilic lauroyl derivative with good penetration characteristics across cell membranes. Zacharia et al (1991) also reported the oxidation of methionine to sulfoxide and the replacement of the peptide bond with its ketomethylene isoester ($COCH_2$) to facilitate transport of peptides through the cell membrane. These are just some of the known modifications and derivatives that are well within the skill of those in the art.

Furthermore, drug or peptide inhibitors, which are capable of inhibiting the cell death activity of MACHα1 and MACHα2, can be conjugated or complexed with molecules that facilitate entry into the cell.

U.S. Pat. No. 5,149,782 discloses conjugating a molecule to be transported across the cell membrane with a membrane blending agent such as fusogenic polypeptides, ion-channel forming polypeptides, other membrane polypeptides, and long chain fatty acids, e.g., myristic acid, palmitic acid. These membranes blending agents insert the molecular conjugates into the lipid bilayer of cellular membranes and facilitate their entry into the cytoplasm.

Low et al, U.S. Pat. No. 5,108,921, reviews available methods for transmembrane delivery of molecules such as, but not limited to, proteins and nucleic acids by the mechanism of receptor mediated endocytotic activity. These receptor systems include those recognizing galactose, mannose, mannose 6-phosphate, transferrin, asialoglycoprotein, transcobalamin (vitamin $B_{12}$), $\alpha$-2 macroglobulins, insulin and other peptide growth factors such as epidermal growth factor (EGF). Low et al teaches that nutrient receptors' such as receptors for biotin and folate, can be advantageously used to enhance transport across the cell membrane due to the location and multiplicity of biotin and folate receptors on the membrane surfaces of most cells and the associated receptor mediated transmembrane transport processes. Thus, a complex formed between a compound to be delivered into the cytoplasm and a ligand, such as biotin or folate, is contacted with a cell membrane bearing biotin or folate receptors to initiate the receptor mediated trans-membrane transport mechanism and thereby permit entry of the desired compound into the cell.

ICE is known to have the ability to tolerate liberal substitutions in the $P_2$ position and this tolerance to liberal substitutions was exploited to develop a potent and highly selective affinity label containing a biotin tag (Thornberry et al, 1994). Consequently, the $P_2$ position as well as possibly the N-terminus of the tetrapeptide inhibitor can be modified or derivatized, such as to with the addition of a biotin molecule, to enhance the permeability of these peptide inhibitors across the cell membrane.

In addition, it is known in the art that fusing a desired peptide sequence with a leader/signal peptide sequence to create a "chimeric peptide" will enable such a "chimeric peptide" to be transported across the cell membrane into the cytoplasm.

As will be appreciated by those of skill in the art of peptides, the peptide inhibitors of MACH proteolytic activity according to the present invention is meant to include peptidomimetic drugs or inhibitors, which can also be rapidly screened for binding to MACH protease to design perhaps more stable inhibitors.

It will also be appreciated that the same means for facilitating or enhancing the transport of peptide inhibitors across cell membranes as discussed above are also applicable to the MACH isoforms themselves as well as other peptides and proteins which exerts their effects intracellularly.

As regards the antibodies mentioned herein throughout, the term "antibody" is meant to include polyclonal antibodies, monoclonal antibodies (mAbs), chimeric antibodies, anti-idiotypic (anti-Id) antibodies to antibodies that can be labeled in soluble or bound form, as well as fragments thereof provided by any known technique, such as, but not limited to enzymatic cleavage, peptide synthesis or recombinant techniques.

Polyclonal antibodies are heterogeneous populations of antibody molecules derived from the sera of animals immunized with an antigen. A monoclonal antibody contains a substantially homogeneous population of antibodies specific to antigens, which population contains substantially similar epitope binding sites. MAbs may be obtained by methods known to those skilled in the art. See, for example Kohler and Milstein (1975); U.S. Pat. No. 4,376,110; Ausubel et al (1988); and Colligan et al (1992-1996), the contents of which references are incorporated entirely herein by reference. Such antibodies may be of any immunoglobulin class including IgG, IgM, IgE, IgA, GILD and any subclass thereof. A hybridoma producing a mAb of the present invention may be cultivated in vitro, in situ or in vivo. Production of high titers of mAbs in vivo or in situ makes this the presently preferred method of production.

Chimeric antibodies are molecules of which different portions are derived from different animal species, such as those having the variable region derived from a murine mAb and a human immunoglobulin constant region. Chimeric antibodies are primarily used to reduce immunogenicity in application and to increase yields in production, for example, where murine mAbs have higher yields from hybridomas but higher immunogenicity in humans, such that human/murine chimeric mAbs are used. Chimeric antibodies and methods for their production are known in the art (Cabilly et al, 1984; Morrison et al, 1984; Boulianne et al, 1984; Cabilly et al, European Patent Application 125023 (published Nov. 14, 1984); Neuberger et al, 1985; Taniguchi et al, European Patent Application 171496 (published Feb. 19, 1985); Morrison et al, European Patent Application 173494 (published Mar. 5, 1986); Neuberger et al, PCT Application WO 86/01533, (published Mar. 13; 1986); Kudo et al, European Patent Application 184187 (published Jun. 11, 1986); Sahagan et al, (1986); Robinson et al, International Patent Application No. WO 87/02671 (published May 7, 1987); Liu et al, 1987; Sun et al, 1987; Better et al, 1988; and Harlow and Lane, supra. These references are entirely incorporated herein by reference.

An anti-idiotypic (anti-Id) antibody is an antibody which recognizes unique determinants generally associated with the antigen-binding site of an antibody. An Id antibody can be prepared by immunizing an animal of the same species and genetic type (e.g., mouse strain) as the source of the mAb to which an anti-Id is being prepared. The immunized animal will recognize and respond to the idiotypic determinants of the immunizing antibody by producing an antibody to these idiotypic determinants (the anti-Id antibody). See, for example, U.S. Pat. No. 4,699,880, which is herein entirely incorporated by reference.

The anti-Id antibody may also be used as an "immunogen" to induce an immune response in yet another animal, producing a so-called anti-anti-Id antibody. The anti-anti-Id may be epitopically identical to the original mAb which induced the anti-Id. Thus, by using antibodies to the idiotypic determinants of a mAb, it is possible to identify other clones expressing antibodies of identical specificity.

Accordingly, mAbs generated against the MORT-1-binding proteins, analogs, fragments or derivatives thereof, of the present invention may be used to induce anti-Id antibodies in suitable animals, such as BALB/c mice. Spleen cells from such immunized mice are used to produce anti-Id hybridomas secreting anti-Id mAbs. Further, the anti-Id mAbs can be coupled to a carrier such as keyhole limpet hemocyanin (KLH) and used to immunize additional BALB/c mice. Sera from these mice will contain anti-anti-Id antibodies that have the binding properties of the original mAb specific for an epitope of the above MORT-1-binding protein, or analogs, fragments and derivatives thereof.

The anti-Id mAbs thus have their own idiotypic epitopes, or "idiotopes" structurally similar to the epitope being evaluated, such as GRB protein-a.

The term "antibody" is also meant to include both intact molecules as well as fragments thereof, such as, for example, Fab and F(ab')2, which are capable of binding antigen. Fab and F(ab')2 fragments lack the Fc fragment of intact antibody, clear more rapidly from the circulation, and may have less non-specific tissue binding than an intact antibody (Wahl et al, 1983).

It will be appreciated that Fab and F(ab')2 and other fragments of the antibodies useful in the present invention may be used for the detection and quantitation of the MORT-1-binding protein according to the methods disclosed herein for intact antibody molecules. Such fragments are typically produced by proteolytic cleavage, using enzymes such as papain (to produce Fab fragments) or pepsin (to produce F(ab')2 fragments).

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics.

An "antigen" is a molecule or a portion of a molecule capable of being bound by an antibody which is additionally capable of inducing an animal to produce antibody capable of binding to an epitope of that antigen. An antigen may have one or more than one epitope. The specific reaction referred to above is meant to indicate that the antigen will react, in a highly selective manner, with its corresponding antibody and not with the multitude of other antibodies which may be evoked by other antigens.

The antibodies, including fragments of antibodies, useful in the present invention may be used to quantitatively or qualitatively detect the MORT-1-binding protein in a sample or to detect presence of cells which express the MORT-1-binding protein of the present invention. This can be accomplished by immunofluorescence techniques employing a fluorescently labeled antibody (see below) coupled with light microscopic, flow cytometric, or fluorometric detection.

The antibodies (or fragments thereof) useful in the present invention may be employed histologically, as in immunofluorescence or immunoelectron microscopy, for in situ detection of the MORT-1-binding protein of the present invention. In situ detection may be accomplished by removing a histological specimen from a patient, and providing the labeled antibody of the present invention to such a specimen. The antibody (or fragment) is preferably provided by applying or by overlaying the labeled antibody (or fragment) to a biological sample. Through the use of such a procedure, it is possible to determine not only the presence of the MORT-1-binding protein, but also its distribution on the examined tissue. Using the present invention, those of ordinary skill will readily perceive that any of wide variety of histological methods (such as staining procedures) can be modified in order to achieve such in situ detection.

Such assays for the MORT-1-binding protein of the present invention typically comprises incubating a biological sample, such as a biological fluid, a tissue extract, freshly harvested cells such as lymphocytes or leukocytes, or cells which have been incubated in tissue culture, in the presence of a detectably labeled antibody capable of identifying the MORT-1-binding protein, and detecting the antibody by any of a number of techniques well known in the art.

The biological sample may be treated with a solid phase support or carrier such as nitrocellulose, or other solid support or carrier which is capable of immobilizing cells, cell particles or soluble proteins. The support or carrier may then be washed with suitable buffers followed by treatment with a detectably labeled antibody in accordance with the present invention, as noted above. The solid phase support or carrier may then be washed with the buffer a second time to remove unbound antibody. The amount of bound label on said solid support or carrier may then be detected by conventional means.

By "solid phase support", "solid phase carrier", "solid support", "solid carrier", "support" or "carrier" is intended any support or carrier capable of binding antigen or antibodies. Well-known supports or carriers, include glass, polystyrene, polypropylene, polyethylene, dextran, nylon amylases, natural and modified celluloses, polyacrylamides, gabbros and magnetite. The nature of the carrier can be either soluble to some extent or insoluble for the purposes of the present invention. The support material may have virtually any possible structural configuration so long as the coupled molecule is capable of binding to an antigen or antibody. Thus, the support or carrier configuration may be spherical, as in a bead, cylindrical, as in the inside surface of a test tube, or the external surface of a rod. Alternatively, the surface may be flat such as a sheet, test strip, etc. Preferred supports or carriers include polystyrene beads. Those skilled in the art will know may other suitable carriers for binding antibody or antigen, or will be able to ascertain the same by use of routine experimentation.

The binding activity of a given lot of antibody, of the invention as noted above, may be determined according to well known methods. Those skilled in the art will be able to determine operative and optimal assay conditions for each determination by employing routine experimentation.

Other such steps as washing, stirring, shaking, filtering and the like may be added to the assays as is customary or necessary for the particular situation.

One of the ways in which an antibody in accordance with the present invention can be detectably labeled is by linking the same to an enzyme and used in an enzyme immunoassay (EIA). This enzyme, in turn, when later exposed to an appropriate substrate, will react with the substrate in such a manner as to produce a chemical moiety which can be detected, for example, by spectrophotometric fluorometric or by visual means. Enzymes which can be used to detectably label the antibody include, but are not limited to, malate dehydrogenase, staphylococcal nuclease, delta-5-steroid isomeras, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may be accomplished using any of a variety of other immunoassays. For example, by radioactive labeling the antibodies or antibody fragments, it is possible to detect R-PTPase through the use of a radioimmunoassay (RIA). A good description of RIA may be found in Work et al, (1978) with particular reference to the chapter entitled "An Introduction to Radioimmune Assay and Related Techniques" by T. Chard, incorporated by reference herein. The radioactive isotope can be detected by such means as the use of a g counter or a scintillation counter or by autoradiography.

It is also possible to label an antibody in accordance with the present invention with a fluorescent compound. When the fluorescently labeled antibody is exposed to light of the proper wavelength, its presence can be then detected due to fluorescence. Among the most commonly used fluorescent labeling compounds are fluorescein isothiocyanate, rhodamine, phycoerythrine, pycocyanin, allophycocyanin, o-phthaldehyde and fluorescamine.

The antibody can also be detectably labeled using fluorescence emitting metals such as $^{152}$E, or others of the lanthanide series. These metals can be attached to the antibody using such metal chelating groups as diethylenetriamine pentaacetic acid (ETPA).

The antibody can also be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

An antibody molecule of the present invention may be adapted for utilization in an immunometric assay, also known as a "two-site" or "sandwich" assay. In a typical immunometric assay, a quantity of unlabeled antibody (or fragment of antibody) is bound to a solid support or carrier and a quantity of detectably labeled soluble antibody is added to permit detection and/or quantitation of the ternary complex formed between solid-phase antibody, antigen, and labeled antibody.

Typical, and preferred, immunometric assays include "forward" assays in which the antibody bound to the solid phase is first contacted with the sample being tested to extract the antigen from the sample by formation of a binary solid phase antibody-antigen complex. After a suitable incubation period, the solid support or carrier is washed to remove the residue of the fluid sample, including unreacted antigen, if any, and then contacted with the solution containing an unknown quantity of labeled antibody (which functions as a "reporter molecule"). After a second incubation period to permit the labeled antibody to complex with the antigen bound to the solid support or carrier through the unlabeled antibody, the solid support or carrier is washed a second time to remove the unreacted labeled antibody.

In another type of "sandwich" assay, which may also be useful with the antigens of the present invention, the so-called "simultaneous" and "reverse" assays are used. A simultaneous assay involves a single incubation step as the antibody bound to the solid support or carrier and labeled antibody are both added to the sample being tested at the same time. After the incubation is completed, the solid support or carrier is washed to remove the residue of fluid sample and uncomplexed labeled antibody. The presence of labeled antibody associated with the solid support or carrier is then determined as it would be in a conventional "forward" sandwich assay.

In the "reverse" assay, stepwise addition first of a solution of labeled antibody to the fluid sample followed by the addition of unlabeled antibody bound to a solid support or carrier after a suitable incubation period is utilized. After a second incubation, the solid phase is washed in conventional fashion to free it of the residue of the sample being tested and the solution of unreacted labeled antibody. The determination of labeled antibody associated with a solid support or carrier is then determined as in the "simultaneous" and "forward" assays.

The MORT-1-binding proteins of the invention may be produced by any standard recombinant DNA procedure (see for example, Sambrook, et al, 1989 and Ausabel et al, 1987-1995, supra) in which suitable eukaryotic or prokaryotic host cells well known in the art are transformed by appropriate eukaryotic or prokaryotic vectors containing the sequences encoding for the proteins. Accordingly, the present invention also concerns such expression vectors and transformed hosts for the production of the proteins of the invention. As mentioned above, these proteins also include their biologically active analogs, fragments and derivatives, and thus the vectors encoding them also include vectors encoding analogs and fragments of these proteins, and the transformed hosts include those producing such analogs and fragments. The derivatives of these proteins, produced by the transformed hosts, are the derivatives produced by standard modification of the proteins or their analogs or fragments.

The present invention also relates to pharmaceutical compositions comprising recombinant animal virus vectors encoding the MORT-1-binding proteins, which vector also encodes a virus surface protein capable of binding specific target cell (e.g., cancer cells) surface proteins to direct the insertion of the MORT-1-binding protein sequences into the cells. Further pharmaceutical compositions of the invention comprises as the active ingredient (a) an oligonucleotide sequence encoding an anti-sense sequence of the MORT-1-binding protein sequence, or (b) drugs that block the proteolytic activity of MACH isoforms.

Pharmaceutical compositions according to the present invention include a sufficient amount of the active ingredient to achieve its intended purpose. In addition, the pharmaceutical compositions may contain suitable pharmaceutically acceptable carriers comprising excipients and auxiliaries which facilitate processing of the active compounds into preparations which can be used pharmaceutically and which can stabilize such preparations for administration to the subject in need thereof as well known to those of skill in the art.

The MORT-1 binding protein MACH, is expressed in different tissues at markedly different levels and apparently also with different patterns of isotypes. These differences probably contribute to the tissue-specific features of response to the Fas/APO1-ligand and TNF. As in the case of other CED3/ICE homologs (Wang et al, 1994; Alnemri et al, 1995), MACH isoforms that contain incomplete CED3/ICE regions (e.g., MACHα3) are found to have an inhibitory effect on the activity of co-expressed MACHα1 or MACHα2 molecules; they are also found to block death induction by Fas/APO1 and p55-R. Expression of such inhibitory isoforms in cells may constitute a mechanism of cellular self-protection against Fas/APO1- and TNF-mediated cytotoxicity. The wide heterogeneity of MACH isoforms, which greatly exceeds that observed for any of the other proteases of the CED3/ICE family should allow a particularly fine tuning of the function of the active MACH isoforms.

It is also possible that some of the MACH isoforms serve other functions. The ability of MACHβ1 to bind to both MORT1 and MACHα1 suggests that this isoform could actually enhance the activity of the enzymatically active isoforms. The mild cytotoxicity observed in 293-EBNA and MCF7 cultures transfected with this isoform and the rather significant cytotoxic effect that it exerts in HeLa cells are likely to reflect activation of endogenously-expressed MACH molecules upon binding to the transfected MACHβ1 molecules. Conceivably, some of the MACH isoforms could also act as docking sites for molecules that are involved in other, non-cytotoxic effects of Fas/APO1 and TNF receptors.

Due to the unique ability of Fas/APO1 and TNF receptors to cause cell death, as well as the ability of the TNF receptors to trigger other tissue-damaging activities, aberrations in the function of these receptors could be particularly deleterious to the organism. Indeed, both excessive and deficient functioning of these receptors have been shown to contribute to pathological manifestations of various diseases (Vassalli, 1992; Nagata and Golstein, 1995). Identifying the molecules that participate in the signaling activity of the receptors, and finding ways to modulate the activity of these molecules, could direct new therapeutic approaches. In view of the suspected central role of MACH in Fas/APO1- and TNF-mediated toxicity, it seems particularly important to design drugs that can block the proteolytic function of MACHα, as was done for some other proteins of the CED3/ICE family (Thornberry et al, 1994; Miller et al, 1995; Mashima et al, 1995; Milligan et al, 1995; Enari et al, 1995; Los et al, 1995). The unique sequence features of the CED3/ICE homolog within MACH molecules could permit the design of drugs that would specifically affect its activity. Such drugs could provide protection from excessive immune-mediated cytotoxicity involving MACHα, without interfering with the physiological cell-death processes in which other members of the CED3/ICE family are involved.

Other aspects of the invention will be apparent from the following examples.

The invention will now be described in more detail in the following non-limiting examples and the accompanying drawings.

It should also be noted that the procedures of: i) two-hybrid screen and two-hybrid β-galactosidase expression test; (ii) induced expression, metabolic labeling and immunoprecipitation of proteins; (iii) in vitro binding; (iv) assessment of the cytotoxicity; and (v) Northern and sequence analyses, as set forth in Examples 1 (see also Boldin et al, 1995b) and 2 below, with respect to MORT-1 and a MORT-1 binding protein, are equally applicable (with some modifications) for the corresponding isolation, cloning and characterization of MACH and its isoforms. These procedures are thus to be construed as the full disclosure of the same procedures used for the isolation, cloning and characterization of MACH in accordance with the present invention, as detailed in Example 3 below.

EXAMPLE 1

Cloning and Isolation of the MORT-1 Protein which Binds to the Intracellular Domain of the FAS-R (i) Two-Hybrid Screen and Two-Hybrid β-Galactosidase Expression Test To isolate proteins interacting with the intracellular domain of the FAS-R, the yeast two-hybrid system was used (Fields and Song, 1989). Briefly, this two-hybrid system is a yeast-based genetic assay to detect specific protein-protein interactions in vivo by restoration of a eukaryotic transcriptional activator such as GAL4 that has two separate domains, a DNA binding and an activation domain, which domains when expressed and bound together to form a restored GAL4 protein, is capable of binding to an upstream activating sequence which in turn activates a promoter that controls the expression of a reporter gene, such as lacZ or HIS3, the expression of which is readily observed in the cultured cells. In this system, the genes for the candidate interacting proteins are cloned into separate expression vectors. In one expression vector, the sequence of the one candidate protein is cloned in phase with the sequence of the GAL4 DNA-binding domain to generate a hybrid protein with the GAL4 DNA-binding-domain, and in the other vector, the sequence of the second candidate protein is cloned in phase with the sequence of the GAL4 activation domain to generate a hybrid protein with the GAL4-activation domain. The two hybrid vectors are then co-transformed into a yeast host strain having a lacZ or HIS3 reporter gene under the control of upstream GAL4 binding sites. Only those transformed host cells (cotransformants) in which the two hybrid proteins are expressed and are capable of interacting with each other, will be capable of expressing the reporter gene. In the case of the lacZ reporter gene, host cells expressing this gene will become blue in color when X-gal is added to the cultures. Hence, blue colonies are indicative of the fact that the two cloned candidate proteins are capable of interacting with each other.

Using this two-hybrid system, the intracellular domain, FAS-IC, was cloned, separately, into the vector pGBT9 (carrying the GAL4 DNA-binding sequence, provided by CLONTECH, USA, see below), to create fusion proteins with the GAL4 DNA-binding domain. For the cloning of FAS-R into pGBT9, a clone encoding the full-length cDNA sequence of FAS-R (WO 95/31544) was used from which the intracellular domain (IC) was excised by standard procedures using various restriction enzymes and then isolated by standard procedures and inserted into the pGBT9 vector, opened in its multiple cloning site region (MCS), with the corresponding suitable restriction enzymes. It should be noted that the FAS-IC extends-from amino acid residues 175-319 of the intact FAS-R, this portion containing residues 175-319 being the FAS-IC inserted into the pGBT9 vector.

The above hybrid (chimeric) vector was then cotransfected together with a cDNA library from human HeLa cells cloned into the pGAD GH vector, bearing the GAL4 activating domain, into the HF7c yeast host strain (all the above-noted vectors, pGBT9 and pGAD GH carrying the HeLa cell cDNA library, and the yeast strain were purchased from Clontech Laboratories, Inc., USA., as a part of MATCHMAKER Two-Hybrid System, #PT1265-1). The co-transfected yeasts were selected for their ability to grow in medium lacking Histidine (His⁻ medium), growing colonies being indicative of positive transformants. The selected yeast clones were then tested for their ability to express the lacZ gene, i.e., for their LACZ activity, and this by adding X-gal to the culture medium, which is catabolized to form a blue colored product by β-galactosidase, the enzyme encoded by the lacZ gene. Thus, blue colonies are indicative of an active lacZ gene. For activity of the lacZ gene, it is necessary that the GAL4 transcription activator be present in an active form in the transformed clones, namely that the GAL4 DNA-binding domain encoded by the above hybrid vector be combined properly with the GAL4 activation domain encoded by the other hybrid vector. Such a combination is only possible if the two proteins fused to each of the GAL4 domains are capable of stably interacting (binding) to each other. Thus, the His⁺ and blue (LACZ⁺) colonies that were isolated are colonies which have been cotransfected with a vector encoding FAS-IC and a vector encoding a protein product of human HeLa cell origin that is capable of binding stably to FAS-IC.

The plasmid DNA from the above His⁺, LACZ⁺ yeast colonies was isolated and electroporated into *E. coli* strain HB101 by standard procedures followed by selection of Leu⁺ and Ampicillin resistant transformants, these transformants being the ones carrying the hybrid pGAD GH vector which has both the Amp$^R$ and Leu2 coding sequences. Such transformants therefore are clones carrying the sequences encoding newly identified proteins capable of binding to the FAS-IC. Plasmid DNA was then isolated from these transformed *E. coli* and retested by:

(a) retransforming them with the original FAS-R intracellular domain hybrid plasmid (hybrid pGTB9 carrying the FAS-IC) into yeast strain HF7 as set forth hereinabove. As controls, vectors carrying irrelevant protein encoding sequences, e.g., pACT-lamin or pGBT9 alone were used for cotransformation with the FAS-IC-binding protein (i.e., MORT-1)-encoding plasmid. The cotransformed yeasts were then tested for growth on His medium alone, or with different levels of 3-aminotriazole; and (b) retransforming the plasmid DNA and original FAS-IC hybrid plasmid and control plasmids described in (a) into yeast host cells of strain SFY526 and determining the LACZ$^+$ activity (effectivity of β-gal formation, i.e., blue color formation).

The results of the above tests revealed that the pattern of growth of colonies in His$^-$ medium was identical to the pattern of LACZ activity, as assessed by the color of the colony, i.e., His$^+$ colonies were also LACZ$^+$. Further, the LACZ activity in liquid culture (preferred culture conditions) was assessed after transfection of the GAL4 DNA-binding and activation-domain hybrids into the SFY526 yeast hosts which have a better LACZ inducibility with the GAL4 transcription activator than that of the HF7 yeast host cells.

Using the above procedure, a protein called previously designated, and now referred to as MORT-1 for "Mediator of Receptor-induced Toxicity", was identified, isolated and characterized.

Furthermore, it should also be mentioned that in a number of the above two-hybrid β-galactosidase expression tests, the expression of β-galactosidase was also assessed by a preferred filter assay. In the screening, five of about 3×10$^6$ cDNAs were found to contain the MORT-1 insert. The so-isolated cloned MORT-1 cDNA inserts were then sequenced using standard DNA sequencing procedures. The amino acid sequence of MORT-1 (SEQ ID NO:2) was deduced from the DNA sequence. Residue numbering in the proteins encoded by the cDNA inserts are as in the Swiss-Prot data bank. Deletion mutants were produced by PCR, and point mutants by oligonucleotide-directed mutagenesis (Ausubel et al, 1994).

(ii) Induced Expression, Metabolic Labeling and Immuno-precipitation of Proteins MORT-1, N-linked to the FLAG octapeptide, (FLAG-MORT-1; Eastman Kodak, New Haven, Conn., USA), Fas-IC, FAS-R, p55-R, a chimera comprised of the extracellular domain of p55-R (amino acids 1-168) fused to the transmembrane and intracellular domain of FAS-R (amino acids 153-319), and the luciferase cDNA which serves as a control, were expressed in HeLa cells. Expression was carried out using a tetracycline-controlled expression vector, in a HeLa cell clone (HtTA-1) that expresses a tetracycline-controlled transactivator (Gossen and Bujard, 1992; see also Boldin et al, 1995). Metabolic labeling with [$^{35}$S]methionine and [$^{35}$S] cysteine (DUPONT, Wilmington, Del., USA and Amersham, Buckinghamshire, England) was performed 18 hours after transfection, by a further 4 h incubation at 37° C. in Dulbecco's modified Eagle's medium lacking methionine and cysteine, but supplemented with 2% dialyzed fetal calf serum. The cells were then lysed in RIPA buffer (10 mM Tris-HCl, pH 7.5, 150 mM NaCl, 1 NP-40, 1% deoxycholate, 0.1% SDS and 1 mM EDTA) and the lysate was precleared by incubation with irrelevant rabbit antiserum (3 μl/ml) and Protein G Sepharose beads (Pharmacia, Uppsala, Sweden; 60 μl/ml). Immunoprecipitation was performed by 1 h incubation at 4° C. of 0.3 ml aliquots of lysate with mouse monoclonal antibodies (5 μl/aliquot) against the FLAG octopeptide (M2; Eastman Kodak), p55-R (#18 and #20; Engelmann et al, 1990), or FAS-R (ZB4; Kamiya Southand Oaks, Calif., USA), or with isotype matched mouse antibodies as a control, followed by a further 1 h incubation with Protein G Sepharose beads (30 μl/aliquot).

(iii) In Vitro Binding

Glutathione S-transferase (GST) fusions with the wild type or a mutated Fas-IC were produced and adsorbed to glutathione-agarose beads; see Boldin et al, 1995; Ausubel et al, 1994; Frangioni and Neel, 1993). Binding of metabolically-labeled FLAG-MORT-1 fusion protein to GST-Fas-IC was assessed by incubating the beads for 2 h at 4° C. with extracts of HeLa cells, metabolically labeled with [$^{35}$S]methionine (60 μCi/ml), that express FLAG-MORT-1. The extracts were prepared in a buffer containing 50 mM Tris-HCl, pH 7.5, 150 mM NaCl, 0.1% NP-40; 1 mM dithioteitol, 1 mM EDTA, 1 mM phenylmethylsulfonyl fluoride, 20 μg/ml Aprotonin, 20 g/ml Leupeptin, 10 mM-sodium fluoride and 0.1 mM sodium vanadate (1 ml per 5.times.10$^5$ cells).

(iv) Assessment of the Cytotoxicity Triggered by Induced Expression of MORT-1

MORT-1, Fas-IC, p55-IC and luciferase cDNAs were inserted into a tetracycline-controlled expression vector and transfected to HtTA-1 cells (a HeLa cell line) (Gossen and Bujard, 1992) together with the secreted placental alkaline phosphatase cDNA, placed under control of SV40 promoter (the pSBC-2 vector, Dirks et al, 1993). Cell death was assessed 40 hours after transfection, either by the neutral-red uptake assay (Wallach, 1984) or, for assessing specifically the death in those cells that express the transfected cDNAs, by determining the amounts of placental alkaline phosphatase (Berger et al, 1988) secreted to the growth medium at the last 5 hours of incubation.

In another set of experiments to analyze the region of the MORT-1 protein involved in the binding to the FAS-IC, the following proteins were expressed transiently in HeLa cells that contain a tetracycline-controlled transactivator (HtTA-1), using a tetracycline-controlled expression vector (pUHD10-3): Human FAS-R alone; Human FAS-R as well as the N-terminal part of MORT-1 (amino acids 1-117, the "MORT-1 head"); Human FAS-R as well as the C-terminal part of MORT-1, which contains its 'death domain' homology region (amino acids 130-245, the "MORT-1 DD"); FLAG-55.11 (amino acids 309-900 of protein 55.11 fused at the N-terminus to the FLAG octapeptide, the protein 55.11 being a p55-IC-specific binding protein. Twelve hours after transfection, the cells were trypsinized and re-seeded at a concentration of 30,000 cells/well. After 24 hrs further incubation, the cells were treated for 6 hrs with a monoclonal antibody against the extracellular domain of FAS-R (monoclonal antibody CH-11, Oncor, Gaithersburg, Md., USA) at various concentrations (0.001-10 μg/ml monoclonal antibody), in the presence of 10 μg/ml cycloheximide. Cell viability was then determined by the neutral-red uptake assay and the results were presented in terms of % viable cells as compared to cells that had been incubated with cycloheximide alone (in the absence of anti-FAS-R monoclonal antibody CH-11).

(v) Northern and Sequence Analyses

Poly A$^+$ RNA was isolated from total RNA of HeLa cells (Oligotex-dT mRNA kit. QIAGEN, Hilden, Germany). Northern analysis using the MORT-1 cDNA as a probe was performed by conventional methods (see Boldin et al, 1995). The nucleotide sequence of MORT-1 was determined in both directions by the dideoxy chain termination method.

Sequence analysis of the MORT-1 cDNA cloned by the two-hybrid procedure indicated that it encodes a novel protein. Applying the two-hybrid test further to evaluate the specificity of the binding of this protein (MORT-1 for "Mediator of Receptor-induced Toxicity") to Fas-IC, and to define the particular region in Fas-IC to which it binds, led to the following findings (FIG. 1): (a) The MORT-1 protein binds both to human and to mouse Fas-IC, but not to several other tested proteins, including three receptors of the TNF/NGF receptor family (p55 and p75 TNF receptors and CD40); (b) Replacement mutations at position 225 (Ile) in the death domain of FAS-R, shown to abolish signaling both in vitro and in vivo (the lpr$^{eg}$ mutation (Watanabe-Fukunaga et al, 1992; Itoh and Nagata, 1993), also prevents binding of MORT-1 to the FAS-IC; (c) The MORT-1 binding-site in FAS-R occurs within the death domain of this receptor; and (d) MORT-1 binds to itself. This self-binding, and the binding of MORT-1 to FAS-R involve different regions of the protein: A fragment of MORT-1 corresponding to residues 1-117 binds to the full-length MORT-1, but does not bind to itself nor to the FAS-IC. Conversely, a fragment corresponding to residues 130-245 binds to FAS-R, yet does not bind to MORT-1 (FIG. 1). Furthermore, it is apparent from the results in FIG. 1 that the 'death domain' region of FAS-R is critical for FAS-IC self-association, as is the 'death domain' region of p55-R for p55-IC self-association. The deletions on both sides of these 'death domains' does not affect the self-association ability thereof while, however, a deletion within these 'death domains' does affect the self-association. In the case of MORT-1, the binding of MORT-1 to FAS-IC is also dependent upon the complete (full) 'death domain' of FAS-R, while however, it is also not dependent on the regions outside of the FAS-R 'death domain' region for FAS-IC binding.

In FIG. 1, there is depicted the interaction of the proteins encoded by the Gal4 DNA binding domain and activation-domain constructs (pGBT9 and pGAD-GH) within transfected SFY526 yeasts as assessed by β-galactosidase expression filter assay. The DNA-binding-domain constructs included four constructs of the human Fas-IC, four constructs of the mouse Fas-IC including two full-length constructs having Ile to Leu or Ile to Ala replacement mutations at position 225 (I225N and I225A, respectively), and three MORT-1 constructs, all of which are shown schematically on the left hand side of FIG. 1. The activation-domain constructs included three MORT-1 constructs, the MORT-1 portion being as in the DNA-binding domain constructs; and a full-length human Fas-IC construct, the Fas-IC portion being the same as in the above DNA-binding domain construct. The intracellular domains of human p55 TNF receptor (p55-IC residues 206-426), human CD40 (CD40-IC, residues 216-277) and human p75 TNF receptor (p75-IC, residues 287-461) as well as lamin, cyclin D and "empty" Gal4 (pGBT9) vectors served as negative controls in the form of DNA-binding domain constructs. SNF-1 and SNF4 served as positive controls in the form of DNA-binding-domain (SNF1) and activation-domain (SNF4) constructs. "Empty" Gal4 vectors (pGAD-GH) also served as negative controls in the form of activation domain constructs. The symbols "++" and "+" denote the development of strong color within 30 and 90 min of the assay, respectively; and "−" denotes no development of color within 24 h. Combinations for which no score is given have not been tested.

Expression of MORT-1 molecules fused at their N terminus with the. FLAG octapeptide (FLAG-MORT-1) yielded in HeLa cells proteins of four distinct sizes—about 97, 28, 32, and 34 kD. The interaction of MORT-1 with Fas-IC in vitro was observed by performing an immunoprecipitate of proteins from extracts of HeLa cells transfected with the FLAG-MORT-1 fusion protein or with luciferase cDNA as a control, the immunoprecipitation being performed with anti-FLAG antibody (αFLAG). The interaction in vitro was also demonstrated between MORT-1 and FAS-IC wherein MORT-1 is in the form of [$^{35}$S] methionine-metabolically labeled FLAG-MORT-1 fusion proteins obtained from extracts of transfected HeLa cells and FAS-IC is in the form of human and mouse GST-FAS-IC fusion proteins including one having a replacement mutation at position 225 in FAS-IC, all of which GST-FAS-IC fusion proteins were produced in E. coli. The GST-fusion proteins were attached to glutathione beads before interaction with the extracts containing the MORT-1-FLAG fusion protein following this interaction, SDS-PAGE was performed. Thus, the in vitro interaction was evaluated by assessing, by autoradiography following SDS-PAGE, the binding of [35] metabolically labeled MORT-1, produced in transfected HeLa cells as a fusion with the FLAG octapeptide (FLAG-MORT-1), to GST, GST fusion with the human or mouse Fas-IC (GST-huFas-IC, GST-mFas-IC) or to GST fusion with Fas-IC containing a Ile to Ala replacement mutation at position 225. It was shown that all four FLAG-MORT-1 proteins showed ability to bind to Fas-IC upon incubation with a GST-Fas-IC fusion protein. As in the yeast two-hybrid test (FIG. 1), MORT-1 did not bind to a GST-Fas-IC fusion protein with a replacement at the lpr$^{eg}$ mutation site (I225A).

The proteins encoded by the FLAG-MORT-1 cDNA showed also an ability to bind to the intracellular domain of FAS-R, as well as to the intracellular domain of FAS-R chimera whose extracellular domain was replaced with that of p55-R (p55-FAS), when co-expressed with these receptors in HeLa cells. In this case, interaction of MORT-1 with FAS-IC in transfected HeLa cells, i.e., in vivo, as observed with immunoprecipitates of various transfected HeLa cells demonstrated the in vivo interaction and specificity of the interaction between MORT-1 and FAS-IC in cells co-transfected with constructs encoding these proteins. Thus, FLAG-MORT-1 fusion protein was expressed and metabolically labeled with [$^{35}$S] cystein (20 µCi/ml) and [$^{35}$S] methionine (40 µCi/ml) in HeLa cells, alone, or together with human FAS-R, FAS-R chimera in which the extracellular domain of FAS-R was replaced with the corresponding region in the human p55-R (p55-FAS), or the human p55-R, as negative control. Cross immunoprecipitation of MORT-1 with the co-expressed receptor was performed using various specific antibodies. The results indicated that, FLAG-MORT-1 is capable of binding to the intracellular domain of FAS-R, as well as to the intracellular domain of a FAS-R-p55-R chimera having the extracellular domain of p55-R and the intracellular domain of FAS-R, when co-expressed with these receptors in the HeLa cells. Further, immunoprecipitation of FLAG-MORT-1 from extracts of the transfected cells also resulted in precipitation of the co-expressed FAS-R or the co-expressed p55-FAS chimera. Conversely, immunoprecipitation of these receptors resulted in the coprecipitation of the FLAG-MORT-1.

Northern analysis using the MORT-1 cDNA as probe revealed a single hybridizing transcript in HeLa cells. In a Northern blot in which poly A$^+$ RNA (0.3 µg) from transfected cells was hybridized with MORT-1 cDNA, the size of the RNA transcript (about 1.8 kb) was found to be close to the size of the MORT-1 cDNA (about 1702 nucleotides).

In sequence analysis, the cDNA was found to contain an open reading frame of about 250 amino acids. FIG. 2 depicts the preliminary nucleotide (SEQ ID NO:1) and deduced amino acid sequence (SEQ ID NO:2) of MORT-1 in which the 'death domain' motif is underlined, as is a possible start Met residue (position 49; bold, underlined M) and the translation stop codon (the asterisk under the codon at position 769-771). This 'death domain' motif shares homology with the known p55-R and FAS-R 'death domain' motifs (p55DD and FAS-DD). In order to determine the precise C-terminal end of MORT-1 and to obtain evidence concerning the precise N-terminal (initial Met residue) end of MORT-1, additional experiments were carried out as follows:

Using the methods described above, a number of constructs encoding MORT-1 molecules fused at their N-terminus with the FLAG octapeptide (FLAG-MORT-1) were constructed and expressed in HeLa cells with metabolic labeling of the expressed proteins using $^{35}$S-cysteine and $^{35}$S-methionine. The MORT-1-FLAG molecules were encoded by the following cDNAs containing different portions of the MORT-1-encoding sequence:

i) The FLAG octapeptide cDNA linked to the 5' end of the MORT-1 cDNA from which nucleotides 1-145 of SEQ ID NO:1 (see FIG. 2) have been deleted;

ii) The FLAG octapeptide cDNA linked to the 5' end of the MORT-1 full length cDNA;

iii) The FLAG octapeptide cDNA linked to the 5' end of the MORT-1 cDNA from which nucleotides 1-145 as well as nucleotides 832-1701 of SEQ ID NO:1 (FIG. 2) have been deleted and the codon GCC at position 142-144 was mutated to TCC to prevent start of translation at this site.

Following expression of the above FLAG-MORT-1 fusion products, immunoprecipitation was carried out as mentioned above, using either anti-FLAG monoclonal antibodies (M2) or as a control, anti-p75 TNF-R antibodies (#9), followed by SDS-PAGE (10% acrylamide) and autoradiography. The results of the analysis with the above FLAG-MORT-1 fusion products confirmed (validated) the C-terminal end of MORT-1 and have provided evidence that the N-terminal end of MORT-1 may be at position 49 of the sequence in FIG. 2.

Indeed, it has been shown by additional expression experiments of MORT-1 without the FLAG octapeptide fused to its 5'-end, that Met$^{49}$ serves as an effective site of translation initiation.

A search conducted in the 'Gene Bank' and 'Protein Bank' DataBases revealed that there is no sequence corresponding to that of the above isolated MORT-1 sequence. Thus, MORT-1 represents a new FAS-IC-specific binding protein.

High expression of p55-IC results in triggering of a cytocidal effect (Boldin et al, 1995). The expression of Fas-IC in HeLa cells also has such an effect, though to a lower extent, which could be detected only with the use of a sensitive assay. The ligand independent triggering of cytocidal effects in cells transfected with MORT-1, as well as human p55-IC and FAS-IC, was thus analyzed. The effect of transient expression of MORT-1, human Fas-IC, human p55-IC, or luciferase that served as a control, on the viability of HeLa cells was assessed using a tetracycline-controlled expression vector. Cell viability was evaluated 40 min after transfecting these cDNAs either in the presence or absence of tetracycline (1 µg/ml, to block expression), together with a cDNA encoding the secreted placental alkaline phosphatase. Cell viability was determined either by the neutral red uptake assay or, for determining specifically the viability of those particular cells that express the transfected DNA, by measuring the amounts of placental alkaline phosphatase secreted to the growth medium.

The above analysis revealed that the expression of MORT-1 in HeLa cells resulted in significant cell death, greater than that caused by FAS-IC expression. These cytotoxic effects of all of p55-IC, FAS-IC and MORT-1 seem to be related to the 'death domain' regions, present in all of these proteins, which 'death domains' have a propensity to self-associate, and thereby possibly prompting the cytotoxic effects.

In view of the above mentioned characteristics of MORT-1, namely, the specific association of MORT-1 with that particular region in FAS-R which is involved in cell death induction, and the fact that even a slight change of structure in that region, which prevents signaling (the lpr$^{cg}$ mutation) abolishes also the binding of MORT-1, indicates that this protein plays a role in the signaling or triggering of cell death. This notion is further supported by the observed ability of MORT-1 to trigger by itself a cytocidal effect. Thus, MORT-1 may function as (i) a modulator of the self-association of FAS-R by its own ability to bind to FAS-R as well as to itself, or (ii) serve as a docking site for additional proteins that are involved in the FAS-R signaling, i.e., MORT-1 may be a 'docking' protein and may therefore bind other receptors besides FAS-R, or (iii) constitutes part of a distinct signaling system that interacts with FAS-R signaling.

In order to further analyze the regions of MORT-1 involved in FAS-IC binding and modulation of the FAS-R-mediated cellular effects (cytotoxicity), the above-mentioned experiments were carried out, using vectors encoding portions of MORT-1 (the 'MORT-1 head', amino acids 1-117 and the 'MORT-1 dd', amino acids 130-245) (separately), with a vector encoding the human FAS-R for co-transfections of HeLa cells. In these experiments, the various proteins and combinations of proteins were expressed transiently in HeLa cells that contain a tetracycline-controlled transactivator (HtTA-1) by inserting the sequences encoding the proteins into a tetracycline-controlled expression vector pUHD10-3. Control transfections employed vectors encoding only the FAS-R and vectors encoding the FLAG-55.11 fusion protein (the 55.11 protein being a p55-IC-specific binding protein of which a portion containing amino acids 309-900 was fused (at its N-terminal) to the FLAG octapeptide).

Following the transfection and incubation periods, the transfected cells were treated with various concentrations of an anti-FAS-R monoclonal antibody (CH-11) which binds specifically to the extracellular domain of FAS-R expressed by cells. This binding of anti-FAS-R antibody induces the aggregation of the FAS-R at the cell surface (much like the FAS-R ligand) and induces the intracellular signaling pathway mediated by the FAS-IC, resulting, ultimately, in cell death (FAS-R mediated cell cytotoxicity). The concentrations of the anti-FAS-R monoclonal antibody (CH-11) used were in the range of 0.01-10 µg/ml, usually concentrations such as 0.005; 0.05; 0.5 and 5 µg/ml. The cells were treated with the anti-FAS antibody in the presence of 10 µg/ml cycloheximide.

The results of the above analysis show that the expression of FAS-R in the transfected cells conveys an increased sensitivity to the cytocidal effects of the anti-FAS-R antibodies (compare "fas" to "55.11"). Further, the co-expression of the region in MORT-1 that contains the 'death domain' homology region and FAS-R ("fas+MORT-1 dd) strongly interferes with FAS-induced (i.e., FAS-R mediated) cell death as would be expected from the ability of the MORT-1 'death domain' (DD) region to bind to the FAS-R 'death domain' (FAS-DD). Moreover, co-expression of the N-terminal part of MORT-1 and FAS-R ("fas+MORT1 he") does not interfere with FAS-R-mediated cell death and, if at all, somewhat enhances the cytotoxicity (i.e., slightly increased cell death).

Thus, the above results clearly indicated that the MORT-1 protein has two distinct regions as far as binding to the FAS-IC and mediation of the cell-cytotoxic activity of the FAS-IC are concerned.

These results therefore also provide a basis for the use of different parts (i.e., active fragments or analogs) of the MORT-1 protein for different pharmaceutical applications. For example, the analogs or fragments or derivatives thereof of the MORT-1 protein which contain essentially only the C-terminal portion of MORT-1 inclusive of its death domain region may be used for inhibiting FAS-R-mediated cytotoxic effects in FAS-R containing cells or tissues and thereby protect these cells or tissues from the deleterious effects of the FAS-R ligand in cases such as, for example, acute hepatitis. Alternatively, the analogs or fragments or derivatives thereof of the MORT-1 protein which contain essentially only the N-terminal portion of MORT-1 may be used for enhancing the FAS-R-mediated cytotoxic effects in FAS-R containing cells and tissues, thereby leading to the enhanced destruction of these cells or tissues when desired in cases such as, for example, tumor cells and autoreactive T and B cells. As detailed herein above, the above uses of the different regions of MORT-1 may be carried out using the various recombinant viruses (e.g., Vaccinia) to insert the MORT-1 region-encoding sequence into specific cells or tissues it is desired to treat.

Furthermore, it is also possible to prepare and use various other molecules such as, antibodies, peptides and organic molecules which have sequences or molecular structures corresponding to the above noted MORT-1 regions in order to achieve the same desired effects mediated by these MORT-1 regions.

Moreover, MORT-1 may be utilized to specifically identify, isolate and characterize other proteins which are capable of binding to MORT-1 (i.e., MORT-1-binding proteins); see Examples 2 and 3.

EXAMPLE 2

Isolation of a MORT-1 Binding Protein (i) Two-Hybrid Screen and Two-Hybrid β-Galactosidase Expression Test In a manner analogous to the procedure described in Example 1, using the intracellular domain of p55 TNF-R (p55 IC) and MORT-1 as baits, and screening a human B-cell library, two cDNA clones were obtained, which encode a protein product capable of binding to both MORT-1 and p55-IC. Both clones have identical nucleotide sequences at the 5' end as shown in FIG. 3 (SEQ ID NO:3).

(ii) Binding Properties of the Newly Cloned cDNA, in Two Hybrid Screens

Using the above-mentioned yeast two-hybrid procedure, a construct containing the new MORT-1-binding protein cDNA was used as a "prey" to which were added constructs of a number of "baits" in separate reactions, to determine the binding specificity of the MORT-1-binding protein encoded by this cDNA. These "baits" included constructs encoding MORT-1, portions of MORT-1 (MORT 'head', aa1-117, MORT 'tail', aa 130-245), the p55 IC (206-426 p55) or portion thereof (the 'death domain', 326-426 p55; and others upstream of the 'death domain' i.e., 206-326). The results are shown in Table 2.

TABLE 2

| Bait | β-galactosidase expression data |
|---|---|
| MORT-1 | +++ |
| 130-245 MORT-1 | + |
| 1-117 MORT-1 | − |
| 206-426 p55 | +++ |
| 326-426 p55 | +++ |
| 206-326 p55 | − |
| 206-308 p55 | − |
| 206-345 p55 | − |
| p55 L351NI | − |
| Fas IC | − |
| 233-319 Fas | − |
| p75 IC | − |
| CD40 IC | − |
| pGBT10 | − |
| SNF1 | − |
| Cycline D | − |
| Lamin | − |

The above results of the two-hybrid β-galactosidase expression test of the binding of the clone to a large panel of baits confirmed that the protein encoded by this clone binds specifically to the death domains of both the p55 TNF-R and MORT-1.

In general, the MORT-1 binding protein may be utilized directly to modulate or mediate the MORT-1 associated effects on cells, or, indirectly, to modulate or mediate the FAS-R ligand effect on cells when this effect is modulated or mediated by MORT-1. The same holds true with respect to other intracellular proteins or intracellular domains of transmembrane proteins, as specifically demonstrated for the p55 TNF-R herein.

MORT-1-binding proteins include those which bind specifically to the entire MORT-1 protein or those which bind to different regions of the MORT-1 protein, e.g., the above-noted N- and C-terminal regions of MORT-1. The MORT-1-binding proteins which bind specifically to such regions may be used to modulate the activity of these regions and hence the specific activity of MORT-1 as determined by these regions.

EXAMPLE 3

Isolation and Characterization of the MACH Protein, Another MORT-1 Binding Protein (i) Two-Hybrid Screen, Two-Hybrid β-Galactosidase Test, Sequencing and Sequence Analysis Using the procedure set forth in Examples 1 and 2 above, a full length construct encoding human MORT-1 protein was employed as a "bait" in the yeast two-hybrid system to isolate a cDNA clone encoding an additional new MORT-1 binding protein. This new protein was originally designated MORT-2, and now redesignated and referred to as MACH (for MORT-1 associated CED3 homolog), by virtue of its characteristics as detailed herein below.

This cDNA clone was sequenced by standard procedures as set forth in Examples 1 and 2 above. Sequence analysis by standard procedures and computer programs (see Examples 1 and 2) revealed that this cDNA has a novel sequence and encodes a novel protein (neither the DNA nor the amino acid sequences was found in GENBANK or PROTEIN BANK sequence databases). Further, the cDNA encoding MACH was revealed an ORF-B open reading frame which has strong homology to the region above (5' upstream) the 'death domain' motif of the MORT-1 protein (see Example 1). In FIGS. 4A-C, the structure of that part of the MACH cDNA clone which contains ORF-B (235 aa residues; FIG. 4A); the deduced amino acid sequence (SEQ ID NO:5) of the MACH ORF-B (FIG. 4B); and the nucleotide sequence (SEQ ID NO:4) of the MACH cDNA molecule (FIG. 4C) are shown. In FIG. 4A, the hatched region of ORF-B is the region sharing high homology with the region of MORT-1 upstream of the MORT-1 'death domain' motif, and this MACH ORF-B region of homology consisting of the amino acid residues underlined in FIG. 4B.

The yeast two-hybrid test was further applied to evaluate the specificity of binding of MACH to MORT-1, in particular, to define the region in MORT-1 to which MACH binds, as well as to determine which of the MACH ORFs interacts with MORT-1, the procedures being as set forth herein above in Examples 1 and 2. Briefly, various MORT-1 and MACH constructs were prepared for testing the interaction of the proteins encoded by the Gal4 DNA-binding domain and activation domain constructs within transfected SFY526 yeast cells as assessed by the β-galactosidase expression filter assay. The DNA-binding domain constructs were prepared in pGBT9 vectors and the activation domain constructs were prepared in pGAD-GM vectors. For the activation domain constructs, the full-length MACH cDNA was used (MACH), as was a construct encoding only the ORF-B (MACH B) region. Control activation domain constructs were those containing the full-length MORT-1 coding sequence (MORT 1, positive control) and those having no inserts, i.e., "empty" vectors (pGAD-GM). For the DNA-binding domain constructs, the full-length MORT-1 cDNA was used (MORT 1), as were constructs encoding only the MORT-1 upstream region (MORT-1DD aa 130-245). Control DNA-binding domain constructs, which were constructed to determine also the specificity of the MACH binding, included constructs encoding lamin (Lamin), residues 287-461 of the intracellular domain of the human p75 TNF-R (human p75 IC), cyclic D (cycD), SNF1, residues 206-426 of the intracellular domain of the human p55 TNF-R (human p55 IC), the 'death domain' region of the intracellular domain of the human Fas-R (human Fas DD), residues 216-277 of the intracellular domain of the human CD40 (human CD40 IC), vectors without insert or "empty" pGBT9 vectors (pGBT9, negative control), and a construct encoding the ORF-B region of MACH (MACH B). In the assay, the development of color was determined, where the greater the color development, the greater the interaction between the constructs encoded by the DNA-binding domain and activation domain; Color development was depicted by symbols, where "+++" and "+" indicate the development of a strong color within 30 and 90 min. of the assay, respectively, and "---" indicates the lack of development of color within 24 hrs. of the assay. In cases where interactions were not tested, no symbol was indicated. The results of the various interactions for the above case are set forth in Table 3, while the results of the various interactions of the MACH isoforms are depicted in FIG. 5.

TABLE 3

| DNA-Binding Domain Hybrid | DOMAIN HYBRID | | | |
|---|---|---|---|---|
| | MACH | MACH B | MORT 1 | pGAD-GH |
| MORT-1 Binding region in MORT-1 MORT1 (-117) | +++ | +++ | +++ | --- |
| MORT1DD (130-245) Specificity tests | --- | --- | | |
| Lamin | --- | --- | | |
| human p75 IC | --- | | | |
| cyc D | | | | |

TABLE 3-continued

| DNA-Binding Domain Hybrid | DOMAIN HYBRID | | | |
|---|---|---|---|---|
| | MACH | MACH B | MORT 1 | pGAD-GH |
| SNF1 | | | | |
| human p55 IC | | | | |
| human FAS DD | --- | | | |
| human CD40 IC | --- | | | |
| pGBT9 | --- | | | |
| MACH B | | + | + | --- |

Thus, as arises from the results shown in Table 3 above, it is apparent that:

(a) MACH binds to MORT-1 in a very strong and, specific manner;

(b) The MACH binding site in MORT-1 occurs before (upstream of) the 'death domain' motif in MORT-1, i.e., it is in the region of MORT-1 defined by aa 1-117 of MORT-1;

(c) The ORF-B region of MACH is the MORT-1-interacting region of the MACH protein; and (d) The MACH ORF-B region is capable of self-association.

(ii) Cell-Cytotoxic Effects Mediated by the Self-Association Capability of the MACH Protein The observation that MACH can self-associate, in particular, that the ORF-B region of MACH self-associates and the previous correlation between self-association and cell-cytotoxicity as observed for the intracellular domains of p55 TNF-R and FAS-R, and as observed for MORT-1 (see Example 1), suggested that MACH self-association may also be involved in cell-cytotoxicity.

In order to test this possibility, constructs encoding MACH were prepared with a tetracycline-controlled expression vector (for details see Example 1). These constructs were used to transfect HeLa cells in which the vectors were transiently expressed. Besides the MACH constructs, other control constructs were used to evaluate the effect of transient expression on the viability of the HeLa cells to which the effect of the MACH constructs could be compared. These other constructs included MORT-1, human FAS-IC and luciferase (Luc). In addition, co-transfection of the HeLa cells was also tested by using MORT-1 and MACH constructs to determine what effects the interaction between these proteins would cause. After transfection the HeLa cells were incubated and cell viability was evaluated 48 hrs. after transfection either in the presence or the absence of tetracycline (1 µg/ml) to block expression. Cell viability was determined by the neutral red uptake assay.

Figure 6:
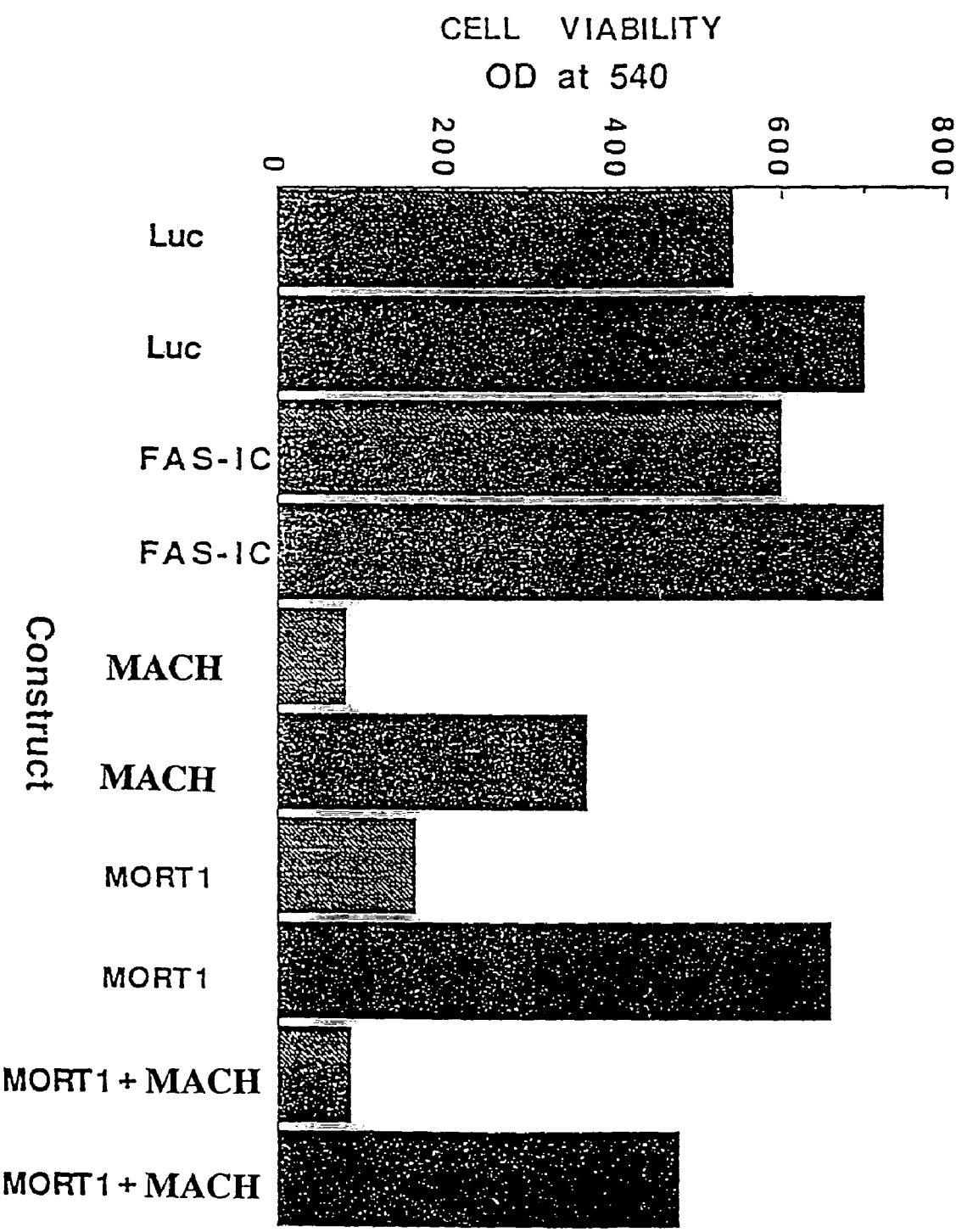
FIG. 6 depicts graphically the ligand-independent triggering of cytocidal effects in HeLa cells transfected with tetracycline-controlled expression vectors encoding MACH, as compared to the effects in these cells transfected with such vectors encoding other proteins such as luciferase (luc, negative control), FAS-IC, MORT-1, and cells co-transfected with vectors encoding MORT-1 and MACH.

The results are shown in FIG. 6, which depicts graphically the ligand-independent triggering of cytocidal effects in cells transfected with MACH in comparison to cells transfected with constructs encoding the other proteins as well as cotransfected cells (MORT1+MACH). The results are shown as the cell viability in OD units at 540 nm for each construct, wherein for each construct a hatched bar indicates incubation of cells following transfection in the absence of tetracycline, and a filled bar indicates incubation of the transfected cells in the presence of tetracycline.

From the results shown in FIG. 6, it is apparent that MACH induces a dramatic cytotoxic effect in HeLa cells, i.e., the induced overexpression of MACH cDNA in HeLa cells, resulting in a dramatic cytotoxic effect. This cytotoxic effect is likely to be related to the self-association capability of MACH.

(iii) Northern Analysis

Using well-known procedures (see Example 1), Northern analysis of several cell lines was carried out using the MACH cDNA as a probe. The results of this analysis show that in a large number of cell lines, in particular, CEM, Raji, Daudi, HeLa, Alexander, Juskat and A673 cell lines, there exist two hybridizing transcripts of approximately 3.2 kb in size.

In view of the above, the MACH protein, particularly the MACHβ1 protein (ORF-B of MACH) may be utilized directly to modulate or mediate the MORT-1 associated effects on cells, or, indirectly, to modulate or mediate the FAS-R ligand effect on cells when this effect is modulated or mediated by MORT-1. The fact that MACH binds specifically to the upstream region of MORT-1 and shares homology with MORT-1 provides for a specific way in which MACH or MACH ORF-B may be used to modulate this specific region of MORT-1 and hence the specific activity of MORT-1 determined by this upstream region. Further, MACH or MACH ORF-B may be used as a modulator or mediator of intracellular effects in an analogous way to MORT-1 itself (see above) by virtue of MACH's ability to self-associate and induce cell-cytotoxicity on its own.

Further analyses of the MACH protein and the DNA sequences encoding it have been performed as set forth herein below. Further, it was revealed that ORF-B of MACH represents but one of a number of MACH isoforms. Hence, the MACH protein and the DNA sequences encoding it have now been renamed, as will become apparent from the following.

(a) Two Hybrid Screen for Proteins that Bind to MORT-1 Reveals a Novel Protein which Shares a Sequence Motif with MORT-1:

As mentioned above, to identify proteins which participate in the induction of cell death by MORT-1, the two-hybrid technique was used to screen cDNA libraries for proteins that bind to MORT-1. A two-hybrid screen of a human B cell library (Durfee et al, 1993) using MORT-1 cDNA as bait yielded cDNA clones of MORT-1 itself, reflecting the ability of this protein to self-associate as well as clones of TRADD, to which MORT-1 binds effectively (see Example 2). The screen also yielded cDNA clones of a novel sequence whose product specifically bound to MORT-1. The protein, which initially was called MACH, and later, after finding that it occurs in multiple isoforms (see below), renamed MACHβ$_1$, showed also an ability to bind in a two hybrid test to itself, yet was unable to bind to FAS-R.

In FIG. 5, there is shown the results of the interaction of MORT-1 and MACH within transfected yeast cells. Briefly, MORT-1 and MACHβ1 and their deletion constructs, as well as MACHα1, a MACHα1 mutant in which the catalytic cysteine Cys$_{360}$ is replaced by Ser (MACHα1 (C360S)) and the intracellular domain of human FAS-R (Fas-IC), were expressed within transfected SFY526 yeast in Gal4 DNA binding domain and activation domain constructs (pGBT9 and pGAD-GH). Their interaction was assessed by a β-galactosidase expression filter assay as described in Boldin et al (1995b). The results are presented in terms of the time required for the development of strong color. ND indicates that the assay was not done. None of the inserts examined interacted with a number of tested negative controls, including the intracellular domains of human p55 TNF receptor, p75 TNF receptor and CD40, and lamin, cyclin D and 'empty' Gal4 vectors. MACHβ1 was cloned by two hybrid screening of a Gal4 AD-tagged human B cell library (Durfee et al, 1993) for proteins that bind to MORT-1, using the HF7c Yeast reporter strain. Except where otherwise indicated, all experimental procedures for the findings presented are as described above (see also Boldin et al, 1995). Deletion analysis showed that MACHβ1 binds to the N-terminal part of MORT-1, which is involved in cell death induction (Chinnaiyan et al 1995). MACHβ1 also self-associated in the transfected yeast. However, it did not bind to several control proteins and unlike MORT-1 was unable to bind to FAS-R (FIG. 5). Expression of MACHβ1 molecules in mammalian cells yielded a 34 kDa protein that bound to MORT-1 molecules co-expressed with it. It was also able to bind to a GST-MORT-1 fusion protein in vitro.

Comparison of the amino acid sequences in MACHβ1 and MORT-1 revealed a shared sequence motif (designated "Mort module") in these two proteins, distinct from the death motif through which MORT-1 binds to FAS-R. This motif occurs once in MORT-1 and twice in MACHβ1. The same motif is found also in PEA-15, an astrocyte phosphoprotein of unknown function. Preliminary data suggest that the MORT motif is involved in the binding of MACHβ1 (and of other MACH isoforms) to MORT-1.

FIG. 7A depicts the deduced amino acid sequence (SEQ ID NO:5) of MACHβ1. The two MORT modules are boxed and the C-termini of the two MACHβ1 deletion mutants employed (FIG. 7) are denoted by asterisks. FIG. 7B shows the sequence homology of the modules in MACHβ1 (designated MACH in FIG. 7B), MORT-1 and the PEA-15 gene (accession number X86809). Identical and similar residues are denoted by boxed and shaded areas, respectively.

Figure 8:
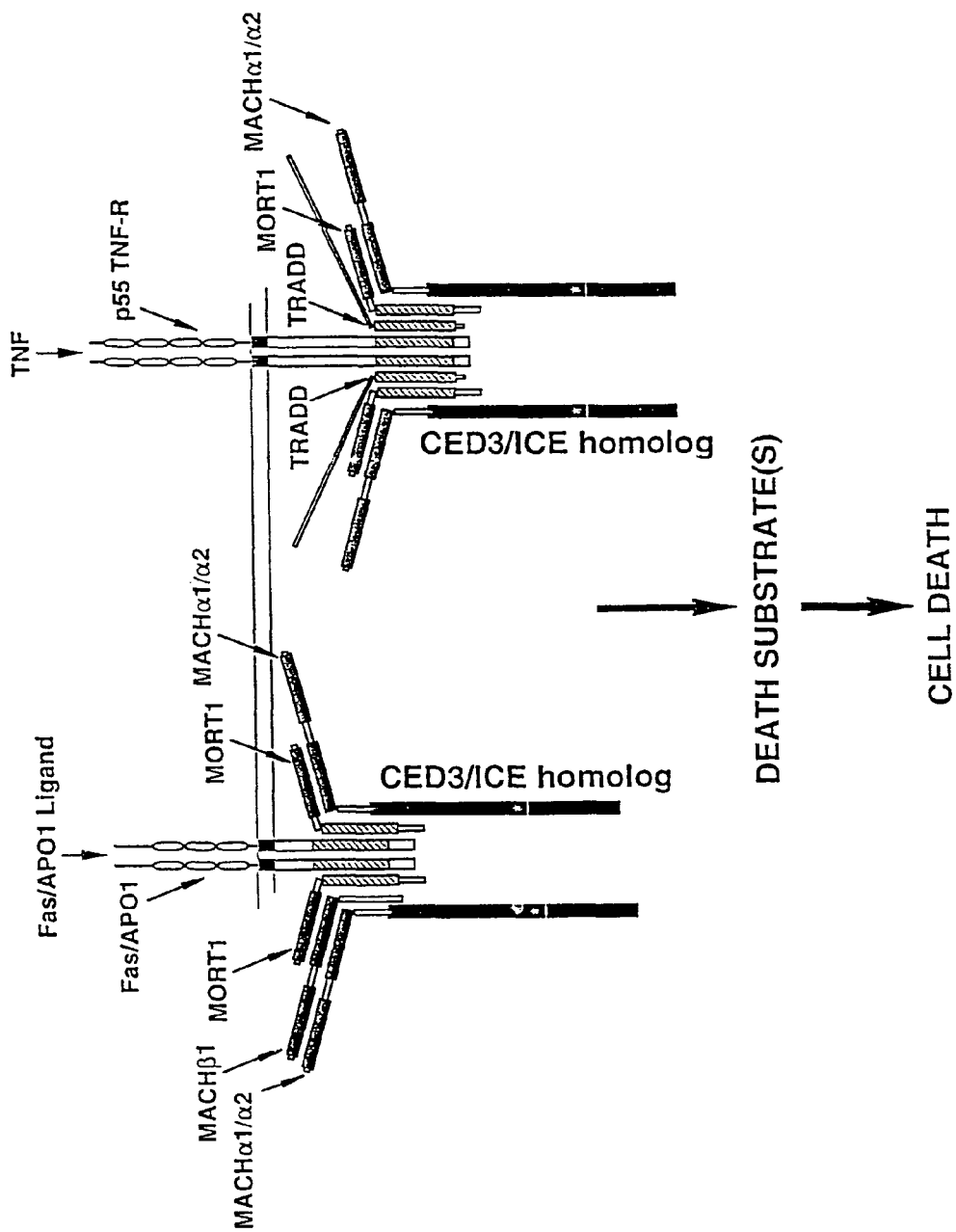
FIG. 8 is a diagrammatic representation of the receptor and target interactions participating in induction of cell-death by Fas/APO1 and p55, the death domain module being indicated by stripes, the MORT module being indicated in gray and the CED3/ICE region being indicated in black.

FIG. 8 shows a diagrammatic representation of the death-domain and MORT modules and of the CED3/ICE homology region in Fas/APO1, MACHβ1 and MACHα1.

Figure 9A:
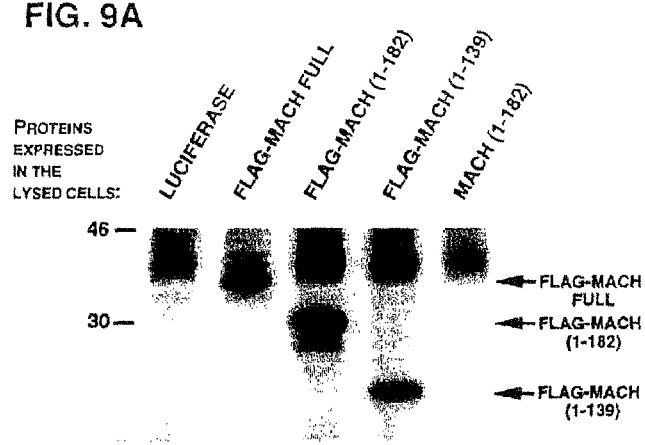
FIGS. 9A-C depict the results illustrating the in vitro interaction of MACHβ1 and its deletion mutants with MORT-1.
Figure 9B:
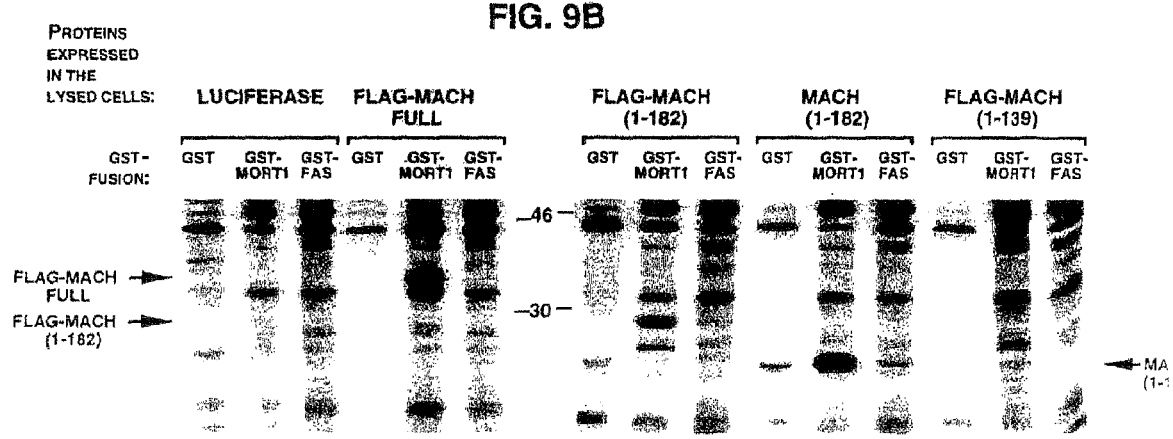
Figure 9C:
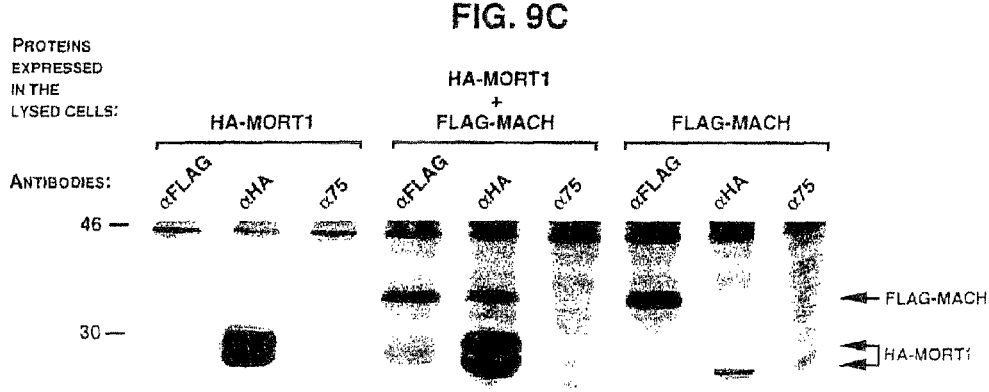

The region in MORT-1 that contains this 'MORT module' has been shown to take part in cell death induction by this protein (see Example 1 above). It has been shown also to contribute to, though not to suffice in, the self association of MORT-1 (see Example 1). As shown in FIG. 5, analysis of the binding properties of deletion constructs of MACHβ1 in transfected yeasts revealed similar involvement of the MORT modules in self-association of MACHβ1, as well as in its binding to MORT-1: Deletion constructs, in which the region below (downstream of) the MORT module was missing, were unable to bind to each other, yet maintained the ability to bind to the full length MORT-1 and to the full length MACHβ1. A further truncation in which part of the MORT module sequence was also deleted, resulted in loss of the binding ability of the proteins. To further assess the involvement of the MORT modules in these interactions, deletion mutants of MACHβ1, fused with the FLAG octapeptide (FLAG-MACHβ1), were expressed in HeLa cells and assessed for their binding in vitro to bacterial-produced glutathione-5-transferase-MORT-1 fusion protein (GST-MORT-1). As shown in FIGS. 9A-C, similarly to the binding observed in the yeast two-hybrid test, this in vitro binding was found to depend on interaction of the region within MACHO1 modules. FIGS. 9A and 9B show the results (autoradiograms) of the in vitro interaction of MACHβ1 and its deletion mutants with MORT-1. Briefly, 35 [S] metabolically labeled MACHβ1, MACHβ1 fused at its N-terminus to the FLAG octapeptide (FLAG-MACHβ1), C-terminus truncation mutants of FLAG-MACHβ1, and, as a control, luciferase, were produced in transfected HeLa cells. Expression was done using a tetracycline-controlled expression vector, in a HeLa cell clone (HtTA-1) that expresses a tetracycline-controlled transactivator.

FIG. 9A shows the assessment of the expression of the proteins and their molecular sizes by immunoprecipitation from cell lysates, using anti-FLAG antibody. The antibodies used are as follows: Rabbit anti-MACHβ1 and anti-MORT1 antisera were raised against GST-MACHβ1 and GST- MORT1 fusion proteins. Mouse monoclonal antibodies against the FLAG octapeptide (M2) and against FAS/APO1 (CH11, Yonehara et al, 1989) were purchased from Eastman Kodak and Oncor (Gaithersburg, Md.) respectively. Mouse monoclonal anti-HA epitope antibody (12CA5, Field et al, 1988) and anti-TNF antibody were produced in our laboratory according to the usual methods well known in the art. FIG. 9B shows affinity binding of the proteins to GST-MORT-1, adsorbed to glutathione-agarose beads (or, as a control, to GST or GST-fused to the intracellular domain of Fas-APO1). FIG. 9C shows the results of the immuno-precipitations of the various MORT-1 and MACH fusion constructs using the various specific antibodies.

(b) MACH Occurs in Multiple Isoforms:

Northern analysis using MACHβ1 cDNA as a probe revealed low abundant transcript(s) of approximately 3 kb in size in several different cell lines. Briefly, Northern blot analysis of total RNA (14 µg/lane) or poly A$^+$ RNA (2 µg) from several cell lines, using MACHβ1 cDNA as probe was performed. The cell lines examined, T47D, CEM, Raji, Daudi, HeLa, Alexander, Jurkat and A673, are all of human origin and were derived from a ductal carcinoma of, the breast, an acute lymphoblastic T cell leukemia, a Burkitt lymphoma, a Burkitt lymphoma, an epithelioid carcinoma, a human hepatoma, an acute T cell leukemia and a rhabdomyosarcoma, respectively. The rather diffuse shape of the hybridizing band on Northern blots suggested that these transcripts are of heterogeneous sizes ranging between 2.85 and 3.5 Kb. Both the amounts and the sizes of the transcripts varied among different human tissues and were not correlated with the expression of MORT1 (Chinnaiyan et al, 1995) or of FAS/APO1 (Watanabe-Fukunaga et al, 1992). cDNA probes were radiolabeled with the random-prime kit (Boehringer Mannheim) and applied for analysis of human multiple tissue blots (Clontech) according to the manufacturer's instructions. In the testis and skeletal muscle, for example, MACH transcripts were barely detectable, even though these tissues express significant amounts of MORT1. Conversely, resting peripheral blood mononuclear leukocytes, in which MORT1 expression is very low, were found to express MACH at high levels. Lectin activation of the leukocytes results in a marked change in the size pattern of MACH transcripts, along with an induction of MORT-1.

Figure 13A:
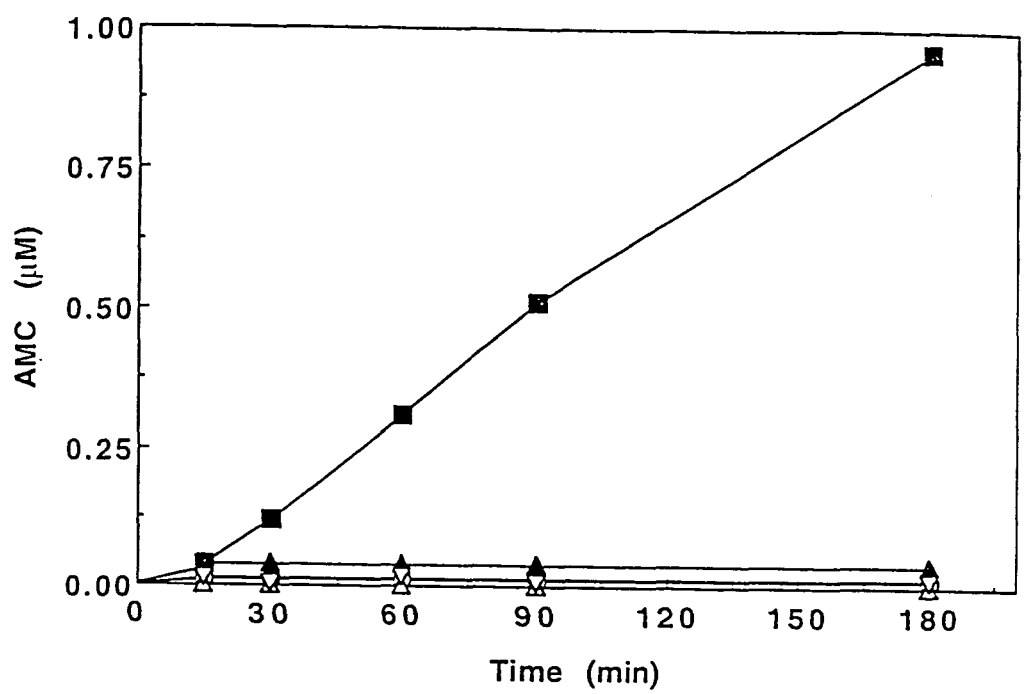
FIGS. 13A and 13B show the protease activity of the CED3/ICE homology region in MACHα.A, Kinetics of cleaage of the PARP-sequence-derived fluorogenic substrate, Ac-DEVD-AMC (50 μM), by extracts of E. coli expressing a GST-fusion protein of the CED3/ICE homology region in MACHα1 ($Ser_{217}$ through the C-terminus of the protein (■) as compared to the lack of cleavage by extracts of bacteria expressing GST-fusion products of the full-length MACHα1 (○), or of the CED3/ICE homology region in which Cys$_{360}$ was replaced by Ser (▽), or by extracts of bacteria expressing GST-fusion products of either of the two potential proteolytic products of the CED3/ICE homology region (Ser$_{217}$ though Asp$_{373}$ (△) and Ser$_{375}$ through Asp$_{479}$, the C-terminus of the protein (▲)).B, Substrate-concentration dependence of the cleavage of Ac-DEVD-AMC. The substrate was incubated for 180 min with extracts of bacteria expressing the GST-fusion product of the MACHα1 CED3/ICE homology region (■). Cleavage of this substrate by the extracts was inhibited in the presence of iodoacetic acid (5 mM, □). Ac-YVAD-AMC, a fluorogenic substrate corresponding to an ICE cleavage site in the IL-1β precursor, was not cleaved (●).

Exploring the nature of this size heterogeneity, cDNA libraries were screened for transcripts that hybridize with the MACHβ1 cDNA probe. MACHα1 and MACHα2 were cloned from a Charon BS cDNA library derived from the mRNA of human thymus. The library was screened under stringent conditions with a MACHβ1 cDNA probe, labeled using a random-priming kit (Boehringer Mannheim). The other MACH isoforms were cloned by RT-PCR, performed on total RNA from Raji (MACHα2, α2, α3, β3, β4 and β5) and Daudi (MACHα2, β2, β3, β4, and β5) human lymphoblastoid cells. Reverse transcriptase reaction was performed with an oligo-dT adapter primer (5'-GACTCGAGTCTA-GAGTCGAC (T)$_{17}$-3'; SEQ ID NO:26) and the SuperScript II reverse transcriptase (GIBCO-BRL), used according to the manufacturer's instructions. The first round of PCR was performed with the Expand Long Template PCR System (Boehringer Mannheim) using the following sense and antisense primers: 5'-AAGTGAGCAGATCAGAATTGAG-3', corresponding to nucleotides 530-551 of the MACHβ1 cDNA (SEQ ID NO:4), and 5'-GACTCGAGTCTAGAGTCGAC-3' (SEQ ID NO:27), respectively. The second round was performed with Vent polymerase (NEB) using the following sense and antisense nested primers:

5' GAGGATCCCCAAATGCAAACTGGATGATGAC-3' (SEQ ID NO:28) and 5'-GCCACCAGCTAAAAACATTCT-CAA-3', (corresponding to nucleotides 962-939 of SEQ ID NO:4) of MACHβ1 cDNA, respectively. To confirm that MACHβ3 and MACHβ4 have initiation codons, a more 5' sequence of these isoforms from the RNA of Raji cells was cloned. The RT-PCR reaction, performed using the oligo-dT adapter primer as described above, was followed by two rounds of PCR (with Vent polymerase (NEB)) using the following sense and antisense oligonucleotides:

5'-TTGGATCCAGATGGACTTCAGCAGAAATCTT-3' (SEQ ID NO:29) and 5'-ATTCTCAAACCCTGCATC-CAAGTG-3' (corresponding to nucleotides 946-923 of SEQ ID NO:4) in MACHβ1. The latter oligonucleotide is specific to the β-isoforms. Among the clones obtained in this way, those found to contain the nucleotides encoding for the amino acids of 'block 2' (whose presence distinguishes MACHβ3 and MACHβ4 from MACHβ1 and MACHβ2 as discussed below) were fully sequenced. Nucleotide sequences in all cloned isoforms were determined in both directions by the dideoxy-chain termination method. Only partial cDNA clones of MACHβ3 and MACHβ2 were obtained. This screening revealed the existence of multiple isoforms of MACH. The amino acid sequences of eight of these isoforms were studied in detail. The results are illustrated diagrammatically in FIG. 12 and exemplified in FIG. 13 where the amino acid sequences of three of the isoforms are compared with known homologs.

Figure 10:
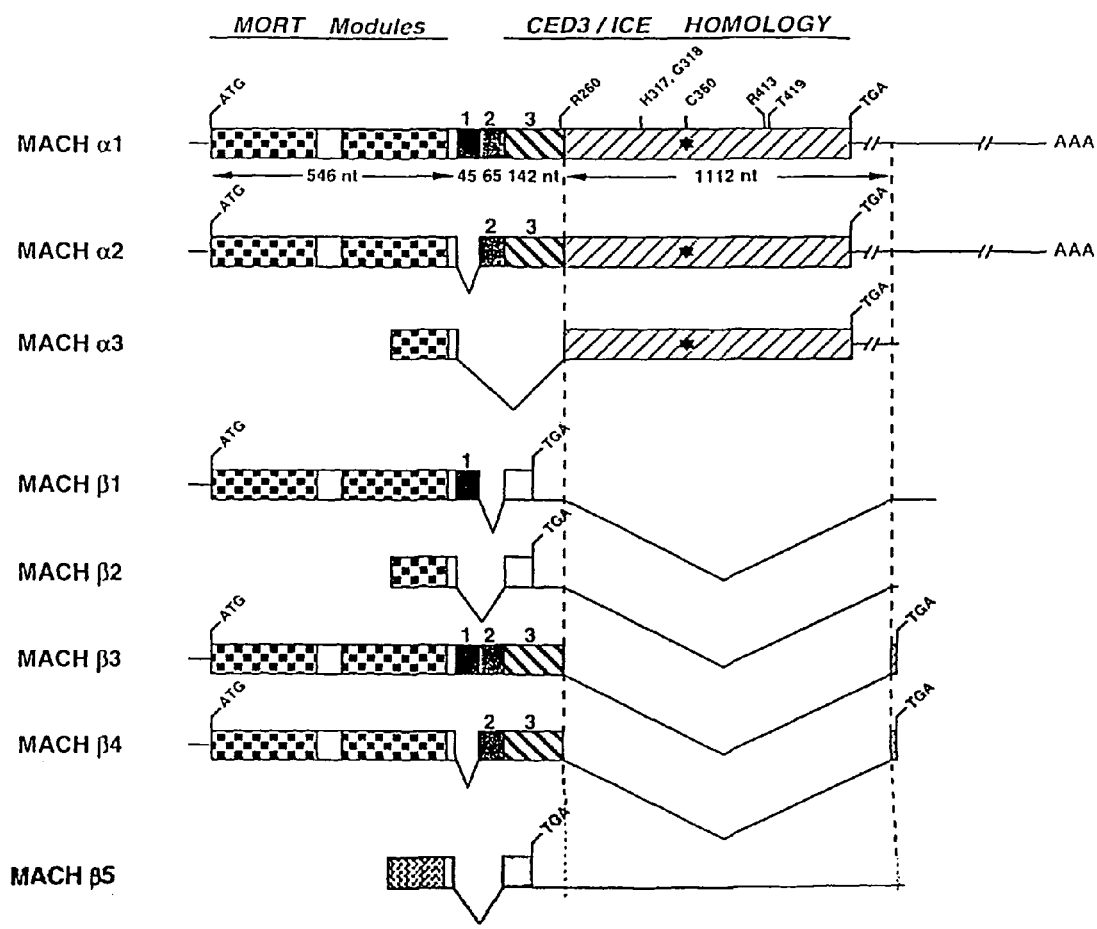
FIG. 10 is a diagrammatic representation of the various MACH isoforms.
Figure 12A:
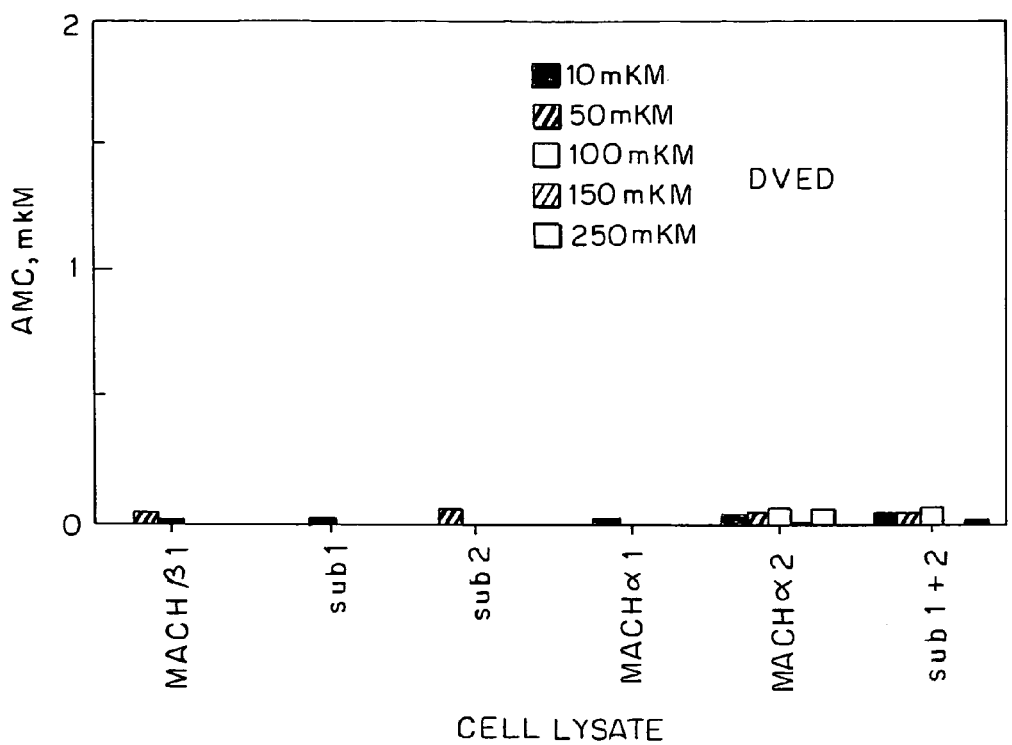
FIGS. 12A-F depict the results illustrating the protease activity of MACHα1 at 15 min.
Figure 12B:
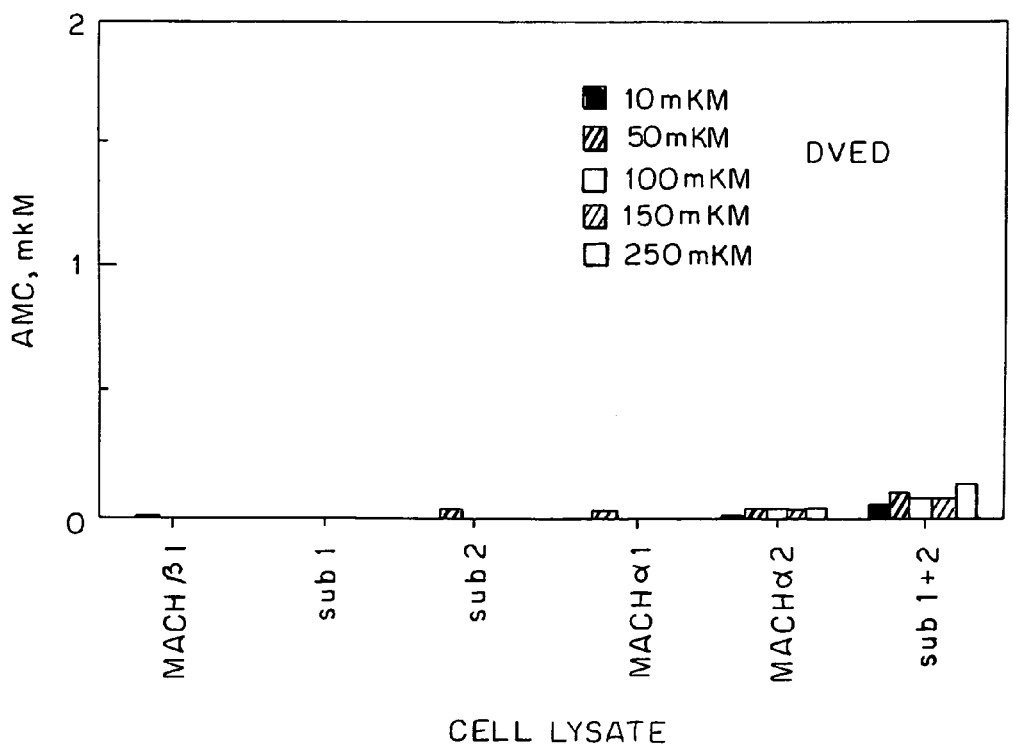
Figure 12C:
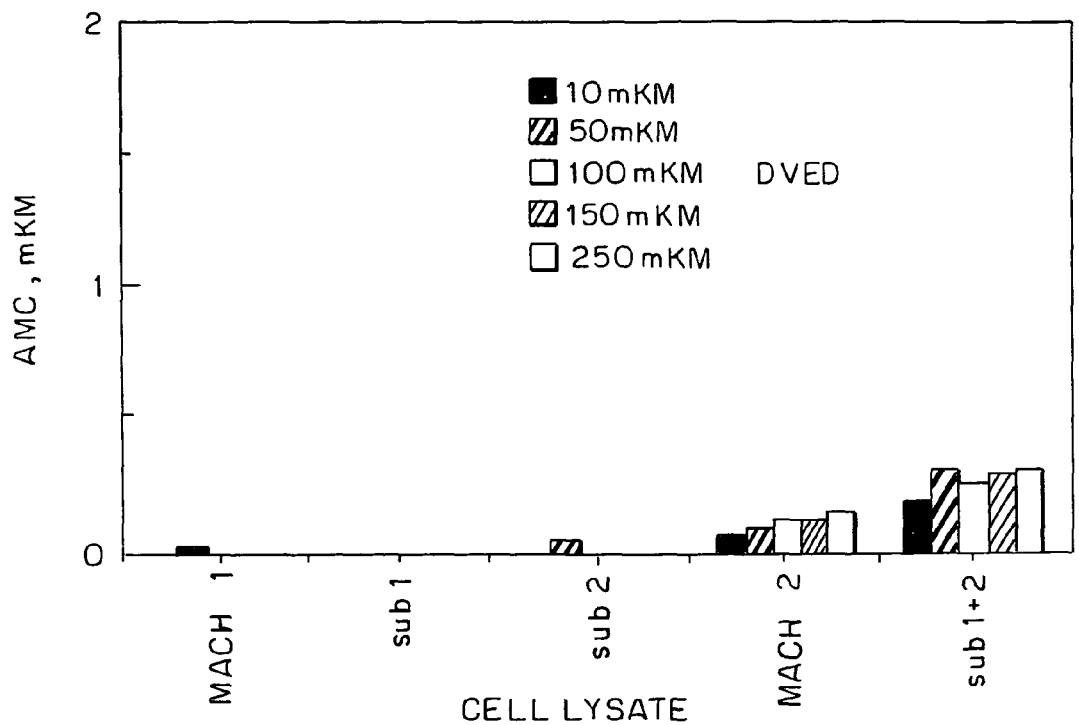
Figure 12D:
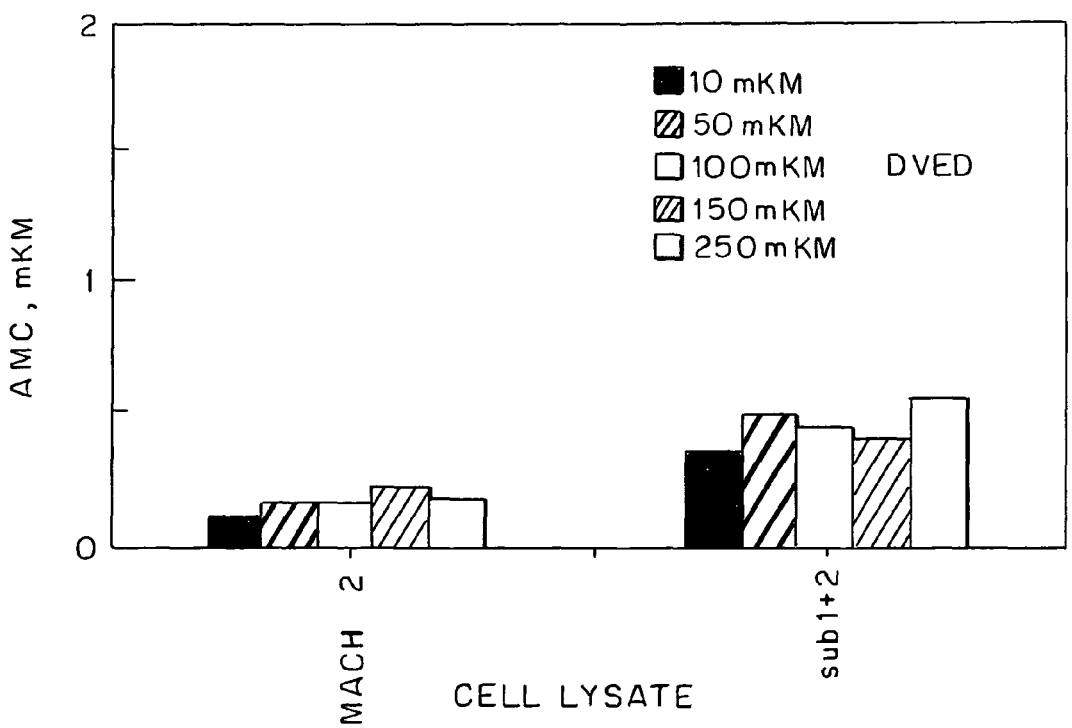
Figure 12E:
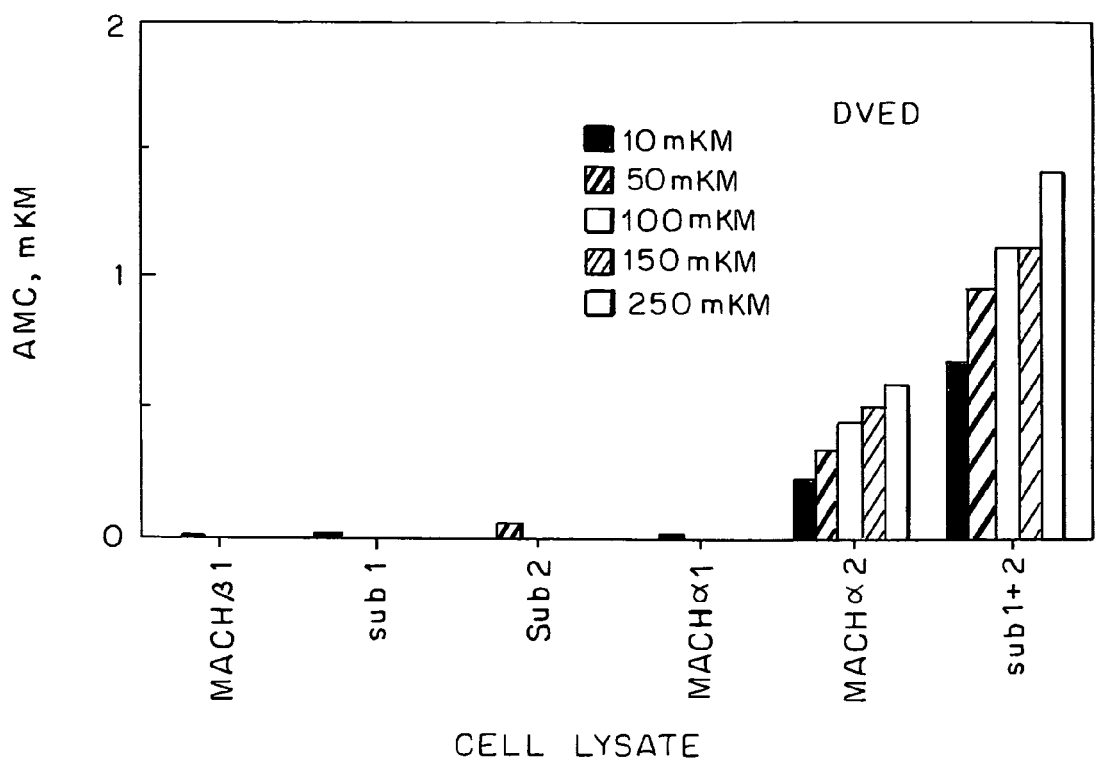
Figure 12F:
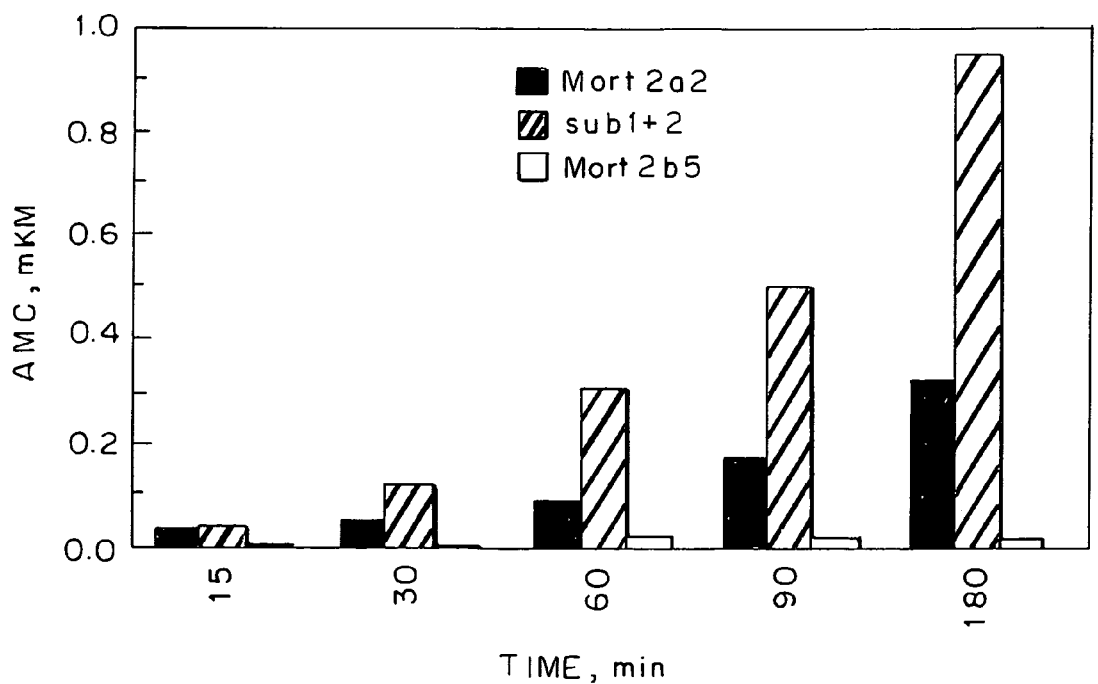

FIG. 10 shows a diagrammatic representation of the various MACH isoforms. Coding regions are represented as boxed areas. The various domains within the coding regions are denoted by different shadings as follows: the MORT modules (▓); the three amino acid sequence blocks which occur in different combinations in the isoforms. Positions of the residues in the CED3/ICE homology region implicated in the catalytic activity of ICE based on its X-ray crystal structure are shown. The catalytic cysteine residue is also indicated by a star (★). Those parts of the MACHα1 nucleotide sequence that are missing in the sequences of other isoforms are indicated in the diagrams of the latter isoforms by V-shaped connecting lines. The lengths of these cDNA-regions, which probably correspond to distinct exons, are indicated below the diagram of MACHα1. Lack of the 65 nucleotides which in MACHα1 encode for 'block 2' causes alteration in MACHβ1 and MACHβ2 of the reading frame of the nucleotides that encode for 'block 3'. In those isoforms, therefore, these nucleotides encode other amino acids which together constitute their unique C-terminal region. On the other hand, in MACHβ3 and MACHβ4 the reading frame of block 3 is maintained, but absence of the nucleotides that encode the CED3/ICE region and part of the 3' noncoding region results in alteration of the reading frame of nucleotides further downstream. Because of this alteration, the most 5' part of this noncoding downstream region does encode 10 amino acids, which constitute the C-terminal region unique to these two isoforms (hatched). As indicated in the figure, only partial cDNA clones of MACHβ3 and MACHβ2 were obtained.

The isoforms were cloned from a human B cell cDNA library (MACHβ1), from a human thymus cDNA library (MACHα1 and α2) and from the mRNA of the human lymphoblastoid cells Raji (MACH2α1, α2, α3, β3, β4, and β5) and Daudi (MACHα2, β2, β3, β4, and β5). Cloning from the mRNA of the Raji and Daudi cells was done by RT-PCR, using oligonucleotides corresponding to a 3' noncoding region and to a sequence within the second MORT module in MACHβ1. The starting codon of clones isolated in that way is therefore located within the second MORT module. The cDNA sequence and amino acid sequence of the MACH isoforms are presented in the sequence listing and identified as follows in Table 4.

TABLE 4

| MACH isoform | cDNA Sequence | Amino Acid Sequence |
| --- | --- | --- |
| MACHα1 | SEQ ID NO: 14 | SEQ ID NO: 7 |
| MACHα2 | SEQ ID NO: 17 | SEQ ID NO: 18 |
| MACHα3 | SEQ ID NO: 19 | SEQ ID NO: 20 |
| MACHβ1 | SEQ ID NO: 4 | SEQ ID NO: 5 |
| MACHβ2 | SEQ ID NO: 21 | SEQ ID NO: 22 |
| MACHβ3 | SEQ ID NO: 23 | SEQ ID NO: 8 |
| MACHβ4 | SEQ ID NO: 24 | SEQ ID NO: 25 |
| MACHβ5 | SEQ ID NO: 33 | SEQ ID NO: 34 |

The sequences in the different isoforms relate to each other as follows: (a) All the MACH isoforms share a common 182-amino acid N-terminal region which encompasses the MORT modules, yet vary carboxy terminally (3' downstream) to these modules, as well as in their noncoding regions. (b) On the basis of their C terminal sequences, the isoforms fall into two subgroups: four isoforms defined as subgroup β, have different C-termini due to alteration in the reading frame. Two (MACHβ1 AND β2) share the C-terminus found in the isoform initially cloned in the two-hybrid screen and two (MACHβ3 and β4) share a different C-terminus; three isoforms, defined as subgroup α, have a much longer C-terminal region that closely resemble proteases of the CED3/ICE family (see below); (c) The regions extending between the MORT module region and the C terminal region that defines the subgroups varied from one isoform to another. However, close examination showed that these intermediate regions consist of different combinations of the same three amino acid sequence blocks (blocks 1, 2 and 3). The variations of amino acid sequence among the different clones reflect two kinds of variations in nucleotide sequence, that most likely occur by alternative splicing: (a) insertion or absence of either of two nucleotide sequences one of 45 nucleotides (nts) and the other of 65 nts, or of both, below the nucleotides encoding Lys184; (b), presence of an additional insert within the region which in MACHβ1 constitutes the 3' noncoding part. These variations affect both the reading frame and the length of the protein.

Figure 11B:
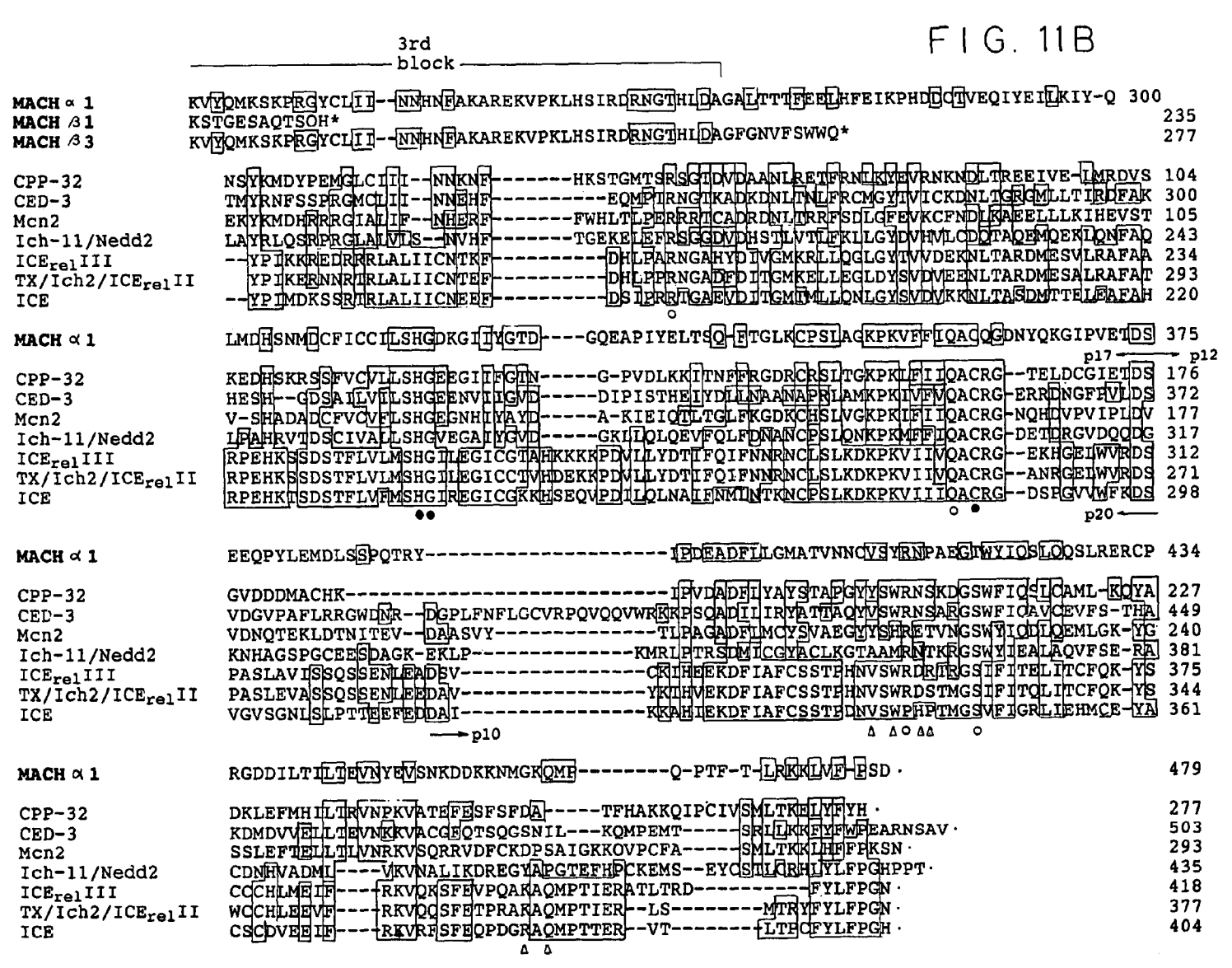

Part of the MACH isoforms encompass a CED3/ICE homolog. Data bank search revealed that the C terminal region of MACH isoforms including block 3 and the sequence extending downstream of it, closely resemble proteases of the CED3/ICE family. FIG. 11 presents sequence comparison of this region in MACH and the various known human members of this family as well as the *Caenorhabditis elegans* ced3 protein. CED3 (Ellis and Horvitz, 1986; Yuan et al, 1993), and the known human proteases of the CED3/ICE protease family: CPP32 (Fernandes-Alnemri et al, 1994), also called apopain (Nicholson et al, 1995) and Yama (Tewari et al, 1995b), Mch2α (Fernandes-Alnemri et al, 1995), Ich-1 (Wang et al, 1994; the human homolog of the mouse Nedd2 protein, Kumar et al, 1994), $ICE_{rel}II$ (Munday et al, 1995), $ICE_{rel}III$ (Munday et al 1995), also called TX and Ich2 (Faucheu et al, 1995; Kamens et al, 1995), and ICE (Thornberry et al, 1992; Cerretti et al, 1992). FIG. 11 depicts schematically the colinear amino acid sequence alignment of the MACH isoforms and the various known members for the CED/ICE protease family. Shown are the amino acid sequences of MACHα1, MACHβ1, MACHβ3 as well as of the *Caenorhabditis elegans* protease CED3, and of the known human proteases of the CED3/ICE protease family.

The above C-terminal region of MACH most closely resembles CPP32 (with 41% identity and 62% homology) and CED3 (with 34% identity and 56% homology). It shows a significantly lesser similarity to ICE (with 28% identity an 50% homology) and to its closely related homologs $ICE_{rel}II$ (also called TX and Ich2) and $ICE_{rel}III$. The similarity was observed throughout almost the whole region starting from Tyr226 within block 3, to the C terminus of the MACHα isoforms.

Two points of similarity are particularly notable:

(a) All known proteases of the CED3/ICE family cleave proteins at sites defined by the occurrence of Asp at the P1 position and a small hydrophobic amino acid residue at P1'. Their specificity differs, though, with regard to other structural features of the substrate, including the nature of the residues at positions P2-P4. Accordingly, the active site residues involved in catalysis (corresponding to His237, Gly238 and Cys285 in ICE) and in the binding pocket for the carboxylate side chain of the P1 Asp (Arg179, Gln283, Arg341 and probably also Ser347) are conserved among these proteases. As shown in FIG. 11, these residues (marked by shading of the residues and by full and empty circles below the sequences) are also conserved in MACHα1. There is one exception, though—a conservative change of Ser to Thr at the site corresponding to Ser347 of ICE. Another slight, yet potentially important, sequence difference between MACHα isoforms and other members of the protease family is an Arg to Gln replacement of the residue corresponding to Arg286 of ICE. This residue, which is adjacent to the putative catalytic cysteine residue, is fully conserved in all other CED3/ICE family members. Also part of the residues at the sites located close to the substrate P2-P4 residues (marked by triangles below the sequences in FIG. 11) differ in the MACHα isoforms from those found in other CED3/ICE family members.

(b) Proteases of the CED3/ICE family contain sites of autocleavage. Several of the proteases are known indeed to be self-processed, and to depend on this processing for displaying maximal catalytic activity. Their fully bioactive form is composed of two noncovalently-associated cleavage products, which differ in size (p20 and p17 in ICE; p17 and p12 in CPP32, as marked by arrows in FIG. 11). Presence of potential sites of autocleavage in other members of the family suggests that they are subject to similar processing, and, similarly, depend on this processing for exhibiting maximal activity. Such potential sites of autocleavage occur in MACHα1 almost at the same locations as in the CPP32 (see shaded boxes in FIG. 11). The site corresponding to the N-terminus of the p17 subunit of CPP32 is located in the second conserved block of amino acids, just a few amino acids upstream to the N terminus of the CED3/ICE-homology region (below Asp216). The site corresponding to the point of cleavage between the two subunits of CPP32 is located, as in all other members of the CED3/ICE family that are known to be cleaved, a few amino acids downstream to the catalytic cysteine residue (below Asp374). This conservation suggests that the CED3/ICE homology region in MACHα1 is subject to proteolytic processing. The sizes of the two expected products of this cleavage are very close to that of the two subunits of the processed CPP32 molecule.

(c) The CED3/ICE Homology Region in MACH has Proteolytic Activity.

To find out if the CED3/ICE homology region in MACHα possesses proteolytic activity, applicants expressed the region that extends from the potential cleavage site upstream to this region, between Asp216 and Ser217, till the C terminus of the protein in bacteria, as a GST fusion protein. The bacterial lysates were examined for ability to cleave fluorogenic peptide substrates, shown before to be cleaved by other CED3/ICE homologs. Two substrate peptides were used: The first, Acetyl-Asp-Glu-Val-Asp-a-(4-Methyl-Coumaryl-7-Amide) (AC-DEVD-AMC), corresponds to a sequence in poly (ADP-ribose)polymerase (PARP), a nuclear protein found to be cleaved in cells shortly after FAS-R stimulation (Tewari et al, 1995b), as well as in other apoptopic processes (Kaufmann, 1989; Kaufmann et al 1993; Lazebnik et al, 1994). This fluorogenic substrate is cleaved effectively by CPP32. The second fluorogenic substrate, Acetyl-Tyr-Val-Ala-Asp-AMC (Ac-YVAD-AMC), corresponds to a substrate site for ICE in the IL-1β precursor. This fluorogenic substrate is cleaved by ICE. As shown in FIGS. 12A-F and 13A-B, lysates of bacteria expressing the CED3/ICE homology region in MACHα1 cleaved effectively the PARP sequence-derived fluorogenic substrate. They had no measurable proteolytic activity, though, against the IL-1β-precursor sequence-derived fluorogenic substrate (controls), Ac-YVAD-AMC, which is an ICE cleavage site in IL-1β-precursor (Thornberry et al, 1992). The proteolytic activity was blocked by iodacetic acid (5 mM), confirming that it is mediated by a thiol protease. No cleavage was observed with lysates containing the GST-fused MACH CED3/ICE-homology region in which the catalytic cysteine residue $Cys_{360}$ was replaced by Ser. Also, lysates from bacteria that expressed the full-length MACHα1 protein as a GST-fusion protein did not cleave Ac-DEVD-AMC, probably because of the absence of bacterial enzymes capable of processing the full-length molecule. Nor did cleavage occur with lysates containing either of the two potential cleavage products of the CED3/ICE homology region.

FIGS. 12A-F and 13A show the kinetics of cleavage of the PARP sequence-derived fluorogenic substrate, Ac-DEVD-AMC (50 μM), by extracts of *E. coli* expressing a GST-fusion protein of the CED3/ICE homology region in MACHα1 (Ser217 through the C-terminus of the protein) as compared to the lack of cleavage by extracts of bacteria expressing GST-fusion proteins of the full-length MACHα1 molecule or of either one of the two potential proteolytic products of the CED3/ICE homology region (Ser217 till Asp374 and Asp374 through the C-terminus of the protein).

Figure 13B:
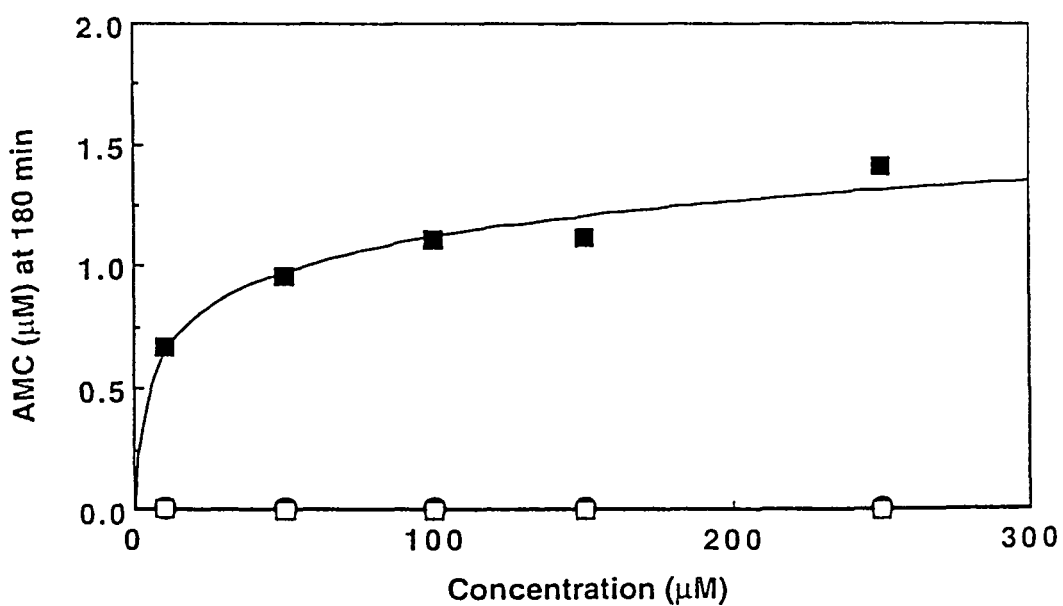

It also shows the substrate concentration-dependence of the cleavage of Ac-DEVD-AMC, incubated for 180 min. with extracts of bacteria expressing the MACHα1 CED3/ICE homology-region in fusion with GST (see FIG. 13B). No cleavage was observed in the presence of iodoacetic acid (5 mM). The extracts had no activity on Ac-YVAD-AMC, a fluorogenic substrate corresponding to a substrate site for ICE in the IL-1β precursor.

Briefly, the GST-fusion proteins were produced in XL1-blue bacteria using the pGEX3 expression vector. The bacteria were lysed by sonication in a buffer containing 25 mM HEPES (pH 7.5), 0.1% 3-[3-cholamidopropyl)di-methylamino]-1-propanesulfonate, 5 mM EDTA and 2 mM DDT, followed by centrifugation at 16,000×g for 10 min. SDS-PAGE analysis confirmed the presence of similar levels of the various fusion proteins in the lysates (not shown). 50 μl aliquots of the extracts (4 mg/ml of total protein) were incubated at room temperature for the indicated periods in a 500 μl total volume reaction with the fluorogenic substrates, at the indicated concentrations. AMC release was measured by spectrofluorometry at an excitation wavelength of 380 nm and an emission wavelength of 460 nm. The concentration of AMC was determined from a standard curve. Both fluorogenic substrate peptides were obtained from Peptide Institute Inc. (Osaka, Japan). Other CED3/ICE proteases were shown to exhibit full activity only after proteolytic processing, which occurs either by self-cleavage, or via their cleavage by other proteases (reviewed in Kumar, 1995; Henkart, 1996). Applicants' observation that lysates of bacteria that express GST-MACHα1 molecules do not possess enzymatic activity, as opposed to the activity observed in lysates of bacteria that express the CED3/ICE homology region, suggests that processing is also required for MACHα activity. The way in which MACHα processing occurs within the mammalian cell, and how this processing is brought about by FAS-R or p55-R triggering, is not known. MORT-1 has been shown to bind in cells to acitivated FAS-R together with some other proteins (Kischkel et al, 1995). These proteins are likely to include MACHα1 and other MACH isoforms. It seems plausible that the binding of MORT-1 in association with MACHα to FAS-R brings together several MACH molecules, or induces conformational changes in them, and that these changes either trigger autolytic processing of MACHα or make MACHα susceptible to cleavage by other proteases. Stimulation of p55-R may trigger self-processing of MACHα in a similar, though less direct manner, by brining together several TRADD molecules, or inducing a conformational change in them, which in turn induces a change in the formation or state of aggregation of MORT-1 and its associated MACH molecule.

The substrate specificity of MACHα seems to be rather 'death oriented'. Although it could cleave a substrate peptide corresponding to a cleavage site in the death substrate PARP (Ac-DEVD-AMC), MACHα showed no proteolytic activity towards a peptide corresponding to the site of processing of the IL-1β precursor by ICE (Ac-YVAD-AMC). Identification of the cellular proteins that serve as substrates for cleavage by MACHα will elucidate the more downstream events in death induction by this protease. Likely substrates for MACHα cleavage are other members of the CED3/ICE family, like CPP32 and ICE. Some of these proteases are indeed processed after FAS-R or TNF receptor-triggering (Miura et al, 1995; Schlegel et al, 1996; Chinnaiyan et al, 1996). Perhaps proteases that do not belong the CED3/ICE family are also activate by MACHα, either directly or through the action of other CED3/ICE proteases. Involvement of multiple proteases in the cell death process is consistent with the reported ability of inhibitors of various proteases, including inhibitors of serine proteases and an inhibitor of ICE cleavage as well as antisense ICE cDNA, to protect cells from FAS-R and TNF receptor-induced toxicity (Weitzen and Granger, 1980; Ruggiero et al, 1987; Enari et al, 1995; Los et al, 1995).

A variety of other enzymes, including phospholipases, sphingomyelinases and protein kinases, may participate in cell death induction by the TNF receptors and FAS-R (see Eischen et al, 1994; Vandenabeele et al, 1995; Cifone et al, 1995 and references therein). Some of these enzymes may become activated by the proteolytic cleavage initiated by MACHα. It also seems possible, however, that at least part of these other death-related activities are stimulated by distinct signaling routes, independently of MACHα stimulation. Involvement of more than one signaling cascade in the induction of cell death, some common to p55-R and Fas/APO1 and some induced by only one of them, would be consistent with report on both shared and distinct features of cell death processes induced by the two receptors (Grell et al, 1994; Schulze-Osthoff et al, 1994; Wong and Goeddel, 1994; Clement and Stamenkovic, 1994).

(d) MACHα1 Binds to MORT1 as well as to MACHβ1:

To find out if MACHα1 can bind to MORT1, as does MACHβ1, the interaction of the proteins within transfected yeasts was first examined. MACHα1 appeared to have a significant cytotoxic effect on the yeasts. This effect was manifested in a marked decrease in the yield of colonies in yeasts that expressed the protein in the activation domain (AD) vector (whose expression level is higher than that of the DNA binding domain (DBD) vector). On the other hand, MACHβ1 in which the catalytic cysteine residue, $Cys_{360}$, was replaced with Ser (MACHα1 (C360S)) was not cytotoxic to either mammalian cells (see below), or yeast. Like MACHβ1, MACHα1 (C360S) bound in tranfected yeast to MORT-1 and also to itself. It also bound to MACHβ1. Also, yeast expressing the wild-type MACH.dbd.1 together with MORT-1 or MACHβ1 exhibited interaction of the transfected proteins. The intensity of the lacZ-product color varied, however, among the yeast colonies; in yeasts tranfected with MACHα1 in both the AD and the DBD vectors no color product was observed, probably because of the cytotoxic effect of the wild-type MACHα1. Yet, in spite of this variation, yeasts expressing MACHα1 either in combination with MORT1 or in combination with MACHβ1 scored clearly positive for interaction of the transfected proteins. Unlike MACHβ1, MACHα1 did not exhibit self-interaction in the two hybrid test (FIG. 5).

Both MACHα1 (C360S) and MACHβ1 coimmunoprecipitated with MORT-1 from lysates of human embryonic kidney 293-EBNA cells, indicating that they bind to MORT-1 also in mammalian cells. Testing further if MACHα1 can bind to MORT1 also within mammalian cells, MACHα1 or MACHβ1, fused with the FLAG octapeptide was expressed, together with HA epitope-tagged MORT1 molecules. $^{35}$[S] metabolically labeled MACHα1 and MACHβ1 fused at their N-termini to the FLAG octapeptide (FLAG-MACHα1 and β1), and MORT1 fused at its N terminus to the HA epitope (Field et al, 1988) were expressed in HeLa cells. Immunoprecipitation of the proteins from lysates of the cells was performed using mouse monoclonal antibodies against the FLAG octapeptide (M2; Eastman Kodak), HA epitope (12CA5, Field et al, 1988) or the p75 TNF receptor (#9, Bigda et al, 1994) as a control. The proteins were analyzed by SDS-polyacrylamide gel electrophoresis (12% acrylamide), followed by autoradiography. Both MACHα1 and MACHβ1 co-immunoprecipitated with MORT1 from lysates of the cells, indicating that they bind to MORT1. The effectivity of interaction of MACHα1 with MORT1 appeared to be lower than that of MACHβ1.

(e) MACH Molecules that Contain the CED3/ICE Homology Region can Mediate Cell Death:

To explore the involvement of MACH in cell-death induction, the effect of overexpression of various MACH isoforms on cell viability was examined. The test was performed by transfecting MACH expression vectors together with a β-galactosidase expression vector as a transfection marker into human embryonic kidney 293-EBNA cells and breast carcinoma MCF7 cells.

In brief, 293-EBNA cells, MCF7 human breast carcinoma cells and HeLa HtTA-1 cells were grown in Dulbecco's modified Eagle's minimal essential medium supplemented with 10% fetal calf serum, nonessential amino acids, 100 U/ml penicillin and 100 µg/ml streptomycin. Cell tissue culture dishes ($5 \times 10^5$ 293-EBNA cells, $3 \times 10^5$ s MCF7 cells or $3 \times 10^5$ HeLa cells in 6-cm dishes) were transiently transfected, using the calcium phosphate precipitation method, with the cDNAs of the indicated proteins together with the β-galactosidase expression vector. In the experiments presented in FIGS. 14A-D and 15, each dish was transfected with 3.5 µg of the indicated MACH construct and 1.5 µg of pSV-β-gal. In the experiments presented in FIGS. 16A-D and 17-19, each dish was transfected with 2.5 µg of the indicated MACH or MORT1 construct (or, as control, empty vector) and 1.5 µg of pSV-β-gal. The cells were rinsed 6 to 10 h after transfection. The 293-EBNA and MCF7 cells were incubated for a further 18 h without additional treatment. The HeLa cells were incubated for 26 h after transfection and-then for 5 h in the presence of either anti-Fas.APO1 antibody (CH11, 0.5 µg/ml) or TNF (100 ng/ml), together with cycloheximide (10 µg/ml). The extent of cell death at the end of the incubation periods was assessed by determination of β-galactosidase expression, as described by Kumar et al, 1994.

Figure 14A:
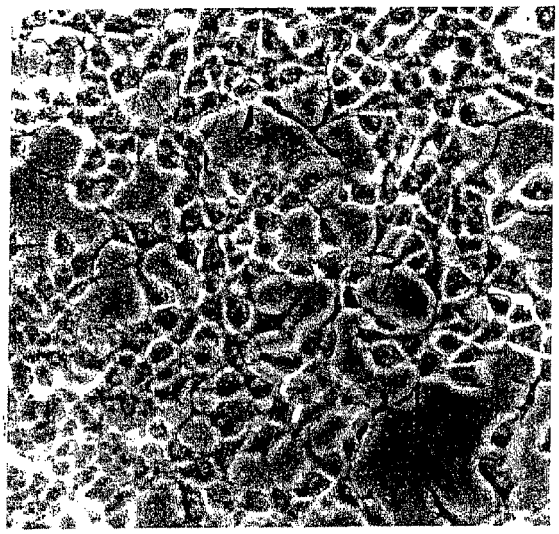
FIGS. 14A-D show cell death mediated by MACHα1 and MACHα2.
Figure 14B:
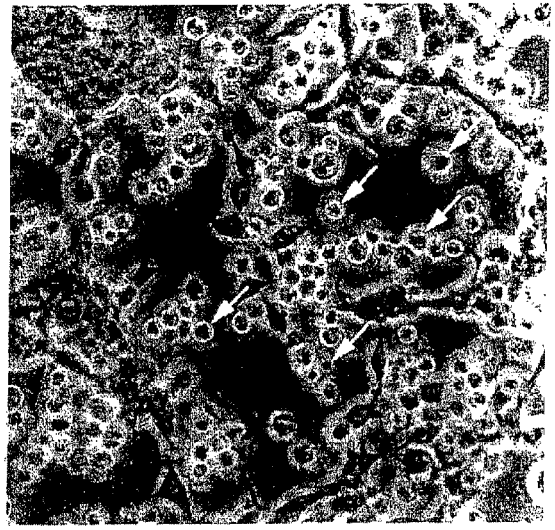
Figure 14C:
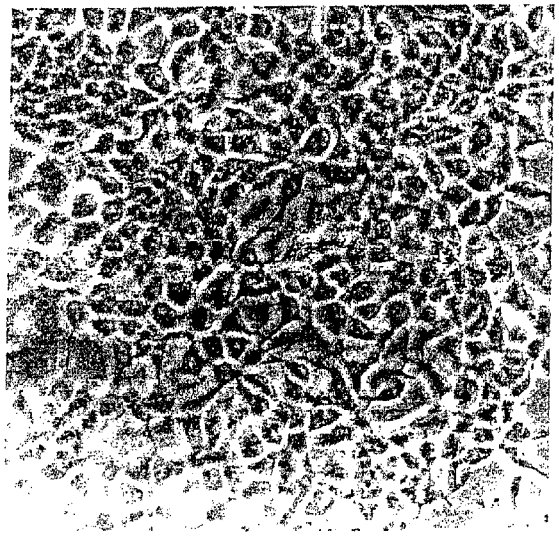
Figure 14D:
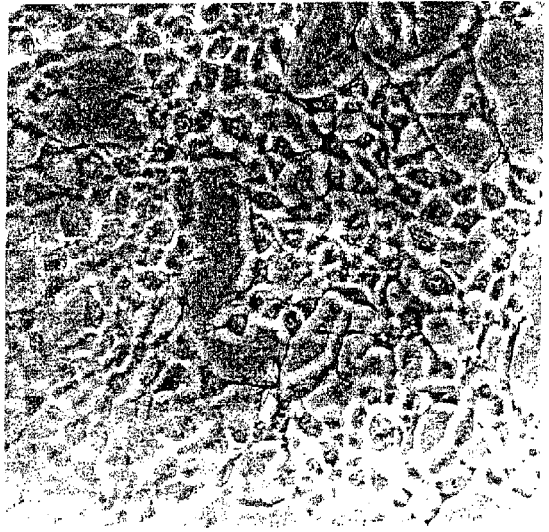

Cultures transfected with an expression vector of either MACHα1 or MACHα2 exhibited massive cell death, manifested by cell rounding, blebbing, contraction, and finally detachment of cells from the dish (FIG. 14B). By 20 h after transfection, the majority of the transfected cells, identified by β-galactosidase staining (X-Gal), showed condensed morphology typical of apoptosis (FIG. 14B). In contrast, cells expressing the empty vector remained viable.

Figure 15:
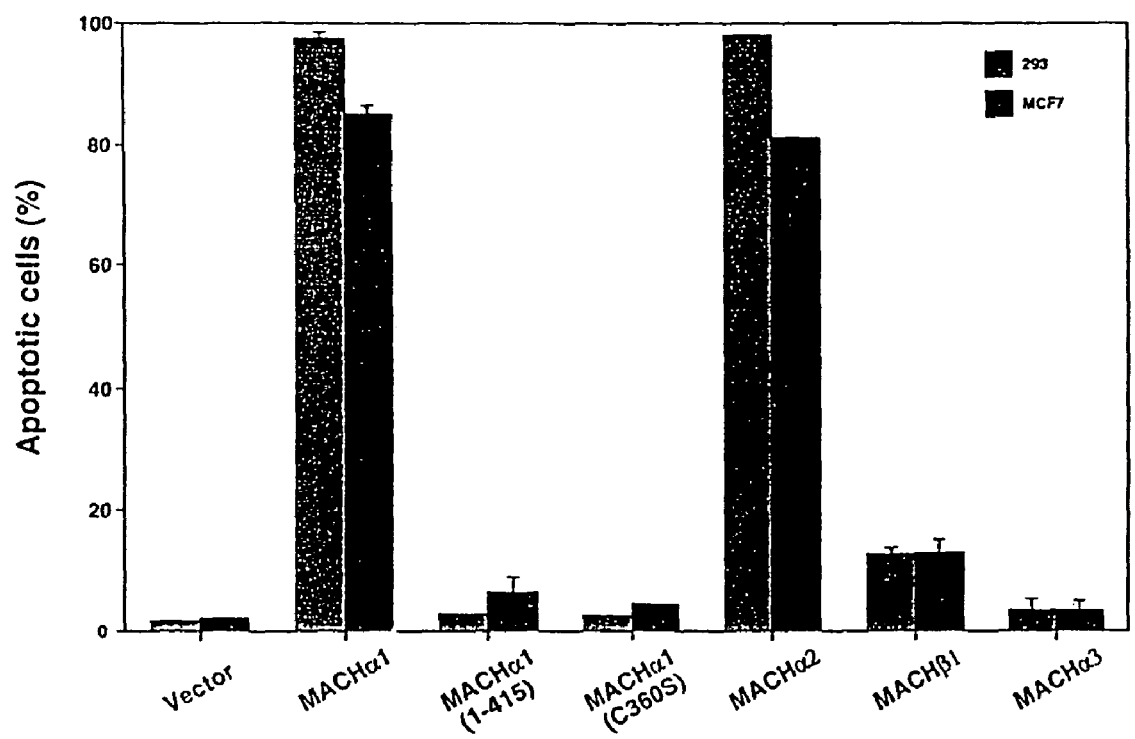
FIG. 15 depict graphically cell death mediated by MACHα1 and MACHα2.

In particular, FIGS. 14A-D show the morphology of human embryonic kidney 293-EBNA cells transiently expressing the indicated MACH isoforms. The arrows (FIG. 14B) point to apoptopic cells. Photographs were taken 26 h after transfection. FIG. 15 shows the quantification of MACH-induced death of the 293-EBNA (striped squares) and MCF7 (black squares) cells by determination of the portion of β-galactosidase-expressing cells exhibiting apoptopic morphology 20 h after transfection of the indicated constructs. Data are from three independent experiments with the 293-EBNA cells and two independent experiments with the MCF7 cells. They are expressed as the mean percentage of the blue cells exhibiting signs of apoptosis as a fraction of the total number of blue cells counted (about 500 cells per sample).

Figure 19:
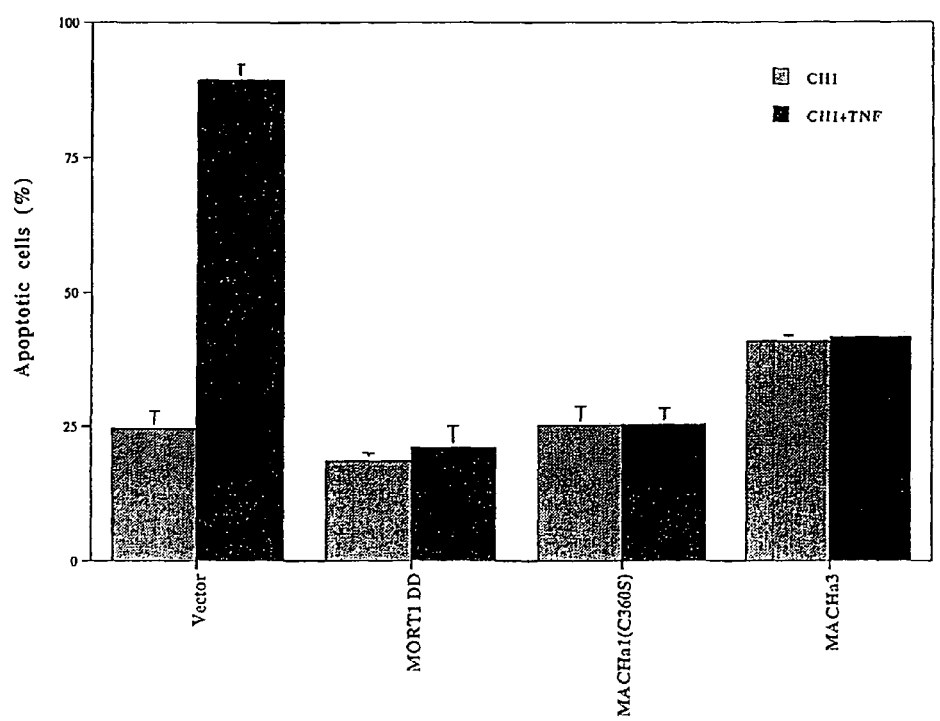
FIG. 19 shows death of HeLa cells that transiently express FAS/APO1.

To examine the involvement of the CED3/ICE homology region within the MACHα isoforms in their apoptotic effects, cells were transfected with the expression vector for the MACHβ1 isoform, which lacks the CED3/ICE homology region, as well as with expression vectors for MACHα3, which lacks an N-terminal part of the region, and with expression vectors for MACHα1 (C360S) and for a C-terminally truncated mutant of MACHα1 (MACHα1 (1-415)), which lacks one of the residues believed to be critical for CED3/ICE protease function (corresponding to $Ser_{347}$ in ICE). No death (beyond the slight amount observed in cells transfected with an empty expression vector) occurred in 293-EBNA or MCF7 cells transfected with the expression vectors for MACHα3, MACHα1 (1-415) or MACHα1 (C360S). Moreover, cells transfected with MACHα1 together with these vectors also exhibited very little cell death, indicating that MACH molecules that contain an incomplete CED3/ICE region have a negative dominant effect on the activity of the wild-type molecules. Cultures expressing MACHβ1, which does not contain the CED3/ICE-region at all, did exhibit some slight cell death (FIG. 15). This effect of MACHβ1, which most probably results from activation of endogenous MACHα1 molecules, was for some reason more pronounced in transfected HeLa cells. Moreover, in HeLa cells MACHα3, MACHα1 (1-415) and MACHα1 (C360S) were also somewhat cytotoxic (FIG. 19).

FIG. 8 diagrammatically presents the receptor and target protein interactions participating in induction of cell death by FAS/APO1 (FAS-R) and p55-R. MACHα activity appears to constitute the most upstream enzymatic step in the cascade of signaling for the cytocidal effects of FAS/APO1 and p55-R. The ability of MACHβ1 to bind to both MORT-1 and MACHα1 suggests that this isoform enhances the activity of the enzymatically active isoforms. It is possible that some of the MACH isoforms serve additional functions. The ability of MACHβ1 to bind to both MORT-1 and MACHα1 suggests that this isoform might enhance the activity of the enzymatically active isoforms. The mild cytoxicity observed in 293-EBNA and MCF7 cultures transfected with this isoform and the rather significant cytoxic effect that it exerts in HeLa cells probably reflect activation of endogenously expressed MACHα molecules upon binding to the transfected MACHβ1 molecules. Conceivably, some of the MACH isoforms could also act as docking sites for molecules that are involved in other, non-cytoxic effects of Fas/APO1 and TNF receptors.

(f) Blocking of MACHα Function Interferes with Cell Death Induction by Fas/APO1 and p55-R To assess the contribution of MACHα to Fas/APO1 (FAS-R) and p55-R cytotoxicity, MACHα3, as well as the nonfunctional MACHα1 mutants, MACHα1 (1-415) and MACHα (C360S), were expressed in cells that were induced to exhibit this cytotoxicity. p55-R-induced cytotoxicity was triggered in the 293-EBNA cells by transient over-expression of this receptor (Boldin et al, 1995a), and Fas/APO1 cytotoxicity by over-expression of chimeric molecules comprised of the extracellular domain of the p55-R and the transmembrane and intracellular domains of Fas/APO1. For some reason, this chimera had a far greater cytotoxic effect than that of the normal Fas/APO1. Cytotoxic activities in HeLa cells was also induced by treating them with TNF or anti-Fas/APO1 antibody in the presence of the protein-synthesis blocker cycloheximide. The HeLa cells were made responsive to Fas/APO1 by transient expression of this receptor. In all systems examined, MACHα3 and the nonfunctional MACHα1 mutants provided effective protection against the cytotoxicity induced by Fas/APO1 or p55-R triggering (FIGS. 16-19). Such protection was also observed, as previously reported (Hsu et al, 1996; Chinnaiyan et al, 1996), in cells transfected with a MORT1 N-terminal deletion mutant that lacks the MACH-binding region (MORT1 (92-208)). These protective effects indicate that MACHα is a necessary component of both the Fas/APO1- and the p55-R-induced signaling cascades for cell death.

Figure 16A:
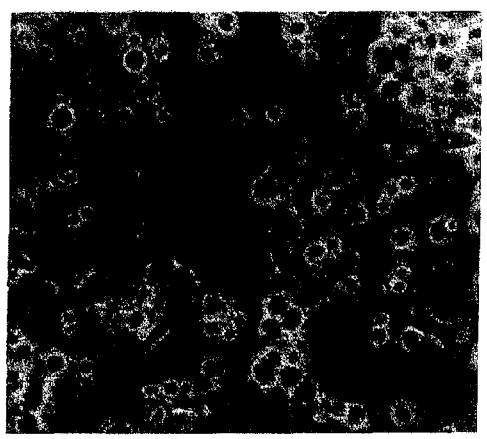
FIGS. 16A-D show the morphology of cells in which cell death was induced or blocked.
Figure 16B:
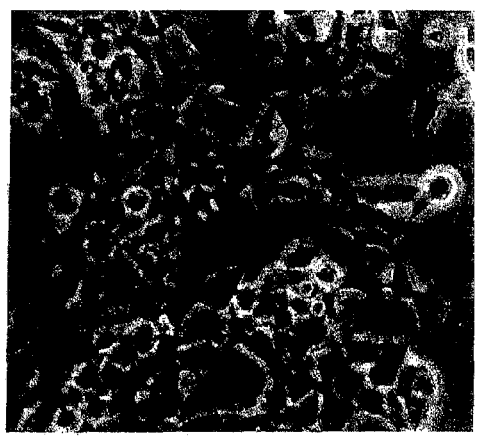
Figure 16C:
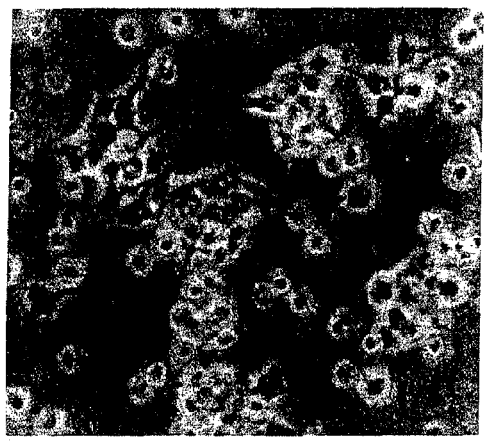
Figure 16D:
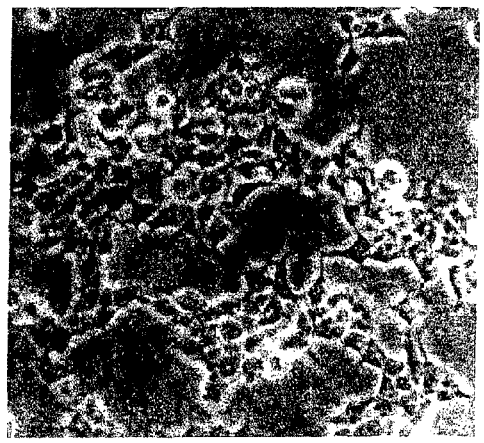
Figure 17:
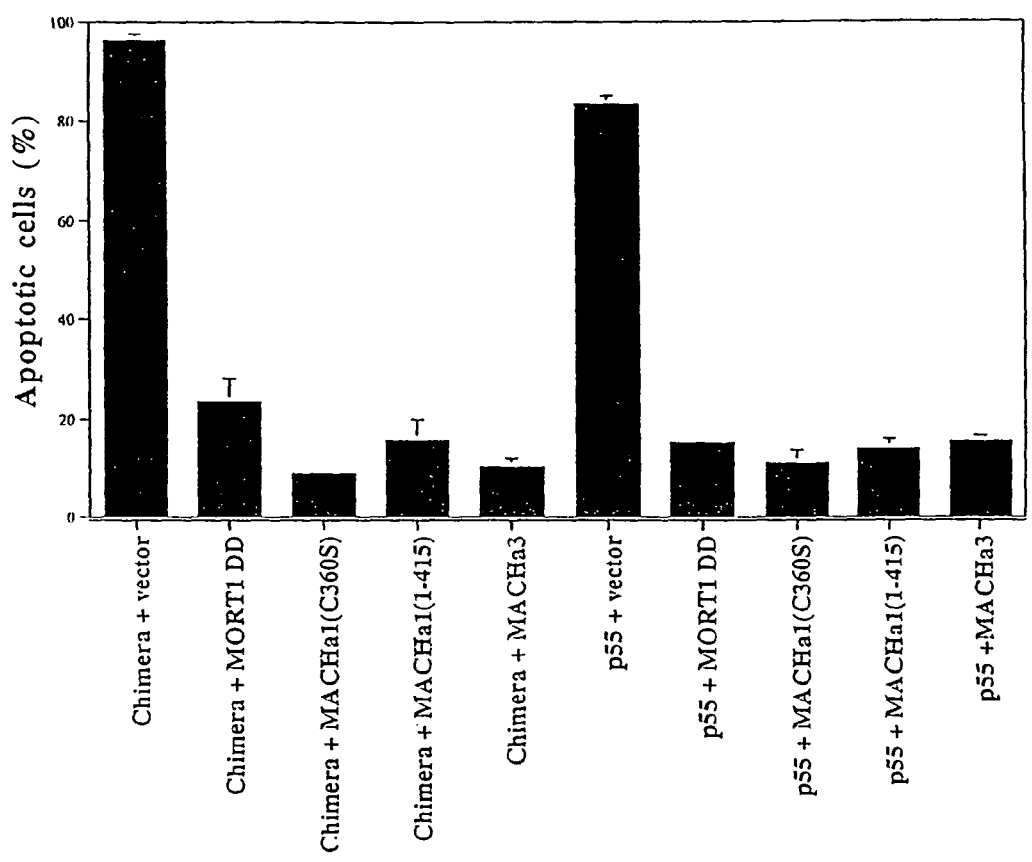
FIG. 17 graphically shows that MACHα molecules that contain a non-functional CED3/ICE region block cell death. induction by p55-R.
Figure 18:
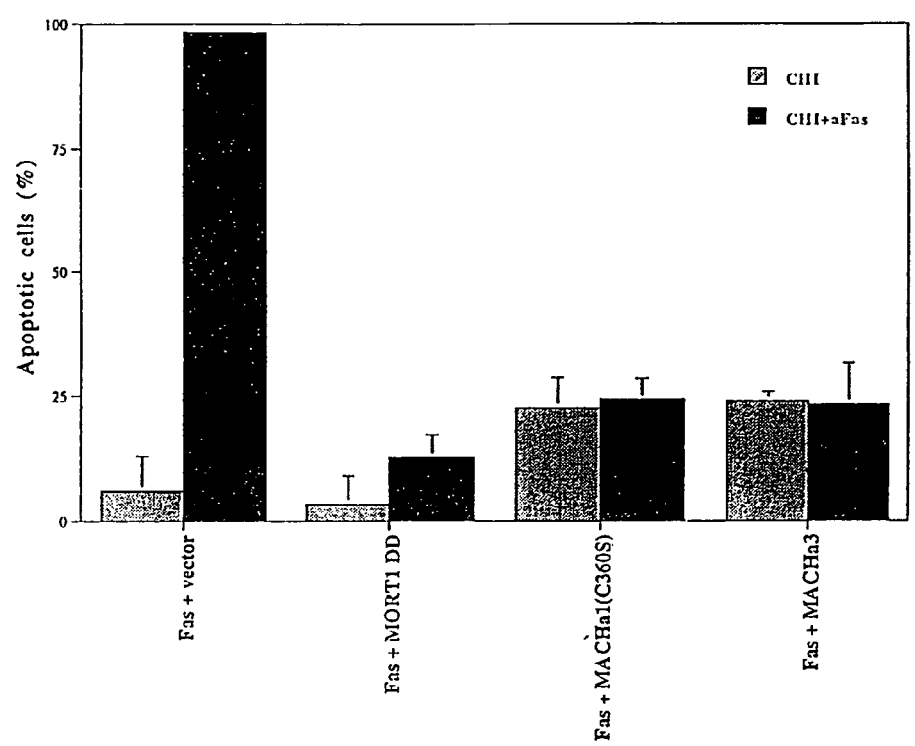
FIG. 18 shows that MACHα molecules that contain a non-functional CED3/ICE region block cell death induction by FAS/APO1.

In particular, FIGS. 16A-D show morphology of 293-EBNA cells in which cell death was induced by transient expression of a chimera comprised of the extracellular domain of the p55-R (amino acids 1-168) fused to the transmembrane and intracellular domains of Fas/APO1 (amino acids 153-319) (p55-Fas chimera) (FIGS. 16A and 16B), or by expression of the p55-R (FIGS. 16C and 16D), and of cells that were protected from these cytotoxic effects by their simultaneous transfection with MACHα1 (C360S) (FIGS. 16B and 16D). Photographs were taken 26 h after transfection. FIG. 17 illustrates the quantification of death induced in 293-EBNA cells by their transfection with p55-Fas chimera or with p55-R, together with an empty vector, a MORT1 deletion mutant lacking the MACH-binding region (MORT1 (92-208)), or MACHα molecules containing a nonfunctional CED3/ICE region. FIG. 18 shows the death of HeLa cells that transiently express Fas/APO1, induced by treatment with anti-Fas/APO1 antibody (aFas) and cycloheximide (CHI), and its prevention by cotransfection of MORT1DD (92-208), MACHα (C360S) or MACHα3. FIG. 19 shows the death of HeLa cells induced by application of TNF and cycloheximide (CHI), and its prevention as in FIG. 18. Data are from at least two independent experiments and are expressed as in FIGS. 14A-F and 15.

MACH is expressed in different tissues at markedly different levels and apparently also with different isotype patterns. These differences probably contribute to the tissue-specific features of response to the Fas/APO1 ligand and TNF. As in the case of other CED3/ICE homologs (Wang et al, 1994; Alnemri et al, 1995), MACH isoforms containing incomplete CED3/ICE regions (e.g. MACHα3) are found to inhibit the activities of coexpressed MACHα1 or MACHα2 molecules; they are also found to block death induction by Fas/APO1 and p55-R. Expression of such inhibitory isoforms in cells may constitute a mechanism of cellular self-protection against Fas/APO1- and TNF-mediated cytotoxicity. The wide heterogeneity of MACH isoforms, which greatly exceeds that observed for any of the other proteases of th CED3/ICE family, should allow a particularly fine tuning of the function of the active MACH isoforms.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Adelman et al, "In vitro deletional mutagenesis for bacterial production of the 20,000-dalton form of human pituitary growth hormone", *DNA* 2(3):183-193 (1983)

Alnemri et al, "Cloning and expression of four novel isoforms of human interleukin-1 beta converting enzyme with different apoptotic activities", *J Biol Chem* 270:4312-4317 (1995)

Ausubel et al, eds., *Current Protocols in Molecular Biology* Greene Publishing Associates, Inc./and Wiley & Sons, Inc., New York, pp. 8.1.1-8.1.6 and 16.7-16.7.8 (1994)

Ausubel et al, *Current Protocols in Molecular Biology*, Greene Publications and Wiley Interscience, New York, N.Y., 1987-1995

Barinaga M, "Ribozymes: killing the messenger," *Science* 262(5139):1512-1514 (1993)

Beidler et al, "The baculovirus p35 protein inhibits Fas- and tumor necrosis factor-induced apoptosis", *J Biol Chem* 270(28):16526-16528 (1995)

Berger et al, "Secreted placental alkaline phosphatase: a powerful new quantitative indicator of gene expression in eukaryotic cells," *Gene* 66(1):1-10 (1988)

Better et al, "*Escherichia coli* secretion of an active chimeric antibody fragment", *Science* 240:1041-1043 (1988)

Beutler et al, "Cachectin: more than a tumor necrosis factor", *N Engl J Med* 316(7):379-385 (1987)

Bigda et al, "Dual role of the p75 tumor necrosis factor (TNF) receptor in TNF cytotoxicity", *J Exp Med* 180(2):445-460 (1994)

Biswas D K, "Gene Amplification", U.S. Pat. No. 4,766,067, issued Aug. 23, 1988

Boldin et al, "Self-association of the "death domains" of the p55 tumor necrosis factor (TNF) receptor and Fas/APO1 prompts signaling for TNF and Fas/APO1 effects", *J Biol Chem* 270(1):387-391 (1995a)

Boldin et al, "A novel protein that interacts with the death domain of Fas/APO1 contains a sequence motif related to the death domain", *J Biol Chem* 270(14):7795-7798 (1995b)

Boulianne et al, "Production of functional chimaeric mouse/human antibody", *Nature* 312(5995):643-646 (1984)

Brakebusch et al, "Cytoplasmic truncation of the p55 tumour necrosis factor (TNF) receptor abolishes signalling, but not induced shedding of the receptor", *EMBO J* 11(3):943-950 (1992)

Brockhaus et al, "Identification of two types of tumor necrosis factor receptors on human cell lines by monoclonal antibodies", *Proc Natl Acad Sci USA* 87(8):3127-3131 (1990)

Cabilly et al, "Recombinant immunoglobin preparations" U.S. Pat. No. 4,816,567, issued Mar. 28, 1989; and "Recombinant immunoglobulin preparations, methods for their preparation, DNA sequences, expression vectors and recombinant host cells therefor", European patent 0 125 023, published Nov. 14, 1984

Cabilly et al, "Generation of antibody activity from immunoglobulin polypeptide chains produced in *Escherichia coli*." *Proc Natl Acad Sci USA* 81:3273-3277 (1984)

Cantor et al, "Ribozyme cleaves rex/tax mRNA and inhibits bovine leukemia virus expression", *Proc Natl Acad Sci*, 90(23):10932-10936 (1993)

Cerretti et al, "Molecular cloning of the interleukin-1 beta converting enzyme," *Science* 256(5053):97-100 (1992)

Chang et al, "Molecular conjugates containing cell membrane-blending agents" U.S. Pat. No. 5,149,782, issued Sep. 22, 1992

Chard T, "An Introduction to Radioimmune Assay and Related Techniques", in *Laboratory Techniques and Biochemistry in Molecular Biology*, Work et al (eds), North Holland Publishing Company, NY (1978)

Chen et al, "Inhibition of HIV-1 replication by novel multi-target ribozymes", *Ann NY Acad Sci* 660:271-273 (1992)

Chinnaiyan et al, "FADD/MORT1 is a common mediator of CD95 (Fas/APO-1) and tumor necrosis factor receptor-induced apoptosis", *J Biol Chem* 271(9):4961-4965 (1996)

Chinnaiyan et al, "FADD, a novel death domain-containing protein, interacts with the death domain of Fas and initiates apoptosis", *Cell* 81(4):505-512 (1995)

Chong K-T, "Treatment of infections with lymphokines", U.S. Pat. No. 4,879,111, issued Nov. 7, 1989

Cifone et al, "Multiple pathways originate at the Fas/APO-1 (CD95) receptor: sequential involvement of phosphatidylcholine-specific phospholipase C and acidic sphingomyelinase in the propagation of the apoptotic signal," *EMBO J* 14(23):5859-5868 (1995)

Clement et al, "Fas and tumor necrosis factor receptor-mediated cell death: similarities and distinctions," *J Exp Med* 180(2):557-567 (1994)

Colligan et al, *Current Protocols in Immunology*, Green Publishing Assoc., and Wiley Interscience, New York (1992-1996), Creighton T E, *Proteins: Structure and Molecular Properties*, W.H. Freeman & Co., San Francisco, Calif. (1983)

Crisell et al, "Inhibition of HIV-1 replication by ribozymes that show poor activity in vitro," *Nucleic Acids Res* 21(22):5251-5255 (1993)

David et al, "Immunometric assays using monoclonal antibodies", U.S. Pat. No. 4,376,110, issued Mar. 8, 1983

Dirks et al, "Dicistronic transcription units for gene expression in mammalian cells", *Gene* 128(2):247-249 (1993)

Durfee et al, "The retinoblastoma protein associates with the protein phosphatase type 1 catalytic subunit", *Genes Dev* 7(4):555-569 (1993)

Eischen et al, "Tyrosine kinase activation provides an early and requisite signal for Fas-induced apoptosis," *J Immunol* 153(5):1947-1954 (1994)

Ellis et al, "Genetic control of programmed cell death in the nematode *C. elegans,*" *Cell* 44(6):817-829 (1986)

Enari et al, "Involvement of an ICE-like protease in Fas-mediated apoptosis", *Nature* 375(6526):78-81 (1995)

Engelmann et al, "Two tumor necrosis factor-binding proteins purified from human urine. Evidence for immunological cross-reactivity with cell surface tumor necrosis factor receptors", *J Biol Chem* 265(3):1531-1536 (1990)

Faucheu et al, "A novel human protease similar to the interleukin-1 beta converting enzyme induces apoptosis in transfected cells," *EMBO J* 14 (9)-1914-1922 (1995)

Fernandes-Alnemri et al, "Mch2, a new member of the apoptotic Ced-3/Ice cysteine protease gene family," *Cancer Res* 55(13):2737-2742 (1995)

Fernandes-Alnemri et al, "CPP32, a novel human apoptotic protein with homology to *Caenorhabditis elegans* cell death protein Ced-3 and mammalian interleukin-1 beta-converting enzyme," *J Biol Chem* 269(49):30761-30764 (1994)

Field et al, "Purification of a RAS-responsive adenylyl cyclase complex from *Saccharomyces cerevisiae* by use of an epitope addition method", *Mol Cell Biol* 8(5):2159-2165 (1988)

Fields and Song, "A novel genetic system to detect protein-protein interactions," *Nature* 340(6230):245-246 (1989)

Frangioni and Neel, "Solubilization and purification of enzymatically active glutathione S-transferase (pGEX) fusion proteins," *Anal Biochem* 210(1):179-187 (1993)

Gelfand et al, "Purified thermostable enzyme", U.S. Pat. No. 4,889,818, issued Dec. 26, 1989

Geysen et al, "Strategies for epitope analysis using peptide synthesis" *J Immunol Meth* 102(2):259-274 (1987)

Geysen H M, *Immunol Today* 6:364-369 (1985)

Goldstein N I, "Method of producing monoclonal anti-idiotype antibody", U.S. Pat. No. 4,699,880, issued Oct. 13, 1987

Gossen and Boujard, "Tight control of gene expression in mammalian cells by tetracycline-responsive promoters," *Proc Natl Acad Sci USA* 89(12):5547-5551 (1992)

Grell et al, "Segregation of APO-1/Fas antigen- and tumor necrosis factor receptor-mediated apoptosis," *Eur J Immunol* 24(10):2563-6256 (1994)

Gyllensten et al, "Methods for generating single stranded DNA by the polymerase chain reaction", U.S. Pat. No. 5,066,584, issued Nov. 19, 1991

Harlow et al, *Antibodies: A Laboratory Manual*, Cold Spring Harbor Laboratory, Cold Spring Harbor, N.Y., (1988)

Heller et al Complementary DNA cloning of a receptor for tumor necrosis factor and demonstration of a shed form of the receptor," *Proc Natl Acad Sci USA* 87(16):6151-6155 (1990)

Henkart P A, "ICE family proteases: mediators of all apoptotic cell death?", *Immunity* 4(3):195-201 (1996)

Hohmann et al, "Two different cell types have different major receptors for human tumor necrosis factor (TNF alpha)", *J Biol Chem* 264(25):14927-14934 (1989)

Howard et al, "IL-1-converting enzyme requires aspartic acid residues for processing of the IL-1 beta precursor at two distinct sites and does not cleave 31-kDa IL-1 alpha" *J Immunol* 147(9):2964-2969 (1991)

Hsu et al, "TRADD-TRAF2 and TRADD-FADD interactions define two distinct TNF receptor 1 signal transduction pathways", *Cell* 84(2):299-308 (1996)

Hsu et al, "The TNF receptor 1-associated protein TRADD signals cell death and NF-kappa B activation" *Cell* 81(4):495-504 (1995)

Innis M A, "Structure-independent DNA amplification by the polymerase chain reaction", U.S. Pat. No. 5,142,033, issued Aug. 25, 1992

Innis M A, "Structure-independent DNA amplification by polymerase chain reaction", U.S. Pat. No. 5,142,033, issued Feb. 25, 1992

Innis et al, eds., PCR Protocols: A Guide to Method and Applications, Academic Press (1990)

Itoh et al, "The polypeptide encoded by the cDNA for human cell surface antigen Fas can mediate apoptosis", *Cell.* 66(2):233-243 (1991)

Itoh and Nagata, "A novel protein domain required for apoptosis. Mutational analysis of human Fas antigen", *J Biol Chem* 268(15):10932-10937 (1993)

Joseph et al, "Optimization of an anti-HIV hairpin ribozyme by in vitro selection", *J Biol Chem* 268:24515-24518 (1993)

Kamens et al, "Identification and characterization of ICH-2, a novel member of the interleukin-1 beta-converting enzyme family of cysteine proteases," *J Biol Chem* 270(25):15250-15256 (1995)

Kaufmann et al, "Specific proteolytic cleavage of poly(ADP-ribose) polymerase: an early marker of chemotherapy-induced apoptosis", *Cancer Res* 53(17):3976-3985 (1993)

Kaufmann S H, "Induction of endonucleolytic DNA cleavage in human acute myelogenous leukemia cells by etoposide, camptothecin, and other cytotoxic anticancer drugs: a cautionary note" *Cancer Res* 49(21):5870-5878 (1989)

Kischkel et al, "Cytotoxicity-dependent APO-1 (Fas/CD95)-associated proteins form a death-inducing signaling complex (DISC) with the receptor", *EMBO J* 14(22):5579-5588 (1995)

Kohler et al, "Continuous cultures of fused cells secreting antibody of predefined specificity", *Nature* 256:495-497 (1975)

Koizumi et al, "Inhibition of c-Ha-ras gene expression by hammerhead ribozymes containing a stable C(UUCG)G hairpin loop," *Biol Pharm Bull* 16(9):879-883 (1993)

Koths et al, "Oxidation-resistant muteins of Il-2 and other protein", U.S. Pat. No. 5,116,943, issued May 26, 1992

Kudo et al, "Mouse-human chimaeric immunoglobulin heavy chain specific for the call antigen", European patent 0 184 187, published Jun. 11, 1986

Kumar S, "ICE-like proteases in apoptosis", *Trends Biochem Sci* 20(5):198-202 (1995)

Kumar et al, "Induction of apoptosis by the mouse Nedd2 gene, which encodes a protein similar to the product of the *Caenorhabditis elegans* cell death gene ced-3 and the mammalian IL-1 beta-converting enzyme," *Genes Dev* 8(14):1613-1626 (1994)

Lazebnik et al, "Cleavage of poly(ADP-ribose) polymerase by a proteinase with properties like ICE", *Nature* 371(6495):346-347 (1994)

Lee et al, "Mammalian interleukin-4", U.S. Pat. No. 5,017,691, issued May 21, 1991

Leithauser et al, "Constitutive and induced expression of APO-1, a new member of the nerve growth factor/tumor necrosis factor receptor superfamily, in normal and neoplastic cells," *Lab Invest* 69(4):415-29 (1993)

Liu et al, "Chimeric mouse-human IgG1 antibody that can mediate lysis of cancer cells", *Proc Natl Acad Sci USA* 84(10):3439-3443 (1987)

Loetscher et al, Molecular cloning and expression of the human 55 kd tumor necrosis factor receptor," *Cell* 61(2):351-359 (1990)

Los et al, "Requirement of an ICE/CED-3 protease for Fas/APO-1-mediated apoptosis," *Nature* 375(6526):81-83 (1995)

Low et al, "Method for enhanced transmembrane transport of exogenous molecules", U.S. Pat. No. 5,108,921, issued Apr. 28, 1992

Malek et al, "Enhanced nucleic acid amplification process", U.S. Pat. No. 5,130,238, issued Jul. 14, 1992

Mark et al, "Human recombinant interleukin-2 muteins", U.S. Pat. No. RE33,653, issued Jul. 30, 1991

Mark et al, "Cysteine-depleted muteins of biologically active proteins", U.S. Pat. No. 4,959,314, issued Sep. 25, 1990

Mark et al, "Human recombinant cysteine depleted interferon-β muteins", U.S. Pat. No. 4,588,585, issued May 13, 1986

Mark et al, "Structural genes, plasmids and transformed cells for producing cysteine depleted muteins of interferon-β", U.S. Pat. No. 4,737,462, issued Apr. 12, 1988

Martin et al, "Proteolysis of fodrin (non-erythroid spectrin) during apoptosis," *J Biol Chem* 270(12):6425-6428 (1995)

Mashima et al, "Aspartate-based inhibitor of interleukin-1 beta-converting enzyme prevents antitumor agent-induced apoptosis in human myeloid leukemia U937 cells", *Biochem Biophys Res Commun* 209(3):907-915 (1995)

Messing et al, Third Cleveland Symposium on Macromolecules and Recombinant DNA, Editor A. Walton, Elsevier, Amsterdam (1981)

Miller et al, "Inhibition of mature IL-1 beta production in murine macrophages and a murine model of inflammation by WIN 67694, an inhibitor of IL-1 beta converting enzyme," *J Immunol* 154(3):1331-1338 (1995)

Milligan et al, "Peptide inhibitors of the ICE protease family arrest programmed cell death of motoneurons in vivo and in vitro", *Neuron* 15(2):385-393 (1995)

Miura et al, "Tumor necrosis factor-induced apoptosis is mediated by a CrmA-sensitive cell death pathway," *Proc Natl Acad Sci USA* 92(18):8318-8322 (1995)

Morrison et al, "Chimeric human antibody molecules: mouse antigen-binding domains with human constant region domains". *Proc Natl Acad Sci USA* 81:6851-6855 (1984)

Morrison et al, "Chimeric receptors by DNA splicing and expression" European patent 0 173 494, published Mar. 5, 1986

Mullis et al, "Process for amplifying, detecting, and/or cloning nucleic acid sequences using a thermostable enzyme", U.S. Pat. No. 4,965,188, issued Oct. 23, 1990

Mullis et al, "Process for amplifying, detecting, and/or cloning nucleic acid sequences", U.S. Pat. No. 4,800,159, issued Jan. 24, 1989

Mullis K, "Process for amplifying nucleic acid sequences", U.S. Pat. No. 4,683,202, issued Jul. 28, 1987

Mullis K, "Process for amplifying, detecting, and/or-cloning nucleic acid sequences", U.S. Pat. No. 4,683,195, issued Jul. 28, 1987

Munday et al, "Molecular cloning and pro-apoptotic activity of ICErelII and ICErelIII, members of the ICE/CED-3 family of cysteine proteases," *J Biol Chem* 270(26):15870-15876 (1995)

Muranishi et al, "Lipophilic peptides: synthesis of lauroyl thyrotropin-releasing hormone and its biological activity", *Pharm Research* 8:649-652 (1991)

Nagata and Golstein, "The Fas death factor", *Science* 267 (5203):1449-1456 (1995)

Namen et al, "Interleukin-7", U.S. Pat. No. 4,965,195, issued Oct. 23, 1990

Neuberger et al, "Production of Chimeric Antibodies", international publication WO 86/01533, published Mar. 13, 1986

Neuberger et al, "A hapten-specific chimaeric IgE antibody with human physiological effector function", *Nature* 314:268-270 (1985)

Nicholson et al, "Identification and inhibition of the ICE/CED-3 protease necessary for mammalian apoptosis," *Nature* 376(6535):37-43 (1995)

Nophar et al, "Soluble forms of tumor necrosis factor receptors (TNF-Rs). The cDNA for the type I TNF-R, cloned using amino acid sequence data of its soluble form, encodes both the cell surface and a soluble form of the receptor", *EMBO J.* 9(10):3269-3278 (1990)

Piquet et al, "Tumor necrosis factor/cachectin is an effector of skin and gut lesions of the acute phase of graft-vs.-host disease," *J Exp Med* 166(5):1280-1289 (1987)

Ray et al, "Viral inhibition of inflammation: cowpox virus encodes an inhibitor of the interleukin-1 beta converting enzyme," *Cell* 69(4):597-604 (1992)

Ringold GM, "Gene amplification in eukaryotic cells", U.S. Pat. No. 4,656,134, issued Apr. 7, 1987

Robinson et al, "Modular Assembly of Antibody Genes, Antibodies Prepared Thereby and Use", international publication WO 87/02671, published May 7, 1987

Ruggiero et al, "Protection from tumor necrosis factor cytotoxicity by protease inhibitors," *Cell Immunol* 107(2):317-325 (1987)

Ruzicka et al, Immuno-PCR with a commercially available avidin system" *Science* 260(5108):698-699 (1993)

Sahagan et al, "A genetically engineered murine/human chimeric antibody retains specificity for human tumor-associated antigen" *J Immunol* 137:1066-1074 (1986)

Sambrook et al (1989) Molecular Cloning: A Laboratory Manual, Cold Spring Harbor Laboratory Press, Cold Spring Harbor, N.Y.

Sambrook et al, Molecular Cloning: A Laboratory Manual, Cold Spring Harbor Laboratory, Cold Spring Harbor, N.Y., 1989.

Sano et al, Immuno-PCR: very sensitive antigen detection by means of specific antibody-DNA conjugates", *Science* 258 (5079):120-122 (1992)

Sano et al, "A streptavidin-protein A chimera that allows one-step production of a variety of specific antibody conjugates", *Biotechnology (NY)* 9(12):1378-1381 (1991)

Schall et al, "Molecular cloning and expression of a receptor for human tumor necrosis factor", *Cell* 61(2):361-370 (1990)

Schlegel et al, "CPP32/apopain is a key interleukin 1 beta converting enzyme-like protease involved in Fas-mediated apoptosis," *J Biol Chem* 271(4):1841-1844 (1996)

Schulz et al, *Principles of Protein Structure*, Springer-Verlag, New York, N.Y., 1979

Schulze-Osthoff et al, "Divergent signalling via APO-1/Fas and the TNF receptor, two homologous molecules involved in physiological cell death," *EMBO J* 13(19):4587-4596 (1994)

Shaw G, "Site-specific homogenous modification of polypeptides", U.S. Pat. No. 4,904,584, issued Feb. 27, 1990

Shimayama et al, "Cleavage of the highly conserved hairpin-loop region of HIV-1 by synthetic ribozymes", *Nucleic Acids Symp Ser* 29:177-178 (1993)

Shore et al, "Ribozyme-mediated cleavage of the BCRABL oncogene transcript: in vitro cleavage of RNA and in vivo loss of P210 protein-kinase activity", *Oncogene* 8:3183-3188 (1993)

Silver et al, "DNA amplification technique", U.S. Pat. No. 4,994,370, issued Feb. 19, 1991

Sleath et al, "Substrate specificity of the protease that processes human interleukin-1 beta", *J Biol Chem* 265(24):14526-14528 (1990)

Smith et al, "A receptor for tumor necrosis factor defines an unusual family of cellular and viral proteins," *Science* 248 (4958):1019-1023 (1990)

Song et al, "Aggregation of the intracellular domain of the type 1 tumor necrosis factor receptor defined by the two-hybrid system," *J Biol Chem* 269(36):22492-22495 (1994)

Stanger et al, "RIP: a novel protein containing a death domain that interacts with Fas/APO-1 (CD95) in yeast and causes cell death", *Cell* 81(4):513-523 (1995)

Sun et al, "Chimeric antibody with human constant regions and mouse variable regions directed against carcinoma-associated antigen 17-1A", *Proc Natl Acad Sci USA* 84:214-218 (1987)

Tabor et al, "T7 Polymerase", U.S. Pat. No. 4,921,794, issued May 1, 1990

Tabor et al, "T7 Polymerase", U.S. Pat. No. 4,795,699, issued Jan. 3, 1989

Taniguchi et al, "Process for the production of a chimera monoclonal antibody" European patent 0 171 496, published Feb. 19, 1986

Tartaglia et al, "A novel domain within the 55 kd TNF receptor signals cell death", *Cell* September 10; 74(5):845-853 (1993)

Tewari et al, "CrmA-inhibitable cleavage of the 70-kDa protein component of the U1 small nuclear ribonucleoprotein during Fas- and tumor necrosis factor-induced apoptosis," *J Biol Chem* 270(32):18738-18741 (1995a)

Tewari et al, "Yama/CPP32 beta, a mammalian homolog of CED-3, is a CrmA-inhibitable protease that cleaves the death substrate poly(ADP-ribose) polymerase," *Cell* 81(5):801-809 (1995b)

Tewari et al, Fas- and tumor necrosis factor-induced apoptosis is inhibited by the poxvirus crmA gene product," *J Biol Chem* 270(7):3255-3260 (1995)

Thornberry et al, "Inactivation of interleukin-1 beta converting enzyme by peptide (acyloxy)methyl ketones" *Biochemistry* 33(13):3934-3940 (1994)

Thornberry et al, "A novel heterodimeric cysteine protease is required for interleukin-1 beta processing in monocytes" *Nature* 356(6372):768-774 (1992)

Tracey et al, "Anti-cachectin/TNF monoclonal antibodies prevent septic shock during lethal bacteraemia," *Nature* 330(6149):662-664 (1987)

Vandenabeele et al, "Two tumour necrosis factor receptors: structure and function", *Trends Cell Biol* 5, 392-399 (1995)

Vassalli P "The pathophysiology of tumor necrosis factors", *Ann Rev Immunol* 10:411-452 (1992)

Vieira et al, "Production of single-stranded plasmid DNA", *Methods Enzymol* 153:3-11 (1987)

Wahl et al, "Improved radioimaging and tumor localization with monoclonal F(ab')2", *J Nucl Med* 24(4):316-325 (1983)

Wallach et al, "Modulator of TNF/NGF Superfamily Receptors and soluble Oligomeric TNF/NGF Superfamily Receptors," international application WO 95/31544, published Nov. 23, 1995

Wallach et al, "P75 TNF Receptor Promoters," international application WO 95/31206 published Nov. 23, 1995

Wallach et al, *Cytokine* 6:556 (1994)

Wallach et al, "Promotor sequence of the p55 tumor necrosis factor receptor," European application EP 0 606 869, published Jul. 20, 1994

Wallach et al, "Antibodies to TNF binding protein I and F (ab) fragments thereof, European application EP 0 412 486, published Feb. 13, 1991

Wallach et al, "Tumor necrosis factor binding protein II, its purification and antibodies thereto," European application EP 0 398 327, published Nov. 22, 1990

Wallach et al, "Tumor necrosis factor (TNF) inhibitory protein and its purification," European application EP 0 308 378, published Mar. 22, 1989

Wallach et al, "A monoclonal antibody recognizing a cytotoxin, a hybridoma cell line expressing same and a process for the preparation of a purified cytotoxin," European application EP 0 186 833, published Jul. 9, 1986

Wallach D, in *Interferon* 7 (Ion Gresser, ed.), pp. 83-122, Academic Press, London (1986)

Wallach D, "Preparations of lymphotoxin induce resistance to their own cytotoxic effect", *J Immunol* 132:2464-2469 (1984)

Wang et al, "Ich-1, an Ice/ced-3-related gene, encodes both positive and negative regulators of programmed cell death", *Cell* 78(5):739-750 (1994)

Watanabe-Fukunaga et al, "Lymphoproliferation disorder in mice explained by defects in Fas antigen that mediates apoptosis," *Nature,* 356(6367):314-317 (1992)

Watanabe-Fukunaga et al, "The cDNA structure, expression, and chromosomal assignment of the mouse Fas antigen," *J Immunol* 148(4):1274-1279 (1992)

Weitzen M et al, "The human LT system. VIII. A target cell-dependent enzymatic activation step required for the expression of the cytotoxic activity of human lymphotoxin," *J Immunol* 125(2):719-724 (1980)

Wilks et al, "Two putative protein-tyrosine kinases identified by application of the polymerase chain reaction", *Proc Natl Acad Sci USA* 86(5):1603-1607 (1989)

Wilson et al, "Method for dominant selection in eucaryotic cells", U.S. Pat. No. 5,122,464, issued Jun. 16, 1992

Wong et al, "Fas antigen and p55 TNF receptor signal apoptosis through distinct pathways," *J Immunol* 152(4):1751-1755 (1994)

Work et al (eds), *Laboratory Techniques and Biochemistry in Molecular Biology*, North Holland Publishing Company, NY (1978)

Xue et al, "Inhibition of the *Caenorhabditis elegans* cell-death protease CED-3 by a CED-3 cleavage site in baculovirus p35 protein", *Nature* 377(6546):248-251 (1995)

Yonehara et al, "A cell-killing monoclonal antibody (anti-Fas) to a cell surface antigen co-downregulated with the receptor of tumor necrosis factor," *J Exp Med* 169(5):1747-1756 (1989)

Yuan et al, "The *C. elegans* cell death gene ced-3 encodes a protein similar to mammalian interleukin-1 beta-converting enzyme," *Cell* 75(4):641-652 (1993)

Zacharia et al, "New reduced peptide bond substance P agonists and antagonists: effects on smooth muscle contraction", *Eur J Pharmacol* 203:353-357 (1991)

Zhao et al, "Generating loss-of-function phenotypes of the fushi tarazu gene with a targeted ribozyme in Drosophila", *Nature* 365:448-451 (1993)

---

What is claimed is:

1. An isolated molecule comprising an antigen binding fragment of an antibody capable of binding to a polypeptide whose sequence is 1-182 of SEQ ID NO:5.

2. An isolated molecule in accordance with claim 1, comprising a monoclonal antibody.

3. An isolated antibody capable of binding to a polypeptide whose sequence is 1-182 of SEQ ID NO:5.

* * * * *